(12) United States Patent
Drescher et al.

(10) Patent No.: US 7,759,397 B2
(45) Date of Patent: Jul. 20, 2010

(54) 6-AMINO(AZA)INDANE COMPOUNDS SUITABLE FOR TREATING DISORDERS THAT RESPOND TO MODULATION OF THE DOPAMINE $D_3$ RECEPTOR

(75) Inventors: Karla Drescher, Dossenheim (DE); Andreas Haupt, Schwetzingen (DE); Liliane Unger, Ludwigshafen (DE); Sean C. Turner, Mannheim (DE); Wilfried Braje, Mannheim (DE); Roland Grandel, Dossenheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 222 days.

(21) Appl. No.: 11/665,420

(22) PCT Filed: Oct. 14, 2005

(86) PCT No.: PCT/EP2005/011090

§ 371 (c)(1),
(2), (4) Date: Sep. 24, 2007

(87) PCT Pub. No.: WO2006/040177

PCT Pub. Date: Apr. 20, 2006

(65) Prior Publication Data

US 2008/0318996 A1 Dec. 25, 2008

Related U.S. Application Data

(60) Provisional application No. 60/618,743, filed on Oct. 14, 2004.

(51) Int. Cl.
*A61K 31/135* (2006.01)
*C07C 211/00* (2006.01)

(52) U.S. Cl. .................. 514/647; 564/308; 564/307

(58) Field of Classification Search .......... 514/647; 564/308, 307
See application file for complete search history.

(56) References Cited

U.S. PATENT DOCUMENTS 5,708,018 A * 1/1998 Haadsma-Svensson et al. .. 514/408
5,936,000 A * 8/1999 Romero et al. ............. 514/647

FOREIGN PATENT DOCUMENTS

| WO | WO 95/04713 | 2/1995 |
| WO | WO 96/23760 | 8/1996 |
| WO | WO 97/45503 | 12/1997 |

OTHER PUBLICATIONS

J.C. Schwartz et al., The Dopamine $D_3$ Receptor as a Target for Antipsychotics, in Novel Antipsychotic Drugs, H.Y. Meltzer, Ed. Raven Press, New York, 1992, pp. 135-144.
M. Dooley et al., Drugs and Aging 1998, 12, 495-514.
J. N. Joyce, Pharmacology and Therapeutics 2001, 90, pp. 231-259 "The Dopamine $D_3$ Receptor as a Therapeutic Target for Antipsychotic and Antiparkinsonian Drugs".
P. Sokoloff et al., Localization and Function of the $D_3$ Dopamine Receptor, Arzneim. Forsch./Drug Res. 42(1), 224 (1992).
P. Sokoloff et al., Molecular Cloning and Characterization of a Novel Dopamine Receptor ($D_3$) as a Target for Neuroleptics, Nature, 347, 146 (1990).
Joyce, J.N. Dopamine D3 receptor as a therapeutic target for antipsychotic and antiparkinsonian drugs. Pharmacology and Therapeutics, 2001;90:231-59.
Laszy, J., et al. Dopamine D3 receptor antagonists improve the learning performance in memory-impaired rats. Pscyhopharmacology, 2005;179:567-75.
Heidbreder, C.A., et al. The role of central dopamine D3 receptors in drug addiction: a review of pharmacological evidence. Brain Research Reviews, 2005;49:77-105.
Rogoz, Z., et al. Anxiolytic-like effects of preferential dopamine D3 receptor agonists in an animal model. Polish Journal of Pharmacology, 2003;55:449-54.
Muhlbauer B., et al.. Dopamine D3 receptors in the rat kidney: role in physiology and pathophysiology. Acta Physiologica Scandinavica, 2000;168(1):219-23.
Benoit S.C., et al. Altered feeding responses in mice with targeted disruption of the dopamine-3 receptor gene. Behavioral Neuroscience, 2003;117(1):46-54.

* cited by examiner

*Primary Examiner*—Rei-tsang Shiao
(74) *Attorney, Agent, or Firm*—Lisa V. Mueller; Polsinelli Shughart PC

(57) ABSTRACT

The present invention relates to 6-amino(aza)indane compound of the formula (I) Wherein Ar is phenyl or an aromatic 5- or 6-membered C-bound heteroaromatic radical, wherein Ar may carry 1 radical $R^a$ and wherein Ar may also carry 1 or 2 radicals $R^b$; X is N or CH; E is $CR^6R^7$ or $NR^3$; $R^1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl; $R^{1a}$ is H or $R^{1a}$ and $R^2$ or $R^{1a}$ and $R^{2a}$ together are $(CH_2)_n$ with n being 1, 2, 3 or 4; $R^2$ and $R^{2a}$ each independently are H, $CH_3$, $CH_2F$, $CHF_2$ or $CF_3$; $R^3$ is H or C,-C4-alkyl; and the physiologically tolerated acid addition salts of these compounds. The invention also relates to pharmaceutical compositions comprising at least one compound of the formula (I) or a pharmaceutically acceptable salt thereof and to a method for treating a medical disorder susceptible to treatment with a dopamine D3 receptor ligand, said method comprising administering an effective amount of at least one compound of the formula (I) or a pharmaceutically acceptable salt thereof.

(I)

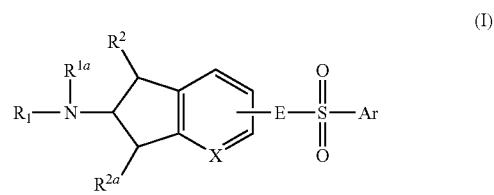

18 Claims, No Drawings

6-AMINO(AZA)INDANE COMPOUNDS SUITABLE FOR TREATING DISORDERS THAT RESPOND TO MODULATION OF THE DOPAMINE $D_3$ RECEPTOR

BACKGROUND OF THE INVENTION

The present invention relates to novel 6-amino(aza)indane compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmaco-logically, namely the $D_1$ and $D_2$ receptors. More recently, a third subtype was found, namely the $D_3$ receptor which appears to mediate some effects of antipsychotics and antiparkinsonians (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

6-aminoindane compounds having an affinity for the dopamine $D_3$ receptor have been described in WO 95/04713, WO 96/23760 and WO 97/45403. Some of these compounds possess high affinities for the dopamine $D_3$ receptor. They have therefore been proposed as being suitable for treating diseases of the central nervous system. Unfortunately their affinity and selectivity towards the $D_3$ receptor or their pharmacological profile are not satisfactory. Consequently there is an ongoing need to provide new compounds, which either have an high affinity and an improved selectivity. The compounds should also have good pharmacological profile, e.g. a high brain plasma ratio, a high bioavailability, a good metabolic stability or a decreased inhibition of the mitochondrial respiration.

SUMMARY OF THE INVENTION

The invention is based on the object of providing compounds which act as highly selective dopamine $D_3$ receptor ligands. This object is surprisingly achieved by means of 6-amino(aza)indane compound of the formula I

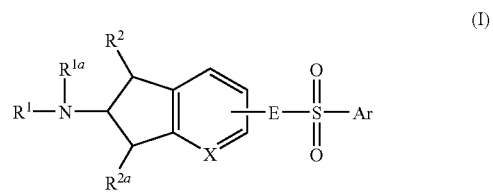

wherein

Ar is phenyl or an aromatic 5- or 6-membered C-bound heteroaromatic radical, wherein Ar may carry 1 radical $R^a$ and wherein Ar may carry 1 or 2 further radicals $R^b$;

$R^a$ being selected from the group consisting of $C_1$-$C_6$-alkyl, $C_2$-$C_6$-alkenyl, fluorinated $C_2$-$C_6$-alkenyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenyl, phenoxy, benzyloxy and a 3- to 7-membered heterocyclic radical, wherein the five last mentioned radicals may carry 1, 2, 3 or 4 radicals selected from halogen, cyano, OH, oxo, CN, and the radicals $R^a$, $R^b$ being, independently from each other, selected from halogen, cyano, nitro, OH, methyl, methoxy, fluoromethyl, difluoromethyl, trifluoromethyl, fluormethoxy, difluoromethoxy and trifluoromethoxy, the radical $R^a$ and one radical $R^b$, if present and bound to two adjacent carbon atoms of phenyl, may form a 5- or 6-membered heterocyclic or carbocylic ring which is fused to the phenyl ring and which is unsubstituted or which may carry 1, 2 or 3 radicals selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl;

provided that if Ar is phenyl, $R^{2a}$ is hydrogen and $R^{2b}$ is hydrogen and A is $CH_2$, Ar carries 1 radical $R^a$ which is different from methyl, methoxy, trifluormethyl and trifluoromethoxy, and optionally 1 or 2 radicals $R^b$;

X is N or CH;

E is $CR^6R^7$ or $NR^3$;

$R^1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H or $R^{1a}$ and $R^2$ or $R^{1a}$ and $R^{2a}$ together are $(CH_2)_n$ with n being 1, 2, 3 or 4;

$R^2$ and $R^{2a}$ each independently are H, $CH_3$, $CH_2F$, $CHF_2$ or $CF_3$ $R^3$ is H or $C_1$-$C_4$-alkyl;

$R^4$, $R^5$ independently of each other are selected from H, $C_1$-$C_2$-alkyl, $C_1$-$C_2$-alkoxy and fluorinated $C_1$-$C_2$-alkyl, and $R^6$, $R^7$ independently of each other are selected from H, $C_1$-$C_2$-alkyl and fluorinated $C_1$-$C_2$-alkyl, in particular hydrogen;

and the physiologically tolerated acid addition salts of these compounds.

The present invention therefore relates to 6-amino(aza) indane compounds of the general formula I and to their physiologically tolerated acid addition salts.

The present invention also relates to a pharmaceutical composition which comprises at least one 6-amino(aza)indane compound of the formula I and/or at least one physiologically tolerated acid addition salt of 1, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one 6-amino(aza)indane compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

$C_1$-$C_4$ Alkyl (and likewise in $C_1$-$C_4$ hydroxyalkyl, $C_1$-$C_6$ alkoxy-$C_1$-$C_4$-alkyl, $C_1$-$C_4$ alkylcarbonyl, $C_1$-$C_4$ alkylcarbonylamino, $C_1$-$C_4$ alkylcarbonyloxy, $C_1$-$C_4$ alkylthio, $C_1$-$C_4$ alkylsulfinyl, $C_1$-$C_4$alkylsulfonyl etc.) is a straight-chain or branched alkyl group having from 1 to 4 carbon atoms. Examples of an alkyl group are methyl, ethyl, n-propyl, isopropyl, n-butyl, 2-butyl, iso-butyl or tert-butyl.

$C_1$-$C_6$ Alkyl (and likewise in $C_1$-$C_6$ hydroxyalkyl, $C_1$-$C_6$ alkoxy-$C_1$-$C_4$-alkyl, $C_1$-$C_6$ alkylcarbonyl, $C_1$-$C_6$ alkylcarbonylamino, $C_1$-$C_6$ alkylcarbonyloxy, $C_1$-$C_6$ alkylthio, $C_1$-$C_6$ alkylsulfinyl, $C_1$-$C_6$ alkylsulfonyl etc.) is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Fluorinated $C_1$-$C_6$ alkyl (and likewise in fluorinated $C_1$-$C_6$ alkylcarbonyl, fluorinated $C_1$-$C_6$ alkylcarbonylamino, fluorinated $C_1$-$C_6$ alkylcarbonyloxy, fluorinated $C_1$-$C_6$ alkylthio, fluorinated $C_1$-$C_6$ alkylsulfinyl, fluorinated $C_1$-$C_6$ alkylsulfonyl etc.) is a straight-chain or branched alkyl group having from 1 to 6, in particular 1 to 4, more preferably 1 to 3 carbon atoms, wherein at least one, e.g. 1, 2, 3, 4 or all of the hydrogen atoms are replaced by a fluorine atoms such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, etc.;

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl 1-methyl-1-ethylpropyl.

$C_1$-$C_6$ Alkoxy (and likewise in $C_1$-$C_6$ alkoxycarbonyl, $C_1$-$C_6$ alkoxy-$C_1$-$C_4$ alkyl, $C_1$-$C_6$ alkoxy-$C_1$-$C_4$ alkoxy and $C_1$-$C_6$ hydroxyalkoxy) is a straight-chain or branched alkyl group having from 1 to 6, in particular 1 to 4 carbon atoms, which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutyoxy, 2-methylbutyoxy, 3-methylbutyoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy;

Fluorinated $C_1$-$C_6$ alkoxy (and likewise in fluorinated $C_1$-$C_6$ alkoxycarbonyl) is a straight-chain or branched alkoxy group having from 1 to 6, in particular 1 to 4 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.;

$C_3$-$C_6$ Cycloalkyl is a cycloaliphatic radical having from 3 to 6 C atoms, such as cyclopropyl, cyclobutyl and cyclopentyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl and cyclopentyl, wherein at least one, e.g. 1, 2, 3, 4 or all of the hydrogen atoms are replaced by a fluorine atoms such as in 1-fluorocyclopropyl, 2-fluorocyclopropyl, 2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl(2-propen-1-yl), 1-propen-1-yl, 2-propen-2-yl, methallyl(2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_1$-$C_6$ hydroxyalkyl is an alkyl radical having from 1 to 6 carbon atoms as defined above, wherein one hydrogen atom is replaced by hydroxy. Examples comprise hydroxymethyl, 2-hydroxyethyl, 1-hydroxyethyl, 3-hydroxypropyl, 2-hydroxypropyl, 1-methyl-1-hydroxyethyl and the like.

$C_1$-$C_6$ hydroxyalkoxy is an alkoxy radical having from 1 to 6, preferably from 2 to 4 carbon atoms as defined above, wherein one hydrogen atom is replaced by hydroxy. Examples comprise 2-hydroxyethyl, 3-hydroxypropyl, 2-hydroxypropyl, 1-methyl-2-hydroxyethyl and the like.

$C_1$-$C_6$ alkoxy-$C_1$-$C_4$-alkyl is an alkyl radical having from 1 to 4 carbon atoms as defined above, wherein one hydrogen atom is replaced by $C_1$-$C_6$ alkoxy. Examples comprise methoxymethyl, 2-methoxyethyl, 1-methoxyethyl, 3-methoxypropyl, 2-methoxypropyl, 1-methyl-1-methoxyethyl, ethoxymethyl, 2-ethoxyethyl, 1-ethoxyethyl, 3-ethoxypropyl, 2-ethoxypropyl, 1-methyl-1-ethoxyethyl and the like.

$C_1$-$C_6$ alkoxy-$C_1$-$C_4$-alkoxy is an alkoxy radical having from 1 to 4 carbon atoms as defined above, wherein one hydrogen atom is replaced by $C_1$-$C_6$ alkoxy. Examples comprise methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

$C_1$-$C_6$ alkylcarbonyl is a radical of the formula R—C(O)—, wherein R is an alkyl radical having from 1 to 6 carbon atoms as defined above. Examples comprise acetyl, propionyl, n-butylryl, 2-methylpropionyl, pivalyl and the like.

$C_1$-$C_6$ alkylcarbonylamino is a radical of the formula R—C(O)—NH—, wherein R is an alkyl radical having from 1 to 6 carbon atoms as defined above. Examples comprise acetamido, propionamido, n-butyramido, 2-methylpropionamido, 2,2-dimethylpropionamido and the like.

$C_1$-$C_6$ alkylcarbonyloxy is a radical of the formula R—C(O)—O—, wherein R is an alkyl radical having from 1 to 6 carbon atoms as defined above. Examples comprise acetyloxy, propionyloxy, n-butyryloxy, 2-methylpropionyloxy, 2,2-dimethylpropionyloxy and the like.

$C_1$-$C_6$ alkylthio is a radical of the formula R—S—, wherein R is an alkyl radical having from 1 to 6 carbon atoms as defined above. Examples comprise methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl;

$C_1$-$C_6$ alkylsulfinyl is a radical of the formula R—S(O)—, wherein R is an alkyl radical having from 1 to 6 carbon atoms as defined above. Examples comprise methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl;

$C_1$-$C_6$ alkylsulfonyl is a radical of the formula R—S(O)$_2$—, wherein R is an alkyl radical having from 1 to 6 carbon atoms as defined above. Examples comprise methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl;

fluorinated $C_1$-$C_6$ alkylcarbonyl is a radical of the formula R—C(O)—, wherein R is a fluorinated alkyl radical having from 1 to 6 carbon atoms as defined above. Examples comprise fluoroacetyl, difluoroacetyl, trifluoroacetyl, (R)-1-fluoroethylcarbonyl, (S)-1-fluoroethylcarbonyl, 2-fluoroethylcarbonyl, 1,1-difluoroethylcarbonyl, 2,2-difluoroethylcarbonyl, 2,2,2-trifluoroethylcarbonyl, (R)-1-fluoropropylcarbonyl, (S)-1-fluoropropylcarbonyl, 2-fluoropropylcarbonyl, 3-fluoropropylcarbonyl, 1,1-difluoropropylcarbonyl, 2,2-difluoropropylcarbonyl, 3,3-difluoropropylcarbonyl, 3,3,3-trifluoropropylcarbonyl, (R)-2-fluoro-1-methylethylcarbonyl, (S)-2-fluoro-1-methylethylcarbonyl, (R)-2,2-difluoro-1-methylethylcarbonyl, (S)-2,2-difluoro-1-methylethylcarbonyl, (R)-1,2-difluoro-1-methylethylcarbonyl, (S)-1,2-difluoro-1-methylethylcarbonyl, (R)-2,2,2-trifluoro-1-methylethylcarbonyl, (S)-2,2,2-trifluoro-1-methylethylcarbonyl, 2-fluoro-1-(fluoromethyl)ethylcarbonyl, 1-(difluoromethyl)-2,2-difluoroethylcarbonyl, (R)-1-fluorobutylcarbonyl, (S)-1-fluorobutylcarbonyl, 2-fluorobutylcarbonyl, 3-fluorobutylcarbonyl, 4-fluorobutylcarbonyl, 1,1-difluorobutylcarbonyl, 2,2-difluorobutylcarbonyl, 3,3-difluorobutylcarbonyl, 4,4-difluorobutylcarbonyl, 4,4,4-trifluorobutylcarbonyl, etc.;

fluorinated $C_1$-$C_6$ alkylcarbonylamino is a radical of the formula R—C(O)—NH—, wherein R is a fluorinated alkyl radical having from 1 to 6 carbon atoms as defined above. Examples comprise fluoroacetamido, difluoroacetamido, trifluoroacetamido, (R)-1-fluoroethylcarbonylamino, (S)-1-fluoroethylcarbonylamino, 2-fluoroethylcarbonylamino, 1,1-difluoroethylcarbonylamino, 2,2-difluoroethylcarbonylamino, 2,2,2-trifluoroethylcarbonylamino, (R)-1-fluoropropylcarbonylamino, (S)-1-fluoropropylcarbonylamino, 2-fluoropropylcarbonylamino, 3-fluoropropylcarbonylamino, 1,1-difluoropropylcarbonylamino, 2,2-difluoropropylcarbonylamino, 3,3-difluoropropylcarbonylamino, 3,3,3-trifluoropropylcarbonylamino, (R)-2-fluoro-1-methylethylcarbonylamino, (S)-2-fluoro-1-methylethylcarbonylamino, (R)-2,2-difluoro-1-methylethylcarbonylamino, (S)-2,2-difluoro-1-methylethylcarbonylamino, (R)-1,2-difluoro-1-methylethylcarbonylamino, (S)-1,2-difluoro-1-methylethylcarbonylamino, (R)-2,2,2-trifluoro-1-methylethylcarbonylamino, (S)-2,2,2-trifluoro-1-methylethylcarbonylamino, 2-fluoro-1-(fluoromethyl)ethylcarbonylamino, 1-(difluoromethyl)-2,2-difluoroethylcarbonylamino, (R)-1-fluorobutylcarbonylamino, (S)-1-fluorobutylcarbonylamino, 2-fluorobutylcarbonylamino, 3-fluorobutylcarbonylamino, 4-fluorobutylcarbonylamino, 1,1-difluorobutylcarbonylamino, 2,2-difluorobutylcarbonylamino, 3,3-difluorobutylcarbonylamino, 4,4-difluorobutylcarbonylamino, 4,4,4-trifluorobutylcarbonylamino, etc., fluorinated $C_1$-$C_6$ alkylcarbonyloxy is a radical of the formula R—C(O)—O—, wherein R is a fluorinated alkyl radical having from 1 to 6 carbon atoms as defined above fluoroacetyl, difluoroacetyl, trifluoroacetyl, (R)-1-fluoroethylcarbonyloxy, (S)-1-fluoroethylcarbonyloxy, 2-fluoroethylcarbonyloxy, 1,1-difluoroethylcarbonyloxy, 2,2-difluoroethylcarbonyloxy, 2,2,2-trifluoroethylcarbonyloxy, (R)-1-fluoropropylcarbonyloxy, (S)-1-fluoropropylcarbonyloxy, 2-fluoropropylcarbonyloxy, 3-fluoropropylcarbonyloxy, 1,1-difluoropropylcarbonyloxy, 2,2-difluoropropylcarbonyloxy, 3,3-difluoropropylcarbonyloxy, 3,3,3-trifluoropropylcarbonyloxy, (R)-2-fluoro-1-methylethylcarbonyloxy, (S)-2-fluoro-1-methylethylcarbonyloxy, (R)-2,2-difluoro-1-methylethylcarbonyloxy, (S)-2,2-difluoro-1-methylethylcarbonyloxy, (R)-1,2-difluoro-1-methylethylcarbonyloxy, (S)-1,2-difluoro-1-methylethylcarbonyloxy, (R)-2,2,2-trifluoro-1-methylethylcarbonyloxy, (S)-2,2,2-trifluoro-1-methylethylcarbonyloxy, 2-fluoro-1-(fluoromethyl)ethylcarbonyloxy, 1-(difluoromethyl)-2,2-difluoroethylcarbonyloxy, (R)-1-fluorobutylcarbonyloxy, (S)-1-fluorobutylcarbonyloxy, 2-fluorobutylcarbonyloxy, 3-fluorobutylcarbonyloxy, 4-fluorobutylcarbonyloxy, 1,1-difluorobutylcarbonyloxy, 2,2-difluorobutylcarbonyloxy, 3,3-difluorobutylcarbonyloxy, 4,4-difluorobutylcarbonyloxy, 4,4,4-trifluorobutylcarbonyloxy, etc.;

fluorinated $C_1$-$C_6$ alkylthio is a radical of the formula R—S—, wherein R is a fluorinated alkyl radical having from 1 to 6 carbon atoms as defined above. Examples comprise fluoromethylthio, difluoromethylthio, trifluoromethylthio, (R)-1-fluoroethylthio, (S)-1-fluoroethylthio, 2-fluoroethylthio, 1,1-difluoroethylthio, 2,2-difluoroethylthio, 2,2,2-trifluoroethylthio, (R)-1-fluoropropylthio, (S)-1-fluoropropylthio, 2-fluoropropylthio, 3-fluoropropylthio, 1,1-difluoropropylthio, 2,2-difluoropropylthio, 3,3-difluoropropylthio, 3,3,3-trifluoropropylthio, (R)-2-fluoro-1-methylethylthio, (S)-2-fluoro-1-methylethylthio, (R)-2,2-difluoro-1-methylethylthio, (S)-2,2-difluoro-1-methylethylthio, (R)-1,2-difluoro-1-methylethylthio, (S)-1,2-difluoro-1-methylethylthio, (R)-2,2,2-trifluoro-1-methylethylthio, (S)-2,2,2-trifluoro-1-methylethylthio, 2-fluoro-1-(fluoromethyl)ethylthio, 1-(difluoromethyl)-2,2-difluoroethylthio, (R)-1-fluorobutylthio, (S)-1-fluorobutylthio, 2-fluorobutylthio, 3-fluorobutylthio, 4-fluorobutylthio, 1,1-difluorobutylthio, 2,2-difluorobutylthio, 3,3-difluorobutylthio, 4,4-difluorobutylthio, 4,4,4-trifluorobutylthio, etc.;

fluorinated $C_1$-$C_6$ alkylsulfinyl is a radical of the formula R—S(O)—, wherein R is a fluorinated alkyl radical having from 1 to 6 carbon atoms as defined above. Examples comprise fluoromethylsulfinyl, difluoromethylsulfinyl, trifluoromethylsulfinyl, (R)-1-fluoroethylsulfinyl, (S)-1-fluoroethylsulfinyl, 2-fluoroethylsulfinyl, 1,1-difluoroethylsulfinyl, 2,2-difluoroethylsulfinyl, 2,2,2-trifluoroethylsulfinyl, (R)-1-fluoropropylsulfinyl, (S)-1-fluoropropylsulfinyl, 2-fluoropropylsulfinyl, 3-fluoropropylsulfinyl, 1,1-difluoropropylsulfinyl, 2,2-difluoropropylsulfinyl, 3,3-difluoropropylsulfinyl, 3,3,3-trifluoropropylsulfinyl, (R)-2-fluoro-1-methylethylsulfinyl, (S)-2-fluoro-1-methylethylsulfinyl, (R)-2,2-difluoro-1-methylethylsulfinyl, (S)-2,2-difluoro-1-methylethylsulfinyl, (R)-1,2-difluoro-1-methylethylsulfinyl, (S)-1,2-difluoro-1-methylethylsulfinyl, (R)-2,2,2-trifluoro-1-methylethylsulfinyl, (S)-2,2,2-trifluoro-1-methylethylsulfinyl, 2-fluoro-1-(fluoromethyl)ethylsulfinyl, 1-(difluoromethyl)-2,2-difluoroethylsulfinyl, (R)-1-fluorobutylsulfinyl, (S)-1-fluorobutylsulfinyl, 2-fluorobutylsulfinyl, 3-fluorobutylsulfinyl, 4-fluorobutylsulfinyl, 1,1-difluorobutylsulfinyl, 2,2-difluorobutylsulfinyl, 3,3-difluorobutylsulfinyl, 4,4-difluorobutylsulfinyl, 4,4,4-trifluorobutylsulfinyl, etc.;

fluorinated $C_1$-$C_6$ alkylsulfonyl is a radical of the formula R—S(O)$_2$—, wherein R is a fluorinated alkyl radical having from 1 to 6 carbon atoms as defined above. Examples comprise fluoromethylsulfonyl, difluoromethylsulfonyl, trifluoromethylsulfonyl, (R)-1-fluoroethylsulfonyl, (S)-1-fluoroethylsulfonyl, 2-fluoroethylsulfonyl, 1,1-difluoroethylsulfonyl, 2,2-difluoroethylsulfonyl, 2,2,2-trifluoroethylsulfonyl, (R)-1-fluoropropylsulfonyl, (S)-1-fluoropropylsulfonyl, 2-fluoropropylsulfonyl, 3-fluoropropylsulfonyl, 1,1-difluoropropylsulfonyl, 2,2-difluoropropylsulfonyl, 3,3-difluoropropylsulfonyl, 3,3,3-trifluoropropylsulfonyl, (R)-2-fluoro-1-methylethylsulfonyl, (S)-2-fluoro-1-methylethylsulfonyl, (R)-2,2-difluoro-1-methylethylsulfonyl, (S)-2,2-difluoro-1-methylethylsulfonyl, (R)-1,2-difluoro-1-methylethylsulfonyl, (S)-1,2-difluoro-1-methylethylsulfonyl, (R)-2,2,2-trifluoro-1-methylethylsulfonyl, (S)-2,2,2-trifluoro-1-methylethylsulfonyl, 2-fluoro-1-(fluoromethyl)ethylsulfonyl, 1-(difluoromethyl)-2,2-difluoroethylsulfonyl, (R)-1-fluorobutylsulfonyl, (S)-1-fluorobutylsulfonyl, 2-fluorobutylsulfonyl, 3-fluorobutylsulfonyl, 4-fluorobutylsulfonyl, 1,1-difluorobutylsulfonyl, 2,2-difluorobutylsulfonyl, 3,3-difluorobutylsulfonyl, 4,4-difluorobutylsulfonyl, 4,4,4-trifluorobutylsulfonyl, etc.

3- to 7-membered heterocyclic radicals comprise saturated heterocyclic radicals, which generally have 3-, 4-, 5-, 6- or 7 ring forming atoms (ring members), unsaturated non-aromatic heterocyclic radicals, which generally have 5-, 6- or 7 ring forming atoms, and heteroaromatic radicals, which generally have 5-, 6- or 7 ring forming atoms. The heterocylcic radicals may be bound via a carbon atom (C-bound) or an nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of 3- to 7-membered, saturated heterocyclic radicals comprise 1- or 2-aziridinyl, 1-, 2- or 3-azetidinyl, 1-, 2- or 3-pyrrolidinyl, 1-, 2-, 3- or 4-piperidinyl, 1-, 2- or 3-morpholinyl, 1-, 2- or 3-thiomorpholinyl, 1-, 2- or 3-piperazinyl, 1-, 2- or 4-oxazolidinyl, 1-, 3- or 4-isoxazolidinyl, 2-oxiranyl, 2- or 3-oxetanyl, 2- or 3-oxolanyl, 2-, 3- or 4-oxanyl, 1,3-dioxolan-2- or 4-yl and the like, which may be unsubstituted or which may carry 1, 2 or 3 of the aforementioned radicals $R^a$ and/or $R^b$.

Unsaturated non-aromatic heterocyclic radicals, are heterocyclic radicals which generally have 5-, 6- or 7 ring forming atoms and which have 1 or 2 doublebonds that do not form an aromatic p-electron system. Examples are 2,3-dihydropyrrolyl, 3,4-dihydropyrrolyl, 2,3-dihydrofuranyl, 3,4-dihydrofuranyl, 2,3-dihydrothiophenyl, 3,4-dihydrothiophenyl, 1,2-dihydropyridinyl, 2,3-Dihydropyridiynl, 3,4-dihydropyridinyl, 1,2,3,4-tetrahydropyridinyl, 2,3,4,5-tetrahydropyridinyl, and the like.

5- or 6-membered heteroaromatic radicals are heteroaromatic cyclic radicals, wherein the cyclic radical has 5 or 6 atoms which form the ring (ring members) and wherein generally 1, 2, 3 or 4 ring member atoms are selected from O, S and N, the other ring member atoms being carbon atoms. The heteroaromatic radicals may be bound via a carbon atom (C-bound) or an nitrogen atom (N-bound). Preferred heteroaromatic radicals comprise 1 nitrogen atom as ring member atom and optionally 1, 2 or 3 further heteroatoms as ring members, which are selected, independently of each other from O, S and N. Likewise preferred heteroaromatic radicals comprise 1 heteroatom as ring member, which is selected from O, S and N, and optionally 1, 2 or 3 further nitrogen atoms as ring members. Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadiazolyl, [1,3,4]-oxadizolyl, 4- or 5-[1,2,3]-thiadiazolyl, [1,2,5]-thiadiazolyl, 3- or 5-[1,2,4]-thiadizolyl or [1,3,4]-thiadiazolyl, which may be unsubstituted or which may carry 1, 2 or 3 of the aforementioned radicals $R^a$ and/or $R^b$.

Preferably, Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members which may be unsubstituted or which may carry 1, 2 or 3 of the aforementioned radicals $R^a$ and/or $R^b$. Amongst these heteroaromatic radicals those are preferred, which comprise 1, 2 or 3 nitrogen atoms and no further heteroatom as ring members, or 1 or 2 nitrogen atoms and 1 atom, selected from O and S, as ring members. However, thienyl and furyl are likewise preferred. Particularly preferred radicals Ar are 2- or 3-thienyl, 2-, 3- or 4-pyridyl, 2-, 4- or 5-pyrimidinyl, 2-, 3- or 5-thiazolyl, 1,2,4-triazol-3-yl, 1,2,3-triazol-4-yl, 1,3,4-thiadiazol-2-yl, in particular 2-thienyl, 2-pyrimidinyl, 5-pyrimidinyl, 2-pyridinyl and more particularly phenyl which may be unsubstituted or which may carry 1, 2 or 3 of the aforementioned radicals $R^a$ and/or $R^b$.

A skilled person will appreciate that the moiety -E-SO$_2$—Ar can be bound to any of the carbon atoms of the aromatic moiety, except for the bridgehead carbon atoms. Preferably the moiety -E-SO$_2$—Ar is located in the 2- or 3-position of the indane nucleus.

Preferably the aromatic radical Ar carries one radical $R^a$ and optionally one or two further radicals $R^b$ selected from methyl, fluorinated methyl, halogen, in particular fluorine or chlorine.

The aforementioned 5-membered heteroaromatic radicals Ar preferably one radical $R^a$ in the 3-position (related to the position of the SO$_2$-radical) and optionally one or two further radicals $R^b$, which are preferably selected from halogen, in particular fluorine or chlorine.

Phenyl and the aforementioned 6-membered heteroaromatic radicals Ar preferably carry one radical $R^a$ in the 4-position (related to the position of the SO$_2$-radical) and optionally one or two further radicals $R^b$, which are preferably selected from halogen, in particular fluorine or chlorine.

In a very preferred embodiment of the invention Ar is phenyl that carries a radical $R^a$ in the 4-position of the phenyl ring and optionally 1 or 2 further radicals $R^b$, which are preferably selected from halogen, in particular from fluorine or chlorine.

In another preferred embodiment of the invention Ar is 2-pyrimidinyl that carries a radical $R^a$ in the 5-position of the pyrimidine ring and optionally 1 or 2 further radicals $R^b$, which are preferably selected from halogen, in particular from fluorine or chlorine.

In a further preferred embodiment of the invention Ar is 5-pyrimidinyl that carries a radical $R^a$ in the 2-position of the pyrimidine ring and optionally 1 or 2 further radicals $R^b$, which are preferably selected from halogen, in particular from fluorine or chlorine.

In a further preferred embodiment of the invention Ar is 2-thienyl that carries a radical $R^a$ in the 3-position of the thiophene ring and optionally 1 or 2 further radicals $R^b$, which are preferably selected from halogen, in particular from fluorine or chlorine.

Preferably Ar carries 1 radical $R^a$ which is different from $CH_3$, $OCH_3$, $CF_3$, $OCF_3$, $NH_2$, $SO_2NH_2$, acetamido, $C_2$-$C_6$-alkoxy or acetyl.

In a preferred embodiment Ar carries 1 radical $R^a$ which selected from the group consisting of $C_2$-$C_6$-alkyl, $C_3$-$C_6$-cycloalkyl, $C_2$-$C_6$-alkoxy, fluorinated $C_2$-$C_6$-alkyl, fluorinated $C_3$-$C_6$-cycloalkyl, fluorinated $C_2$-$C_6$-alkoxy, $NR^4R^5$, 1-aziridinyl, azetidin-1-yl, pyrrolidin-1-yl or piperidin-1-yl, wherein the last four mentioned radicals may be fluorinated, a phenyl group and an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 radicals selected from Halogen and the radicals $R^a$, and wherein Ar may carry 1 or 2 further radicals $R^b$, which are independently from each other selected from halogen, cyano, methyl, fluoromethyl, difluoromethyl, trifluoromethyl, difluoromethoxy and trifluoromethoxy. In this embodiment $R^4$, $R^5$ are, independently of each other, preferably selected from H, $C_1$-$C_2$-alkyl and fluorinated $C_1$-$C_2$-alkyl. Preferably one of the radicals $R^4$ or $R^5$ is different from hydrogen. One of the radicals $R^4$ or $R^5$ may also be $C_1$-$C_2$-alkoxy.

In a very preferred embodiment, the radical Ar preferably carries one radical $R^a$, which has the formula $R^{a'}$

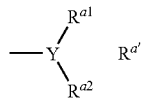

wherein
Y is N, CH or CF,
$R^{a1}$ and $R^{a2}$ are independently of each other selected from $C_1$-$C_2$-alkyl, $C_1$-$C_2$-alkoxy, fluorinanted $C_1$-$C_2$-alkyl, provided for Y being CH or CF one of the radicals $R^{a1}$ or $R^{a2}$ may also be hydrogen or fluorine, or
$R^{a1}$ and $R^2$ together form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6;
In particular
$R^{a1}$ and $R^{a2}$ are independently of each other selected from $C_1$-$C_2$-alkyl, in particular methyl, fluorinated $C_1$-$C_2$-alkyl, in particular fluoromethyl, difluoromethyl or trifluoromethyl, provided for Y being CH or CF one of the radicals $R^{a1}$ or $R^{a2}$ may also be hydrogen or fluorine, or
$R^{a1}$ and $R^{a2}$ form a radical $(CH_2)_m$ wherein 1 or 2 of the hydrogen atoms may be replaced by fluorine and wherein m is 2, 3 or 4, in particular $CH_2$—$CH_2$, $CHF$—$CH_2$ $CF_2$—$CH_2$, $CH_2$—$CH_2$—$CH_2$, $CHF$—$CH_2$—$CH_2$, $CF_2$—$CH_2$—$CH_2$, $CH_2$—$CHF$—$CH_2$, $CH_2$—$CF_2$—$CH_2$.

In case $R^{a1}$ and $R^{a2}$ are different from each other, the radical of the aforementioned formula $R^{a'}$ may have either (R)- or (S)-configuration with regard to the Y-moiety.

Examples for preferred radicals of the formula $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-fluoro-1-methylethyl cyclopropyl, cyclobutyl, 1-fluorocyclopropyl, 2,2-difluorocyclopropyl and 2-fluorocyclopropyl.

Also preferred are radicals $R^{a'}$ wherein one of $R^{a1}$ or $R^{a2}$ is $C_1$-$C_2$-alkoxy and the other other of $R^{a1}$ or $R^{a2}$ is selected from H, $C_1$-$C_2$-alkyl, in particular methyl, fluorinated $C_1$-$C_2$-alkyl, in particular fluoromethyl, difluoromethyl or trifluoromethyl. Examples comprise N-methoxy-N-methylamino, N-methoxyamino and N-ethoxyamino.

Preferred radicals of the formula $R^{a'}$ also comprise those wherein Y is nitrogen and wherein $R^{a1}$ and $R^{a2}$ form a radical $(CH_2)_m$ wherein 1 or 2 of the hydrogen atoms may be replaced by fluorine, methyl, trifluoromethyl, methoxy or oxo and wherein m is 2, 3, 4 or 5. Examples comprise azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, piperidin-1-yl, 2-methylpiperidin-1-yl, (S)-2-methylpiperidin-1-yl and (R)-2-methylpiperidin-1-yl.

Likewise preferred are radicals $R^{a'}$, wherein $R^{a1}$ and $R^{a2}$ together form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety is replaced by O, S, S=O, $SO_2$ or N—$R^c$, $R^c$ being hydrogen or $C_1$-$C_2$-alkyl and wherein m is 2, 3, 4, 5 or 6. Examples for preferred radicals of the formula $R''$ also comprise 4-morpholinyl, 4-thiomorpholinyl, 4-(1,1-dioxo)thiomorpholinyl, piperazin-1-yl, 4-methylpiperazin-1-yl, 2-oxo-oxazolidin-3-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl and (R)-1-methylpyrrolidin-3-yl.

Amongst the radicals of the formula $R^{a'}$ those are preferred which carry 1, 2, 3 or 4, in particular 1, 2 or 3 fluorine atoms.

In a further preferred embodiment Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl. Amongst these radicals $R^a$, preference is given to radicals selected from 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadizolyl, [1,3,4]-oxadizolyl, 4- or 5-[1,2,3]-thiadizolyl, [1,2,5]-thiadiazolyl, 3- or 5-[1,2,4]-thiadizolyl or [1,3,4]-thiadiazolyl, in particular from 2- or 3-furanyl, 2- or 3-thienyl, 1-, 2- or 3-pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents as given above. Preferred substituents on heteroaromatic $R^a$ are selected from halogen, $C_1$-$C_4$-alkyl, $C_1$-$C_4$-alkoxy, fluorinated $C_1$-$C_4$-alkyl and fluorinated $C_1$-$C_4$-alkoxy.

In a further preferred embodiment Ar carries 1 radical $R^a$ which selected from the group consisting of $CHF_2$, $CH_2F$, $OCHF_2$ and $OCH_2F$, with $OCHF_2$ being preferred. In this embodiment Ar may also carry 1 or 2 further radicals $R^b$, which are independently from each other selected from halogen, cyano, methyl, fluoromethyl, difluoromethyl, trifluoromethyl, difluoromethoxy and trifluoromethoxy. Preferably Ar carries no further radical $R^b$. In this embodiment Ar is preferably phenyl which carries 1 radical $R^a$ which selected from the group consisting of $CHF_2$, $CH_2F$, $OCHF_2$ and $OCH_2F$, with $OCHF_2$ being preferred. In this embodiment Ar is preferably phenyl, which carries $R^a$ in the 4 position with respect to the $SO_2$-group.

In another embodiment of the invention, Ar carries 1 radical $R^a$ which selected from the group consisting of $C_2$-$C_6$-alkenyl, fluorinated $C_2$-$C_6$-alkenyl, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $CH_2NR^4R^5$, $ONR^4R^5$, NHC(O)$NR^4R^5$, C(O)$NR^4R^5$, $SO_2NR^4R^5$, $C_1$-$C_6$-alkylcarbonyl, fluorinated $C_2$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenoxy, benzyloxy and a 5- or 6-membered N-bound heteroaromatic radical, wherein the four last mentioned radicals may carry 1, 2, 3 or 4 radicals selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

In another embodiment of the invention, Ar is phenyl, which carries 1 radical $R^a$ and at least one radical $R^b$ and wherein $R^a$ and one radical $R^b$ are bound to two adjacent carbon atoms of phenyl and form a 5- or 6-membered heterocyclic or carbocyclic ring which is fused to the phenyl ring and which is unsubstituted or which may carry 1, 2 or 3 radicals as given above. Examples of a phenyl ring fused to a saturated or unsaturated 5- or 6-membered carbocyclic or heterocyclic ring comprise indenyl, indanyl, naphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals. Preferred substituents for the saturated or unsaturated 5- or 6-membered carbocyclic or heterocyclic ring fused to the phenyl ring are selected from halogen, $C_1$-$C_4$-alkyl, $C_1$-$C_4$-alkoxy, fluorinated $C_1$-$C_4$-alkyl and fluorinated $C_1$-$C_4$-alkoxy. The radical $R^1$ is preferably $C_2$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl, in particular $C_2$-$C_4$-alkyl, $C_3$-$C_4$-cycloalkyl, $C_3$-$C_4$-alkenyl, fluorinated $C_1$-$C_4$-alkyl, fluorinated $C_3$-$C_4$-cycloalkyl, more preferably n-propyl, fluorinated linear $C_2$-$C_3$-alkyl or 1-propen-3-yl, in particular n-propyl or 1-propen-3-yl.

One preferred embodiment of the invention relates to compounds of the formula I, wherein X is CH. Another embodiment of the invention, relates to compounds of the formula I, wherein X is N.

Preferably the moiety E is N—$R^3$, wherein $R^3$ is as defined above. $R^3$ is in particular H or methyl and most preferred H.

One preferred embodiment of the invention relates to compounds, wherein $R^{1a}$ is hydrogen and $R^2$ and $R^{2a}$ have the meanings given above. In particular $R^2$ and/or $R^{2a}$ is (are) also hydrogen. For $R^2$ or $R^{2a}$ being different from hydrogen the radicals $R^2$ (or $R^{2a}$) and $NR^1R^{1a}$ may be located cis- or trans.

Another preferred embodiment of the invention relates to compounds, wherein $R^{1a}$ and $R^2$ or $R^{1a}$ and $R^{2a}$ together form a moiety $(CH_2)_n$, wherein n is as defined above and in particular 2 or 3. Thereby a fused ring is formed, which may be trans-fused or cis-fused.

The carbon atom of the (aza)indane core that carries the radical $NR^1R^{1a}$ may have (R) or (S) configuration.

Particularly preferred are compounds of the formula I, wherein $R^2$ and $R^{2a}$ are hydrogen and E is NH. These compounds are hereinafter referred to as compounds Ia (X=CH) and compounds Ib (X=N). Thus a particular preferred object of the invention are compounds of the formulae Ia and Ib and the pharmaceutically acceptable salts thereof:

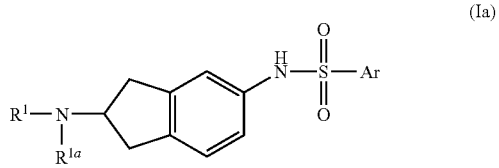

(Ia)

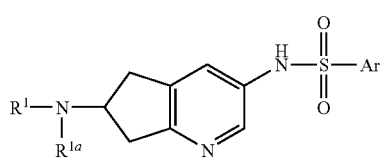

(Ib)

including their S-enantiomers (compounds S-Ia and S-Ib), their R-enantiomers (R-Ia and R-1b) and mixtures of S- and R-enantiomers (R/S-Ia and R/S-Ib). In formulae Ia and Ib, $R^{1a}$, $R^1$ and $R^2$ have the meanings as given above. $R^{1a}$ is preferably hydrogen.

Examples of preferred compounds of the formula I are given in the following tables A-1 and A-2

Table A-1
Compounds of the formulae S-Ia, R-Ia and S/R-Ia, wherein $R^1$ and Ar have the meanings given in one row of table A.

Table A-2
Compounds of the formulae S-Ib, R-Ib and S/R-Ib, wherein $R^{1a}$ is hydrogen and $R^1$ and Ar have the meanings given in one row of table A.

A further embodiment of the invention relates to compounds of the formula I, wherein $R^{1a}$ and $R^2$ together are 1,3-propandiyl, $R^{2a}$ is hydrogen and E is NH. These compounds are hereinafter referred to as compounds Ic (X=CH) and compounds Id (X=N). Examples of compounds of the formulae Ic and Id are given in the following tables A-3 and A-4

Table A-3
Compounds of the formula Ic, wherein $R^1$ and Ar have the meanings given in one row of table A.

Table A-4
Compounds of the formula Id, wherein $R^{1a}$ is hydrogen and $R^1$ and Ar have the meanings given in one row of table A.

TABLE A

| No. | $R^1$ | Ar |
|---|---|---|
| 1. | propyl | 4-ethylphenyl |
| 2. | propyl | 4-propylphenyl |
| 3. | propyl | 4-isopropylphenyl |
| 4. | propyl | 4-sec-butylphenyl |
| 5. | propyl | 4-isobutylphenyl |
| 6. | propyl | 4-(1,1-dimethylpropyl)-phenyl |
| 7. | propyl | 4-vinylphenyl |
| 8. | propyl | 4-isopropenylphenyl |
| 9. | propyl | 4-(fluoromethyl)phenyl |
| 10. | propyl | 3-(fluoromethyl)phenyl |
| 11. | propyl | 2-(fluoromethyl)phenyl |
| 12. | propyl | 4-(difluoromethyl)phenyl |
| 13. | propyl | 3-(difluoromethyl)phenyl |
| 14. | propyl | 2-(difluoromethyl)phenyl |
| 15. | propyl | 4-(trifluoromethyl)phenyl |
| 16. | propyl | 3-(trifluoromethyl)phenyl |
| 17. | propyl | 2-(trifluoromethyl)phenyl |
| 18. | propyl | 4-(1-fluoroethyl)-phenyl |
| 19. | propyl | 4-((S)-1-fluoroethyl)-phenyl |
| 20. | propyl | 4-((R)-1-fluoroethyl)-phenyl |
| 21. | propyl | 4-(2-fluoroethyl)-phenyl |
| 22. | propyl | 4-(1,1-difluoroethyl)-phenyl |
| 23. | propyl | 4-(2,2-difluoroethyl)-phenyl |
| 24. | propyl | 4-(2,2,2-trifluoroethyl)-phenyl |
| 25. | propyl | 4-(3-fluoropropyl)-phenyl |
| 26. | propyl | 4-(2-fluoropropyl)-phenyl |
| 27. | propyl | 4-((S)-2-fluoropropyl)-phenyl |
| 28. | propyl | 4-((R)-2-fluoropropyl)-phenyl |
| 29. | propyl | 4-(3,3-difluoropropyl)-phenyl |
| 30. | propyl | 4-(3,3,3-trifluoropropyl)-phenyl |
| 31. | propyl | 4-(1-fluoro-1-methylethyl)-phenyl |
| 32. | propyl | 4-(2-fluoro-1-methylethyl)-phenyl |
| 33. | propyl | 4-((S)-2-fluoro-1-methylethyl)-phenyl |
| 34. | propyl | 4-((R)-2-fluoro-1-methylethyl)-phenyl |
| 35. | propyl | 4-(2,2-difluoro-1-methylethyl)-phenyl |
| 36. | propyl | 4-((S)-2,2-difluoro-1-methylethyl)-phenyl |
| 37. | propyl | 4-((R)-2,2-difluoro-1-methylethyl)-phenyl |
| 38. | propyl | 4-(2,2,2-trifluoro-1-methylethyl)-phenyl |
| 39. | propyl | 4-((S)-2,2,2-trifluoro-1-methylethyl)-phenyl |
| 40. | propyl | 4-((R)-2,2,2-trifluoro-1-methylethyl)-phenyl |
| 41. | propyl | 4-(2-fluoro-1-fluoromethylethyl)-phenyl |
| 42. | propyl | 4-(1-difluoromethyl-2,2-difluoroethyl)-phenyl |
| 43. | propyl | 4-(1,1-dimethyl-2-fluoroethyl)-phenyl |
| 44. | propyl | 4-ethoxyphenyl |
| 45. | propyl | 4-propoxyphenyl |
| 46. | propyl | 4-isopropoxyphenyl |
| 47. | propyl | 4-butoxyphenyl |
| 48. | propyl | 4-(fluoromethoxy)-phenyl |
| 49. | propyl | 4-(difluoromethoxy)-phenyl |
| 50. | propyl | 4-(2-fluoroethoxy)-phenyl |

TABLE A-continued

| No. | R¹ | Ar |
|---|---|---|
| 51. | propyl | 4-(2,2-difluoroethoxy)-phenyl |
| 52. | propyl | 4-(2,2,2-trifluoroethoxy)-phenyl |
| 53. | propyl | 4-(1,1,2,2-tetrafluoroethoxy)-phenyl |
| 54. | propyl | 4-cyclopropylphenyl |
| 55. | propyl | 4-cyclobutylphenyl |
| 56. | propyl | 4-cyclopentylphenyl |
| 57. | propyl | 4-(2,2-difluorocyclopropyl)-phenyl |
| 58. | propyl | 2-fluoro-4-isopropylphenyl |
| 59. | propyl | 3-fluoro-4-isopropylphenyl |
| 60. | propyl | 4-(1-hydroxy-1-methylethyl)-phenyl |
| 61. | propyl | 4-(2-hydroxy-2-methylpropyl)-phenyl |
| 62. | propyl | 4-acetylphenyl |
| 63. | propyl | 4-carboxyphenyl |
| 64. | propyl | 4-(O-benzyl)-phenyl |
| 65. | propyl | 4-(2-methoxyethoxy)-phenyl |
| 66. | propyl | 4-($CH_2$—$N(CH_3)_2$)-phenyl |
| 67. | propyl | 4-(NH—CO—$NH_2$)-phenyl |
| 68. | propyl | 4-(methylsulfanyl)-phenyl |
| 69. | propyl | 4-(fluoromethylsulfanyl)-phenyl |
| 70. | propyl | 4-(difluoromethylsulfanyl)-phenyl |
| 71. | propyl | 4-(trifluoromethylsulfanyl)-phenyl |
| 72. | propyl | 4-(methylsulfonyl)-phenyl |
| 73. | propyl | 4-(N-methoxy-N-methyl-amino)-phenyl |
| 74. | propyl | 4-(methoxyamino)-phenyl |
| 75. | propyl | 4-(ethoxyamino)-phenyl |
| 76. | propyl | 4-(N-methylaminooxy)-phenyl |
| 77. | propyl | 4-(N,N-dimethylaminooxy)-phenyl |
| 78. | propyl | 4-(azetidin-1-yl)-phenyl |
| 79. | propyl | 4-(2-methylazetidin-1-yl)-phenyl |
| 80. | propyl | 4-((S)-2-methylazetidin-1-yl)-phenyl |
| 81. | propyl | 4-((R)-2-methylazetidin-1-yl)-phenyl |
| 82. | propyl | 4-(3-fluoroazetidin-1-yl)-phenyl |
| 83. | propyl | 4-(3-methoxyazetidin-1-yl)-phenyl |
| 84. | propyl | 4-(3-hydroxyazetidin-1-yl)-phenyl |
| 85. | propyl | 4-(pyrrolidin-1-yl)-phenyl |
| 86. | propyl | 4-(pyrrolidin-2-yl)-phenyl |
| 87. | propyl | 4-((S)-pyrrolidin-2-yl)-phenyl |
| 88. | propyl | 4-((R)-pyrrolidin-2-yl)-phenyl |
| 89. | propyl | 4-(pyrrolidin-3-yl)-phenyl |
| 90. | propyl | 4-((S)-pyrrolidin-3-yl)-phenyl |
| 91. | propyl | 4-((R)-pyrrolidin-3-yl)-phenyl |
| 92. | propyl | 4-(2-fluoropyrrolidin-1-yl)-phenyl |
| 93. | propyl | 4-((S)-2-fluoropyrrolidin-1-yl)-phenyl |
| 94. | propyl | 4-((R)-2-fluoropyrrolidin-1-yl)-phenyl |
| 95. | propyl | 4-(3-fluoropyrrolidin-1-yl)-phenyl |
| 96. | propyl | 4-((S)-3-fluoropyrrolidin-1-yl)-phenyl |
| 97. | propyl | 4-((R)-3-fluoropyrrolidin-1-yl)-phenyl |
| 98. | propyl | 4-(2,2-difluoropyrrolidin-1-yl)-phenyl |
| 99. | propyl | 4-(3,3-difluoropyrrolidin-1-yl)-phenyl |
| 100. | propyl | 4-(2-methylpyrrolidin-1-yl)-phenyl |
| 101. | propyl | 4-((S)-2-methylpyrrolidin-1-yl)-phenyl |
| 102. | propyl | 4-((R)-2-methylpyrrolidin-1-yl)-phenyl |
| 103. | propyl | 4-(3-methylpyrrolidin-1-yl)-phenyl |
| 104. | propyl | 4-((S)-3-methylpyrrolidin-1-yl)-phenyl |
| 105. | propyl | 4-((R)-3-methylpyrrolidin-1-yl)-phenyl |
| 106. | propyl | 4-(1-methylpyrrolidin-2-yl)-phenyl |
| 107. | propyl | 4-((S)-1-methylpyrrolidin-2-yl)-phenyl |
| 108. | propyl | 4-((R)-1-methylpyrrolidin-2-yl)-phenyl |
| 109. | propyl | 4-(1-methylpyrrolidin-3-yl)-phenyl |
| 110. | propyl | 4-((S)-1-methylpyrrolidin-3-yl)-phenyl |
| 111. | propyl | 4-((R)-1-methylpyrrolidin-3-yl)-phenyl |
| 112. | propyl | 4-(2,2-dimethylpyrrolidin-1-yl)-phenyl |
| 113. | propyl | 4-(3,3-dimethylpyrrolidin-1-yl)-phenyl |
| 114. | propyl | 4-(2-trifluoromethylpyrrolidin-1-yl)-phenyl |
| 115. | propyl | 4-((S)-2-trifluoromethylpyrrolidin-1-yl)-phenyl |
| 116. | propyl | 4-((R)-2-trifluoromethylpyrrolidin-1-yl)-phenyl |
| 117. | propyl | 4-(3-trifluoromethylpyrrolidin-1-yl)-phenyl |
| 118. | propyl | 4-((S)-3-trifluoromethylpyrrolidin-1-yl)-phenyl |
| 119. | propyl | 4-((R)-3-trifluoromethylpyrrolidin-1-yl)-phenyl |
| 120. | propyl | 4-(2-oxopyrrolidin-1-yl)-phenyl |
| 121. | propyl | 4-(2-oxo-oxazolidin-3-yl)-phenyl |
| 122. | propyl | 4-(piperidin-1-yl)-phenyl |
| 123. | propyl | 4-(2-methylpiperidin-1-yl)-phenyl |
| 124. | propyl | 4-((S)-2-methylpiperidin-1-yl)-phenyl |
| 125. | propyl | 4-((R)-2-methylpiperidin-1-yl)-phenyl |
| 126. | propyl | 4-(piperazin-1-yl)-phenyl |
| 127. | propyl | 4-(4-methylpiperazin-1-yl)-phenyl |

TABLE A-continued

| No. | R¹ | Ar |
|---|---|---|
| 128. | propyl | 4-(morpholin-4-yl)-phenyl |
| 129. | propyl | 4-(thiomorpholin-4-yl)-phenyl |
| 130. | propyl | 4-(1-oxo-thiomorpholin-4-yl)-phenyl |
| 131. | propyl | 4-(1,1-dioxo-thiomorpholin-4-yl)-phenyl |
| 132. | propyl | 4-(pyrrol-1-yl)-phenyl |
| 133. | propyl | 4-(pyrrol-2-yl)-phenyl |
| 134. | propyl | 4-(pyrrol-3-yl)-phenyl |
| 135. | propyl | 4-(1-methylpyrrol-2-yl)-phenyl |
| 136. | propyl | 4-(1-methylpyrrol-3-yl)-phenyl |
| 137. | propyl | 4-(furan-2-yl)-phenyl |
| 138. | propyl | 4-(furan-3-yl)-phenyl |
| 139. | propyl | 4-(thiophen-2-yl)-phenyl |
| 140. | propyl | 4-(thiophen-3-yl)-phenyl |
| 141. | propyl | 4-(5-propylthien-2-yl)-phenyl |
| 142. | propyl | 4-(pyrazol-1-yl)-phenyl |
| 143. | propyl | 4-(pyrazol-3-yl)-phenyl |
| 144. | propyl | 4-(pyrazol-4-yl)-phenyl |
| 145. | propyl | 4-(1-methyl-1H-pyrazol-4-yl)-phenyl |
| 146. | propyl | 4-(1-ethyl-1H-pyrazol-4-yl)-phenyl |
| 147. | propyl | 4-(1-methyl-1H-pyrazol-5-yl)-phenyl |
| 148. | propyl | 4-(1H-imidazol-2-yl)-phenyl |
| 149. | propyl | 4-(imidazol-1-yl)-phenyl |
| 150. | propyl | 4-(1-methylimidazol-2-yl)-phenyl |
| 151. | propyl | 4-(oxazol-2-yl)-phenyl |
| 152. | propyl | 4-(oxazol-4-yl)-phenyl |
| 153. | propyl | 4-(oxazol-5-yl)-phenyl |
| 154. | propyl | 4-(isoxazol-3-yl)-phenyl |
| 155. | propyl | 4-(isoxazol-4-yl)-phenyl |
| 156. | propyl | 4-(isoxazol-5-yl)-phenyl |
| 157. | propyl | 4-([1,2,3]-triazol-1-yl)-phenyl |
| 158. | propyl | 4-([1,2,4]-triazol-1-yl)-phenyl |
| 159. | propyl | 4-([1,2,3]-triazol-2-yl)-phenyl |
| 160. | propyl | 4-(4H-[1,2,4]-triazol-3-yl)-phenyl |
| 161. | propyl | 4-([1,2,4]-triazol-4-yl)-phenyl |
| 162. | propyl | 4-(2H-[1,2,3]-triazol-4-yl)-phenyl |
| 163. | propyl | 4-(4-methyl-4H-[1,2,4]-triazol-3-yl)-phenyl |
| 164. | propyl | 4-(2-methyl-2H-[1,2,3]-triazol-4-yl)-phenyl |
| 165. | propyl | 4-([1,3,4]-oxadiazol-2-yl)-phenyl |
| 166. | propyl | 4-([1,2,4]-oxadiazol-3-yl)-phenyl |
| 167. | propyl | 4-([1,2,4]-oxadiazol-5-yl)-phenyl |
| 168. | propyl | 4-([1,2,3]-oxadiazol-4-yl)-phenyl |
| 169. | propyl | 4-([1,2,3]-oxadiazol-5-yl)-phenyl |
| 170. | propyl | 4-([1,2,3]-thiadiazol-4-yl)-phenyl |
| 171. | propyl | 4-(1H-tetrazol-5-yl)-phenyl |
| 172. | propyl | 4-(tetrazol-1-yl)-phenyl |
| 173. | propyl | 4-(2-methyl-2H-tetrazol-5-yl)-phenyl |
| 174. | propyl | 4-(1-methyl-1H-tetrazol-5-yl)-phenyl |
| 175. | propyl | 4-furazan-3-yl-phenyl |
| 176. | propyl | 4-(pyrid-2-yl)-phenyl |
| 177. | propyl | 4-(pyrid-3-yl)-phenyl |
| 178. | propyl | 4-(pyrid-4-yl)-phenyl |
| 179. | propyl | 4-(pyrimidin-2-yl)-phenyl |
| 180. | propyl | 4-(pyrimidin-4-yl)-phenyl |
| 181. | propyl | 4-(pyrimidin-5-yl)-phenyl |
| 182. | propyl | 5-isopropylthiophen-2-yl |
| 183. | propyl | 2-chlorothiophen-5-yl |
| 184. | propyl | 2,5-dichlorothiophen-4-yl |
| 185. | propyl | 2,3-dichlorothiophen-5-yl |
| 186. | propyl | 2-chloro-3-nitrothiophen-5-yl |
| 187. | propyl | 2-(phenylsulfonyl)-thiophen-5-yl |
| 188. | propyl | 2-(pyridin-2-yl)thiophen-5-yl |
| 189. | propyl | 2-(5-(trifluoromethyl)isoxazol-3-yl)-thiophen-5-yl |
| 190. | propyl | 2-(2-methylthiazol-4-yl)-thiophen-5-yl |
| 191. | propyl | 1-methyl-1H-imidazol-4-yl |
| 192. | propyl | 1,2-dimethyl-1H-imidazol-4-yl |
| 193. | propyl | 3,5-dimethylisoxazol-4-yl |
| 194. | propyl | thiazol-2-yl |
| 195. | propyl | 4-methylthiazol-2-yl |
| 196. | propyl | 4-isopropylthiazol-2-yl |
| 197. | propyl | 4-trifluoromethylthiazol-2-yl |
| 198. | propyl | 5-methylthiazol-2-yl |
| 199. | propyl | 5-isopropylthiazol-2-yl |
| 200. | propyl | 5-trifluoromethylthiazol-2-yl |
| 201. | propyl | 2,4-dimethylthiazol-5-yl |
| 202. | propyl | 2-acetamido-4-methylthiazol-5-yl |
| 203. | propyl | 4H-[1,2,4]triazol-3-yl |
| 204. | propyl | 5-methyl-4H-[1,2,4]triazol-3-yl |

TABLE A-continued

| No. | R¹ | Ar |
|---|---|---|
| 205. | propyl | 4-methyl-4H-[1,2,4]triazol-3-yl |
| 206. | propyl | 5-isopropyl-4H-[1,2,4]triazol-3-yl |
| 207. | propyl | 5-trifluoromethyl-4H-[1,2,4]triazol-3-yl |
| 208. | propyl | 4,5-dimethyl-4H-[1,2,4]triazol-3-yl |
| 209. | propyl | 5-isopropyl-4-methyl-4H-[1,2,4]triazol-3-yl |
| 210. | propyl | 5-trifluoromethyl-4-methyl-4H-[1,2,4]triazol-3-yl |
| 211. | propyl | [1,3,4]thiadiazol-2-yl |
| 212. | propyl | 5-methyl-[1,3,4]thiadiazol-2-yl |
| 213. | propyl | 5-isopropyl-[1,3,4]thiadiazol-2-yl |
| 214. | propyl | 5-trifluoromethyl-[1,3,4]thiadiazol-2-yl |
| 215. | propyl | 3-bromo-2-chloropyrid-5-yl |
| 216. | propyl | 2-(4-morpholino)-pyrid-5-yl |
| 217. | propyl | 2-phenoxypyrid-5-yl |
| 218. | propyl | (2-isopropyl)-pyrimidin-5-yl |
| 219. | propyl | (5-isopropyl)-pyrimidin-2-yl |
| 220. | propyl | 8-quinolyl |
| 221. | propyl | 5-isoquinolyl |
| 222. | propyl | 2-(2,2,2-trifluoroacetyl)-1,2,3,4-tetrahydroisoquinolin-7-yl |
| 223. | propyl | 5-chloro-3-methylbenzothiophen-2-yl |
| 224. | propyl | 3,4-dihydro-4-methyl-2H-benzo[b][1,4]oxazinyl |
| 225. | propyl | benzothiazol-6-yl |
| 226. | propyl | benzo[2,1,3]oxadiazol-4-yl |
| 227. | propyl | 5-chlorobenzo[1,2,5]oxadiazolyl |
| 228. | propyl | 7-chlorobenzo[2,1,3]oxadiazol-4-yl |
| 229. | propyl | benzo[2,1,3]thiadiazol-4-yl |
| 230. | ethyl | 4-propylphenyl |
| 231. | ethyl | 4-ethylphenyl |
| 232. | ethyl | 4-isopropylphenyl |
| 233. | ethyl | 4-sec-butylphenyl |
| 234. | ethyl | 4-isobutylphenyl |
| 235. | ethyl | 4-(1,1-dimethylpropyl)-phenyl |
| 236. | ethyl | 4-vinylphenyl |
| 237. | ethyl | 4-isopropenylphenyl |
| 238. | ethyl | 4-(fluoromethyl)phenyl |
| 239. | ethyl | 3-(fluoromethyl)phenyl |
| 240. | ethyl | 2-(fluoromethyl)phenyl |
| 241. | ethyl | 4-(difluoromethyl)phenyl |
| 242. | ethyl | 3-(difluoromethyl)phenyl |
| 243. | ethyl | 2-(difluoromethyl)phenyl |
| 244. | ethyl | 4-(trifluoromethyl)phenyl |
| 245. | ethyl | 3-(trifluoromethyl)phenyl |
| 246. | ethyl | 2-(trifluoromethyl)phenyl |
| 247. | ethyl | 4-(1-fluoroethyl)-phenyl |
| 248. | ethyl | 4-((S)-1-fluoroethyl)-phenyl |
| 249. | ethyl | 4-((R)-1-fluoroethyl)-phenyl |
| 250. | ethyl | 4-(2-fluoroethyl)-phenyl |
| 251. | ethyl | 4-(1,1-difluoroethyl)-phenyl |
| 252. | ethyl | 4-(2,2-difluoroethyl)-phenyl |
| 253. | ethyl | 4-(2,2,2-trifluoroethyl)-phenyl |
| 254. | ethyl | 4-(3-fluoropropyl)-phenyl |
| 255. | ethyl | 4-(2-fluoropropyl)-phenyl |
| 256. | ethyl | 4-((S)-2-fluoropropyl)-phenyl |
| 257. | ethyl | 4-((R)-2-fluoropropyl)-phenyl |
| 258. | ethyl | 4-(3,3-difluoropropyl)-phenyl |
| 259. | ethyl | 4-(3,3,3-trifluoropropyl)-phenyl |
| 260. | ethyl | 4-(1-fluoro-1-methylethyl)-phenyl |
| 261. | ethyl | 4-(2-fluoro-1-methylethyl)-phenyl |
| 262. | ethyl | 4-((S)-2-fluoro-1-methylethyl)-phenyl |
| 263. | ethyl | 4-((R)-2-fluoro-1-methylethyl)-phenyl |
| 264. | ethyl | 4-(2,2-difluoro-1-methylethyl)-phenyl |
| 265. | ethyl | 4-((S)-2,2-difluoro-1-methylethyl)-phenyl |
| 266. | ethyl | 4-((R)-2,2-difluoro-1-methylethyl)-phenyl |
| 267. | ethyl | 4-(2,2,2-trifluoro-1-methylethyl)-phenyl |
| 268. | ethyl | 4-((S)-2,2,2-trifluoro-1-methylethyl)-phenyl |
| 269. | ethyl | 4-((R)-2,2,2-trifluoro-1-methylethyl)-phenyl |
| 270. | ethyl | 4-(2-fluoro-1-fluoromethylethyl)-phenyl |
| 271. | ethyl | 4-(1-difluoromethyl-2,2-difluoroethyl)-phenyl |
| 272. | ethyl | 4-(1,1-dimethyl-2-fluoroethyl)-phenyl |
| 273. | ethyl | 4-ethoxyphenyl |
| 274. | ethyl | 4-propoxyphenyl |
| 275. | ethyl | 4-isopropoxyphenyl |
| 276. | ethyl | 4-butoxyphenyl |
| 277. | ethyl | 4-(fluoromethoxy)-phenyl |
| 278. | ethyl | 4-(difluoromethoxy)-phenyl |
| 279. | ethyl | 4-(2-fluoroethoxy)-phenyl |
| 280. | ethyl | 4-(2,2-difluoroethoxy)-phenyl |

TABLE A-continued

| No. | R¹ | Ar |
|---|---|---|
| 281. | ethyl | 4-(2,2,2-trifluoroethoxy)-phenyl |
| 282. | ethyl | 4-(1,1,2,2-tetrafluoroethoxy)-phenyl |
| 283. | ethyl | 4-cyclopropylphenyl |
| 284. | ethyl | 4-cyclobutylphenyl |
| 285. | ethyl | 4-cyclopentylphenyl |
| 286. | ethyl | 4-(2,2-difluorocyclopropyl)-phenyl |
| 287. | ethyl | 2-fluoro-4-isopropylphenyl |
| 288. | ethyl | 3-fluoro-4-isopropylphenyl |
| 289. | ethyl | 4-(1-hydroxy-1-methylethyl)-phenyl |
| 290. | ethyl | 4-(2-hydroxy-2-methylpropyl)-phenyl |
| 291. | ethyl | 4-acetylphenyl |
| 292. | ethyl | 4-carboxyphenyl |
| 293. | ethyl | 4-(O-benzyl)-phenyl |
| 294. | ethyl | 4-(2-methoxyethoxy)-phenyl |
| 295. | ethyl | 4-($CH_2$—$N(CH_3)_2$)-phenyl |
| 296. | ethyl | 4-(NH—CO—$NH_2$)-phenyl |
| 297. | ethyl | 4-(methylsulfanyl)-phenyl |
| 298. | ethyl | 4-(fluoromethylsulfanyl)-phenyl |
| 299. | ethyl | 4-(difluoromethylsulfanyl)-phenyl |
| 300. | ethyl | 4-(trifluoromethylsulfanyl)-phenyl |
| 301. | ethyl | 4-(methylsulfonyl)-phenyl |
| 302. | ethyl | 4-(N-methoxy-N-methyl-amino)-phenyl |
| 303. | ethyl | 4-(methoxyamino)-phenyl |
| 304. | ethyl | 4-(ethoxyamino)-phenyl |
| 305. | ethyl | 4-(N-methylaminooxy)-phenyl |
| 306. | ethyl | 4-(N,N-dimethylaminooxy)-phenyl |
| 307. | ethyl | 4-(azetidin-1-yl)-phenyl |
| 308. | ethyl | 4-(2-methylazetidin-1-yl)-phenyl |
| 309. | ethyl | 4-((S)-2-methylazetidin-1-yl)-phenyl |
| 310. | ethyl | 4-((R)-2-methylazetidin-1-yl)-phenyl |
| 311. | ethyl | 4-(3-fluoroazetidin-1-yl)-phenyl |
| 312. | ethyl | 4-(3-methoxyazetidin-1-yl)-phenyl |
| 313. | ethyl | 4-(3-hydroxyazetidin-1-yl)-phenyl |
| 314. | ethyl | 4-(pyrrolidin-1-yl)-phenyl |
| 315. | ethyl | 4-(pyrrolidin-2-yl)-phenyl |
| 316. | ethyl | 4-((S)-pyrrolidin-2-yl)-phenyl |
| 317. | ethyl | 4-((R)-pyrrolidin-2-yl)-phenyl |
| 318. | ethyl | 4-(pyrrolidin-3-yl)-phenyl |
| 319. | ethyl | 4-((S)-pyrrolidin-3-yl)-phenyl |
| 320. | ethyl | 4-((R)-pyrrolidin-3-yl)-phenyl |
| 321. | ethyl | 4-(2-fluoropyrrolidin-1-yl)-phenyl |
| 322. | ethyl | 4-((S)-2-fluoropyrrolidin-1-yl)-phenyl |
| 323. | ethyl | 4-((R)-2-fluoropyrrolidin-1-yl)-phenyl |
| 324. | ethyl | 4-(3-fluoropyrrolidin-1-yl)-phenyl |
| 325. | ethyl | 4-((S)-3-fluoropyrrolidin-1-yl)-phenyl |
| 326. | ethyl | 4-((R)-3-fluoropyrrolidin-1-yl)-phenyl |
| 327. | ethyl | 4-(2,2-difluoropyrrolidin-1-yl)-phenyl |
| 328. | ethyl | 4-(3,3-difluoropyrrolidin-1-yl)-phenyl |
| 329. | ethyl | 4-(2-methylpyrrolidin-1-yl)-phenyl |
| 330. | ethyl | 4-((S)-2-methylpyrrolidin-1-yl)-phenyl |
| 331. | ethyl | 4-((R)-2-methylpyrrolidin-1-yl)-phenyl |
| 332. | ethyl | 4-(3-methylpyrrolidin-1-yl)-phenyl |
| 333. | ethyl | 4-((S)-3-methylpyrrolidin-1-yl)-phenyl |
| 334. | ethyl | 4-((R)-3-methylpyrrolidin-1-yl)-phenyl |
| 335. | ethyl | 4-(1-methylpyrrolidin-2-yl)-phenyl |
| 336. | ethyl | 4-((S)-1-methylpyrrolidin-2-yl)-phenyl |
| 337. | ethyl | 4-((R)-1-methylpyrrolidin-2-yl)-phenyl |
| 338. | ethyl | 4-(1-methylpyrrolidin-3-yl)-phenyl |
| 339. | ethyl | 4-((S)-1-methylpyrrolidin-3-yl)-phenyl |
| 340. | ethyl | 4-((R)-1-methylpyrrolidin-3-yl)-phenyl |
| 341. | ethyl | 4-(2,2-dimethylpyrrolidin-1-yl)-phenyl |
| 342. | ethyl | 4-(3,3-dimethylpyrrolidin-1-yl)-phenyl |
| 343. | ethyl | 4-(2-trifluoromethylpyrrolidin-1-yl)-phenyl |
| 344. | ethyl | 4-((S)-2-trifluoromethylpyrrolidin-1-yl)-phenyl |
| 345. | ethyl | 4-((R)-2-trifluoromethylpyrrolidin-1-yl)-phenyl |
| 346. | ethyl | 4-(3-trifluoromethylpyrrolidin-1-yl)-phenyl |
| 347. | ethyl | 4-((S)-3-trifluoromethylpyrrolidin-1-yl)-phenyl |
| 348. | ethyl | 4-((R)-3-trifluoromethylpyrrolidin-1-yl)-phenyl |
| 349. | ethyl | 4-(2-oxopyrrolidin-1-yl)-phenyl |
| 350. | ethyl | 4-(2-oxo-oxazolidin-3-yl)-phenyl |
| 351. | ethyl | 4-(piperidin-1-yl)-phenyl |
| 352. | ethyl | 4-(2-methylpiperidin-1-yl)-phenyl |
| 353. | ethyl | 4-((S)-2-methylpiperidin-1-yl)-phenyl |
| 354. | ethyl | 4-((R)-2-methylpiperidin-1-yl)-phenyl |
| 355. | ethyl | 4-(piperazin-1-yl)-phenyl |
| 356. | ethyl | 4-(4-methylpiperazin-1-yl)-phenyl |
| 357. | ethyl | 4-(morpholin-4-yl)-phenyl |

TABLE A-continued

| No. | R¹ | Ar |
|---|---|---|
| 358. | ethyl | 4-(thiomorpholin-4-yl)-phenyl |
| 359. | ethyl | 4-(1-oxo-thiomorpholin-4-yl)-phenyl |
| 360. | ethyl | 4-(1,1-dioxo-thiomorpholin-4-yl)-phenyl |
| 361. | ethyl | 4-(pyrrol-1-yl)-phenyl |
| 362. | ethyl | 4-(pyrrol-2-yl)-phenyl |
| 363. | ethyl | 4-(pyrrol-3-yl)-phenyl |
| 364. | ethyl | 4-(1-methylpyrrol-2-yl)-phenyl |
| 365. | ethyl | 4-(1-methylpyrrol-3-yl)-phenyl |
| 366. | ethyl | 4-(furan-2-yl)-phenyl |
| 367. | ethyl | 4-(furan-3-yl)-phenyl |
| 368. | ethyl | 4-(thiophen-2-yl)-phenyl |
| 369. | ethyl | 4-(thiophen-3-yl)-phenyl |
| 370. | ethyl | 4-(5-propylthien-2-yl)-phenyl |
| 371. | ethyl | 4-(pyrazol-1-yl)-phenyl |
| 372. | ethyl | 4-(pyrazol-3-yl)-phenyl |
| 373. | ethyl | 4-(pyrazol-4-yl)-phenyl |
| 374. | ethyl | 4-(1-methyl-1H-pyrazol-4-yl)-phenyl |
| 375. | ethyl | 4-(1-ethyl-1H-pyrazol-4-yl)-phenyl |
| 376. | ethyl | 4-(1-methyl-1H-pyrazol-5-yl)-phenyl |
| 377. | ethyl | 4-(1H-imidazol-2-yl)-phenyl |
| 378. | ethyl | 4-(imidazol-1-yl)-phenyl |
| 379. | ethyl | 4-(1-methylimidazol-2-yl)-phenyl |
| 380. | ethyl | 4-(oxazol-2-yl)-phenyl |
| 381. | ethyl | 4-(oxazol-4-yl)-phenyl |
| 382. | ethyl | 4-(oxazol-5-yl)-phenyl |
| 383. | ethyl | 4-(isoxazol-3-yl)-phenyl |
| 384. | ethyl | 4-(isoxazol-4-yl)-phenyl |
| 385. | ethyl | 4-(isoxazol-5-yl)-phenyl |
| 386. | ethyl | 4-([1,2,3]-triazol-1-yl)-phenyl |
| 387. | ethyl | 4-([1,2,4]-triazol-1-yl)-phenyl |
| 388. | ethyl | 4-([1,2,3]-triazol-2-yl)-phenyl |
| 389. | ethyl | 4-(4H-[1,2,4]-triazol-3-yl)-phenyl |
| 390. | ethyl | 4-([1,2,4]-triazol-4-yl)-phenyl |
| 391. | ethyl | 4-(2H-[1,2,3]-triazol-4-yl)-phenyl |
| 392. | ethyl | 4-(4-methyl-4H-[1,2,4]-triazol-3-yl)-phenyl |
| 393. | ethyl | 4-(2-methyl-2H-[1,2,3]-triazol-4-yl)-phenyl |
| 394. | ethyl | 4-([1,3,4]-oxadiazol-2-yl)-phenyl |
| 395. | ethyl | 4-([1,2,4]-oxadiazol-3-yl)-phenyl |
| 396. | ethyl | 4-([1,2,4]-oxadiazol-5-yl)-phenyl |
| 397. | ethyl | 4-([1,2,3]-oxadiazol-4-yl)-phenyl |
| 398. | ethyl | 4-([1,2,3]-oxadiazol-5-yl)-phenyl |
| 399. | ethyl | 4-([1,2,3]-thiadiazol-4-yl)-phenyl |
| 400. | ethyl | 4-(1H-tetrazol-5-yl)-phenyl |
| 401. | ethyl | 4-(tetrazol-1-yl)-phenyl |
| 402. | ethyl | 4-(2-methyl-2H-tetrazol-5-yl)-phenyl |
| 403. | ethyl | 4-(1-methyl-1H-tetrazol-5-yl)-phenyl |
| 404. | ethyl | 4-furazan-3-yl-phenyl |
| 405. | ethyl | 4-(pyrid-2-yl)-phenyl |
| 406. | ethyl | 4-(pyrid-3-yl)-phenyl |
| 407. | ethyl | 4-(pyrid-4-yl)-phenyl |
| 408. | ethyl | 4-(pyrimidin-2-yl)-phenyl |
| 409. | ethyl | 4-(pyrimidin-4-yl)-phenyl |
| 410. | ethyl | 4-(pyrimidin-5-yl)-phenyl |
| 411. | ethyl | 5-isopropylthiophen-2-yl |
| 412. | ethyl | 2-chlorothiophen-5-yl |
| 413. | ethyl | 2,5-dichlorothiophen-4-yl |
| 414. | ethyl | 2,3-dichlorothiophen-5-yl |
| 415. | ethyl | 2-chloro-3-nitrothiophen-5-yl |
| 416. | ethyl | 2-(phenylsulfonyl)-thiophen-5-yl |
| 417. | ethyl | 2-(pyridin-2-yl)thiophen-5-yl |
| 418. | ethyl | 2-(5-(trifluoromethyl)isoxazol-3-yl)-thiophen-5-yl |
| 419. | ethyl | 2-(2-methylthiazol-4-yl)-thiophen-5-yl |
| 420. | ethyl | 1-methyl-1H-imidazol-4-yl |
| 421. | ethyl | 1,2-dimethyl-1H-imidazol-4-yl |
| 422. | ethyl | 3,5-dimethylisoxazol-4-yl |
| 423. | ethyl | thiazol-2-yl |
| 424. | ethyl | 4-methylthiazol-2-yl |
| 425. | ethyl | 4-isopropylthiazol-2-yl |
| 426. | ethyl | 4-trifluoromethylthiazol-2-yl |
| 427. | ethyl | 5-methylthiazol-2-yl |
| 428. | ethyl | 5-isopropylthiazol-2-yl |
| 429. | ethyl | 5-trifluoromethylthiazol-2-yl |
| 430. | ethyl | 2,4-dimethylthiazol-5-yl |
| 431. | ethyl | 2-acetamido-4-methylthiazol-5-yl |
| 432. | ethyl | 4H-[1,2,4]triazol-3-yl |
| 433. | ethyl | 5-methyl-4H-[1,2,4]triazol-3-yl |
| 434. | ethyl | 4-methyl-4H-[1,2,4]triazol-3-yl |

TABLE A-continued

| No. | R¹ | Ar |
|---|---|---|
| 435. | ethyl | 5-isopropyl-4H-[1,2,4]triazol-3-yl |
| 436. | ethyl | 5-trifluoromethyl-4H-[1,2,4]triazol-3-yl |
| 437. | ethyl | 4,5-dimethyl-4H-[1,2,4]triazol-3-yl |
| 438. | ethyl | 5-isopropyl-4-methyl-4H-[1,2,4]triazol-3-yl |
| 439. | ethyl | 5-trifluoromethyl-4-methyl-4H-[1,2,4]triazol-3-yl |
| 440. | ethyl | [1,3,4]thiadiazol-2-yl |
| 441. | ethyl | 5-methyl-[1,3,4]thiadiazol-2-yl |
| 442. | ethyl | 5-isopropyl-[1,3,4]thiadiazol-2-yl |
| 443. | ethyl | 5-trifluoromethyl-[1,3,4]thiadiazol-2-yl |
| 444. | ethyl | 3-bromo-2-chloropyrid-5-yl |
| 445. | ethyl | 2-(4-morpholino)-pyrid-5-yl |
| 446. | ethyl | 2-phenoxypyrid-5-yl |
| 447. | ethyl | (2-isopropyl)-pyrimidin-5-yl |
| 448. | ethyl | (5-isopropyl)-pyrimidin-2-yl |
| 449. | ethyl | 8-quinolyl |
| 450. | ethyl | 5-isoquinolyl |
| 451. | ethyl | 2-(2,2,2-trifluoroacetyl)-1,2,3,4-tetrahydroisoquinolin-7-yl |
| 452. | ethyl | 5-chloro-3-methylbenzothiophen-2-yl |
| 453. | ethyl | 3,4-dihydro-4-methyl-2H-benzo[b][1,4]oxazinyl |
| 454. | ethyl | benzothiazol-6-yl |
| 455. | ethyl | benzo[2,1,3]oxadiazol-4-yl |
| 456. | ethyl | 5-chlorobenzo[1,2,5]oxadiazolyl |
| 457. | ethyl | 7-chlorobenzo[2,1,3]oxadiazol-4-yl |
| 458. | ethyl | benzo[2,1,3]thiadiazol-4-yl |
| 459. | methyl | 4-ethylphenyl |
| 460. | methyl | 4-propylphenyl |
| 461. | methyl | 4-isopropylphenyl |
| 462. | methyl | 4-sec-butylphenyl |
| 463. | methyl | 4-isobutylphenyl |
| 464. | methyl | 4-(1,1-dimethylpropyl)-phenyl |
| 465. | methyl | 4-vinylphenyl |
| 466. | methyl | 4-isopropenylphenyl |
| 467. | methyl | 4-(fluoromethyl)phenyl |
| 468. | methyl | 3-(fluoromethyl)phenyl |
| 469. | methyl | 2-(fluoromethyl)phenyl |
| 470. | methyl | 4-(difluoromethyl)phenyl |
| 471. | methyl | 3-(difluoromethyl)phenyl |
| 472. | methyl | 2-(difluoromethyl)phenyl |
| 473. | methyl | 4-(trifluoromethyl)phenyl |
| 474. | methyl | 3-(trifluoromethyl)phenyl |
| 475. | methyl | 2-(trifluoromethyl)phenyl |
| 476. | methyl | 4-(1-fluoroethyl)-phenyl |
| 477. | methyl | 4-((S)-1-fluoroethyl)-phenyl |
| 478. | methyl | 4-((R)-1-fluoroethyl)-phenyl |
| 479. | methyl | 4-(2-fluoroethyl)-phenyl |
| 480. | methyl | 4-(1,1-difluoroethyl)-phenyl |
| 481. | methyl | 4-(2,2-difluoroethyl)-phenyl |
| 482. | methyl | 4-(2,2,2-trifluoroethyl)-phenyl |
| 483. | methyl | 4-(3-fluoropropyl)-phenyl |
| 484. | methyl | 4-(2-fluoropropyl)-phenyl |
| 485. | methyl | 4-((S)-2-fluoropropyl)-phenyl |
| 486. | methyl | 4-((R)-2-fluoropropyl)-phenyl |
| 487. | methyl | 4-(3,3-difluoropropyl)-phenyl |
| 488. | methyl | 4-(3,3,3-trifluoropropyl)-phenyl |
| 489. | methyl | 4-(1-fluoro-1-methylethyl)-phenyl |
| 490. | methyl | 4-(2-fluoro-1-methylethyl)-phenyl |
| 491. | methyl | 4-((S)-2-fluoro-1-methylethyl)-phenyl |
| 492. | methyl | 4-((R)-2-fluoro-1-methylethyl)-phenyl |
| 493. | methyl | 4-(2,2-difluoro-1-methylethyl)-phenyl |
| 494. | methyl | 4-((S)-2,2-difluoro-1-methylethyl)-phenyl |
| 495. | methyl | 4-((R)-2,2-difluoro-1-methylethyl)-phenyl |
| 496. | methyl | 4-(2,2,2-trifluoro-1-methylethyl)-phenyl |
| 497. | methyl | 4-((S)-2,2,2-trifluoro-1-methylethyl)-phenyl |
| 498. | methyl | 4-((R)-2,2,2-trifluoro-1-methylethyl)-phenyl |
| 499. | methyl | 4-(2-fluoro-1-fluoromethylethyl)-phenyl |
| 500. | methyl | 4-(1-difluoromethyl-2,2-difluoroethyl)-phenyl |
| 501. | methyl | 4-(1,1-dimethyl-2-fluoroethyl)-phenyl |
| 502. | methyl | 4-ethoxyphenyl |
| 503. | methyl | 4-propoxyphenyl |
| 504. | methyl | 4-isopropoxyphenyl |
| 505. | methyl | 4-butoxyphenyl |
| 506. | methyl | 4-(fluoromethoxy)-phenyl |
| 507. | methyl | 4-(difluoromethoxy)-phenyl |
| 508. | methyl | 4-(2-fluoroethoxy)-phenyl |
| 509. | methyl | 4-(2,2-difluoroethoxy)-phenyl |
| 510. | methyl | 4-(2,2,2-trifluoroethoxy)-phenyl |

TABLE A-continued

| No. | R¹ | Ar |
|---|---|---|
| 511. | methyl | 4-(1,1,2,2-tetrafluoroethoxy)-phenyl |
| 512. | methyl | 4-cyclopropylphenyl |
| 513. | methyl | 4-cyclobutylphenyl |
| 514. | methyl | 4-cyclopentylphenyl |
| 515. | methyl | 4-(2,2-difluorocyclopropyl)-phenyl |
| 516. | methyl | 2-fluoro-4-isopropylphenyl |
| 517. | methyl | 3-fluoro-4-isopropylphenyl |
| 518. | methyl | 4-(1-hydroxy-1-methylethyl)-phenyl |
| 519. | methyl | 4-(2-hydroxy-2-methylpropyl)-phenyl |
| 520. | methyl | 4-acetylphenyl |
| 521. | methyl | 4-carboxyphenyl |
| 522. | methyl | 4-(O-benzyl)-phenyl |
| 523. | methyl | 4-(2-methoxyethoxy)-phenyl |
| 524. | methyl | 4-($CH_2$—$N(CH_3)_2$)-phenyl |
| 525. | methyl | 4-(NH—CO—$NH_2$)-phenyl |
| 526. | methyl | 4-(methylsulfanyl)-phenyl |
| 527. | methyl | 4-(fluoromethylsulfanyl)-phenyl |
| 528. | methyl | 4-(difluoromethylsulfanyl)-phenyl |
| 529. | methyl | 4-(trifluoromethylsulfanyl)-phenyl |
| 530. | methyl | 4-(methylsulfonyl)-phenyl |
| 531. | methyl | 4-(N-methoxy-N-methyl-amino)-phenyl |
| 532. | methyl | 4-(methoxyamino)-phenyl |
| 533. | methyl | 4-(ethoxyamino)-phenyl |
| 534. | methyl | 4-(N-methylaminooxy)-phenyl |
| 535. | methyl | 4-(N,N-dimethylaminooxy)-phenyl |
| 536. | methyl | 4-(azetidin-1-yl)-phenyl |
| 537. | methyl | 4-(2-methylazetidin-1-yl)-phenyl |
| 538. | methyl | 4-((S)-2-methylazetidin-1-yl)-phenyl |
| 539. | methyl | 4-((R)-2-methylazetidin-1-yl)-phenyl |
| 540. | methyl | 4-(3-fluoroazetidin-1-yl)-phenyl |
| 541. | methyl | 4-(3-methoxyazetidin-1-yl)-phenyl |
| 542. | methyl | 4-(3-hydroxyazetidin-1-yl)-phenyl |
| 543. | methyl | 4-(pyrrolidin-1-yl)-phenyl |
| 544. | methyl | 4-(pyrrolidin-2-yl)-phenyl |
| 545. | methyl | 4-((S)-pyrrolidin-2-yl)-phenyl |
| 546. | methyl | 4-((R)-pyrrolidin-2-yl)-phenyl |
| 547. | methyl | 4-(pyrrolidin-3-yl)-phenyl |
| 548. | methyl | 4-((S)-pyrrolidin-3-yl)-phenyl |
| 549. | methyl | 4-((R)-pyrrolidin-3-yl)-phenyl |
| 550. | methyl | 4-(2-fluoropyrrolidin-1-yl)-phenyl |
| 551. | methyl | 4-((S)-2-fluoropyrrolidin-1-yl)-phenyl |
| 552. | methyl | 4-((R)-2-fluoropyrrolidin-1-yl)-phenyl |
| 553. | methyl | 4-(3-fluoropyrrolidin-1-yl)-phenyl |
| 554. | methyl | 4-((S)-3-fluoropyrrolidin-1-yl)-phenyl |
| 555. | methyl | 4-((R)-3-fluoropyrrolidin-1-yl)-phenyl |
| 556. | methyl | 4-(2,2-difluoropyrrolidin-1-yl)-phenyl |
| 557. | methyl | 4-(3,3-difluoropyrrolidin-1-yl)-phenyl |
| 558. | methyl | 4-(2-methylpyrrolidin-1-yl)-phenyl |
| 559. | methyl | 4-((S)-2-methylpyrrolidin-1-yl)-phenyl |
| 560. | methyl | 4-((R)-2-methylpyrrolidin-1-yl)-phenyl |
| 561. | methyl | 4-(3-methylpyrrolidin-1-yl)-phenyl |
| 562. | methyl | 4-((S)-3-methylpyrrolidin-1-yl)-phenyl |
| 563. | methyl | 4-((R)-3-methylpyrrolidin-1-yl)-phenyl |
| 564. | methyl | 4-(1-methylpyrrolidin-2-yl)-phenyl |
| 565. | methyl | 4-((S)-1-methylpyrrolidin-2-yl)-phenyl |
| 566. | methyl | 4-((R)-1-methylpyrrolidin-2-yl)-phenyl |
| 567. | methyl | 4-(1-methylpyrrolidin-3-yl)-phenyl |
| 568. | methyl | 4-((S)-1-methylpyrrolidin-3-yl)-phenyl |
| 569. | methyl | 4-((R)-1-methylpyrrolidin-3-yl)-phenyl |
| 570. | methyl | 4-(2,2-dimethylpyrrolidin-1-yl)-phenyl |
| 571. | methyl | 4-(3,3-dimethylpyrrolidin-1-yl)-phenyl |
| 572. | methyl | 4-(2-trifluoromethylpyrrolidin-1-yl)-phenyl |
| 573. | methyl | 4-((S)-2-trifluoromethylpyrrolidin-1-yl)-phenyl |
| 574. | methyl | 4-((R)-2-trifluoromethylpyrrolidin-1-yl)-phenyl |
| 575. | methyl | 4-(3-trifluoromethylpyrrolidin-1-yl)-phenyl |
| 576. | methyl | 4-((S)-3-trifluoromethylpyrrolidin-1-yl)-phenyl |
| 577. | methyl | 4-((R)-3-trifluoromethylpyrrolidin-1-yl)-phenyl |
| 578. | methyl | 4-(2-oxopyrrolidin-1-yl)-phenyl |
| 579. | methyl | 4-(2-oxo-oxazolidin-3-yl)-phenyl |
| 580. | methyl | 4-(piperidin-1-yl)-phenyl |
| 581. | methyl | 4-(2-methylpiperidin-1-yl)-phenyl |
| 582. | methyl | 4-((S)-2-methylpiperidin-1-yl)-phenyl |
| 583. | methyl | 4-((R)-2-methylpiperidin-1-yl)-phenyl |
| 584. | methyl | 4-(piperazin-1-yl)-phenyl |
| 585. | methyl | 4-(4-methylpiperazin-1-yl)-phenyl |
| 586. | methyl | 4-(morpholin-4-yl)-phenyl |
| 587. | methyl | 4-(thiomorpholin-4-yl)-phenyl |

TABLE A-continued

| No. | R¹ | Ar |
|---|---|---|
| 588. | methyl | 4-(1-oxo-thiomorpholin-4-yl)-phenyl |
| 589. | methyl | 4-(1,1-dioxo-thiomorpholin-4-yl)-phenyl |
| 590. | methyl | 4-(pyrrol-1-yl)-phenyl |
| 591. | methyl | 4-(pyrrol-2-yl)-phenyl |
| 592. | methyl | 4-(pyrrol-3-yl)-phenyl |
| 593. | methyl | 4-(1-methylpyrrol-2-yl)-phenyl |
| 594. | methyl | 4-(1-methylpyrrol-3-yl)-phenyl |
| 595. | methyl | 4-(furan-2-yl)-phenyl |
| 596. | methyl | 4-(furan-3-yl)-phenyl |
| 597. | methyl | 4-(thiophen-2-yl)-phenyl |
| 598. | methyl | 4-(thiophen-3-yl)-phenyl |
| 599. | methyl | 4-(5-propylthien-2-yl)-phenyl |
| 600. | methyl | 4-(pyrazol-1-yl)-phenyl |
| 601. | methyl | 4-(pyrazol-3-yl)-phenyl |
| 602. | methyl | 4-(pyrazol-4-yl)-phenyl |
| 603. | methyl | 4-(1-methyl-1H-pyrazol-4-yl)-phenyl |
| 604. | methyl | 4-(1-ethyl-1H-pyrazol-4-yl)-phenyl |
| 605. | methyl | 4-(1-methyl-1H-pyrazol-5-yl)-phenyl |
| 606. | methyl | 4-(1H-imidazol-2-yl)-phenyl |
| 607. | methyl | 4-(imidazol-1-yl)-phenyl |
| 608. | methyl | 4-(1-methylimidazol-2-yl)-phenyl |
| 609. | methyl | 4-(oxazol-2-yl)-phenyl |
| 610. | methyl | 4-(oxazol-4-yl)-phenyl |
| 611. | methyl | 4-(oxazol-5-yl)-phenyl |
| 612. | methyl | 4-(isoxazol-3-yl)-phenyl |
| 613. | methyl | 4-(isoxazol-4-yl)-phenyl |
| 614. | methyl | 4-(isoxazol-5-yl)-phenyl |
| 615. | methyl | 4-([1,2,3]-triazol-1-yl)-phenyl |
| 616. | methyl | 4-([1,2,4]-triazol-1-yl)-phenyl |
| 617. | methyl | 4-([1,2,3]-triazol-2-yl)-phenyl |
| 618. | methyl | 4-(4H-[1,2,4]-triazol-3-yl)-phenyl |
| 619. | methyl | 4-([1,2,4]-triazol-4-yl)-phenyl |
| 620. | methyl | 4-(2H-[1,2,3]-triazol-4-yl)-phenyl |
| 621. | methyl | 4-(4-methyl-4H-[1,2,4]-triazol-3-yl)-phenyl |
| 622. | methyl | 4-(2-methyl-2H-[1,2,3]-triazol-4-yl)-phenyl |
| 623. | methyl | 4-([1,3,4]-oxadiazol-2-yl)-phenyl |
| 624. | methyl | 4-([1,2,4]-oxadiazol-3-yl)-phenyl |
| 625. | methyl | 4-([1,2,4]-oxadiazol-5-yl)-phenyl |
| 626. | methyl | 4-([1,2,3]-oxadiazol-4-yl)-phenyl |
| 627. | methyl | 4-([1,2,3]-oxadiazol-5-yl)-phenyl |
| 628. | methyl | 4-([1,2,3]-thiadiazol-4-yl)-phenyl |
| 629. | methyl | 4-(1H-tetrazol-5-yl)-phenyl |
| 630. | methyl | 4-(tetrazol-1-yl)-phenyl |
| 631. | methyl | 4-(2-methyl-2H-tetrazol-5-yl)-phenyl |
| 632. | methyl | 4-(1-methyl-1H-tetrazol-5-yl)-phenyl |
| 633. | methyl | 4-furazan-3-yl-phenyl |
| 634. | methyl | 4-(pyrid-2-yl)-phenyl |
| 635. | methyl | 4-(pyrid-3-yl)-phenyl |
| 636. | methyl | 4-(pyrid-4-yl)-phenyl |
| 637. | methyl | 4-(pyrimidin-2-yl)-phenyl |
| 638. | methyl | 4-(pyrimidin-4-yl)-phenyl |
| 639. | methyl | 4-(pyrimidin-5-yl)-phenyl |
| 640. | methyl | 5-isopropylthiophen-2-yl |
| 641. | methyl | 2-chlorothiophen-5-yl |
| 642. | methyl | 2,5-dichlorothiophen-4-yl |
| 643. | methyl | 2,3-dichlorothiophen-5-yl |
| 644. | methyl | 2-chloro-3-nitrothiophen-5-yl |
| 645. | methyl | 2-(phenylsulfonyl)-thiophen-5-yl |
| 646. | methyl | 2-(pyridin-2-yl)thiophen-5-yl |
| 647. | methyl | 2-(5-(trifluoromethyl)isoxazol-3-yl)-thiophen-5-yl |
| 648. | methyl | 2-(2-methylthiazol-4-yl)-thiophen-5-yl |
| 649. | methyl | 1-methyl-1H-imidazol-4-yl |
| 650. | methyl | 1,2-dimethyl-1H-imidazol-4-yl |
| 651. | methyl | 3,5-dimethylisoxazol-4-yl |
| 652. | methyl | thiazol-2-yl |
| 653. | methyl | 4-methylthiazol-2-yl |
| 654. | methyl | 4-isopropylthiazol-2-yl |
| 655. | methyl | 4-trifluoromethylthiazol-2-yl |
| 656. | methyl | 5-methylthiazol-2-yl |
| 657. | methyl | 5-isopropylthiazol-2-yl |
| 658. | methyl | 5-trifluoromethylthiazol-2-yl |
| 659. | methyl | 2,4-dimethylthiazol-5-yl |
| 660. | methyl | 2-acetamido-4-methylthiazol-5-yl |
| 661. | methyl | 4H-[1,2,4]triazol-3-yl |
| 662. | methyl | 5-methyl-4H-[1,2,4]triazol-3-yl |
| 663. | methyl | 4-methyl-4H-[1,2,4]triazol-3-yl |
| 664. | methyl | 5-isopropyl-4H-[1,2,4]triazol-3-yl |

TABLE A-continued

| No. | R¹ | Ar |
|---|---|---|
| 665. | methyl | 5-trifluoromethyl-4H-[1,2,4]triazol-3-yl |
| 666. | methyl | 4,5-dimethyl-4H-[1,2,4]triazol-3-yl |
| 667. | methyl | 5-isopropyl-4-methyl-4H-[1,2,4]triazol-3-yl |
| 668. | methyl | 5-trifluoromethyl-4-methyl-4H-[1,2,4]triazol-3-yl |
| 669. | methyl | [1,3,4]thiadiazol-2-yl |
| 670. | methyl | 5-methyl-[1,3,4]thiadiazol-2-yl |
| 671. | methyl | 5-isopropyl-[1,3,4]thiadiazol-2-yl |
| 672. | methyl | 5-trifluoromethyl-[1,3,4]thiadiazol-2-yl |
| 673. | methyl | 3-bromo-2-chloropyrid-5-yl |
| 674. | methyl | 2-(4-morpholino)-pyrid-5-yl |
| 675. | methyl | 2-phenoxypyrid-5-yl |
| 676. | methyl | (2-isopropyl)-pyrimidin-5-yl |
| 677. | methyl | (5-isopropyl)-pyrimidin-2-yl |
| 678. | methyl | 8-quinolyl |
| 679. | methyl | 5-isoquinolyl |
| 680. | methyl | 2-(2,2,2-trifluoroacetyl)-1,2,3,4-tetrahydroisoquinolin-7-yl |
| 681. | methyl | 5-chloro-3-methylbenzothiophen-2-yl |
| 682. | methyl | 3,4-dihydro-4-methyl-2H-benzo[b][1,4]oxazinyl |
| 683. | methyl | benzothiazol-6-yl |
| 684. | methyl | benzo[2,1,3]oxadiazol-4-yl |
| 685. | methyl | 5-chlorobenzo[1,2,5]oxadiazolyl |
| 686. | methyl | 7-chlorobenzo[2,1,3]oxadiazol-4-yl |
| 687. | methyl | benzo[2,1,3]thiadiazol-4-yl |
| 688. | 3-fluoropropyl | 4-ethylphenyl |
| 689. | 3-fluoropropyl | 4-propylphenyl |
| 690. | 3-fluoropropyl | 4-isopropylphenyl |
| 691. | 3-fluoropropyl | 4-sec-butylphenyl |
| 692. | 3-fluoropropyl | 4-isobutylphenyl |
| 693. | 3-fluoropropyl | 4-(1,1-dimethylpropyl)-phenyl |
| 694. | 3-fluoropropyl | 4-vinylphenyl |
| 695. | 3-fluoropropyl | 4-isopropenylphenyl |
| 696. | 3-fluoropropyl | 4-(fluoromethyl)phenyl |
| 697. | 3-fluoropropyl | 3-(fluoromethyl)phenyl |
| 698. | 3-fluoropropyl | 2-(fluoromethyl)phenyl |
| 699. | 3-fluoropropyl | 4-(difluoromethyl)phenyl |
| 700. | 3-fluoropropyl | 3-(difluoromethyl)phenyl |
| 701. | 3-fluoropropyl | 2-(difluoromethyl)phenyl |
| 702. | 3-fluoropropyl | 4-(trifluoromethyl)phenyl |
| 703. | 3-fluoropropyl | 3-(trifluoromethyl)phenyl |
| 704. | 3-fluoropropyl | 2-(trifluoromethyl)phenyl |
| 705. | 3-fluoropropyl | 4-(1-fluoroethyl)-phenyl |
| 706. | 3-fluoropropyl | 4-((S)-1-fluoroethyl)-phenyl |
| 707. | 3-fluoropropyl | 4-((R)-1-fluoroethyl)-phenyl |
| 708. | 3-fluoropropyl | 4-(2-fluoroethyl)-phenyl |
| 709. | 3-fluoropropyl | 4-(1,1-difluoroethyl)-phenyl |
| 710. | 3-fluoropropyl | 4-(2,2-difluoroethyl)-phenyl |
| 711. | 3-fluoropropyl | 4-(2,2,2-trifluoroethyl)-phenyl |
| 712. | 3-fluoropropyl | 4-(3-fluoropropyl)-phenyl |
| 713. | 3-fluoropropyl | 4-(2-fluoropropyl)-phenyl |
| 714. | 3-fluoropropyl | 4-((S)-2-fluoropropyl)-phenyl |
| 715. | 3-fluoropropyl | 4-((R)-2-fluoropropyl)-phenyl |
| 716. | 3-fluoropropyl | 4-(3,3-difluoropropyl)-phenyl |
| 717. | 3-fluoropropyl | 4-(3,3,3-trifluoropropyl)-phenyl |
| 718. | 3-fluoropropyl | 4-(1-fluoro-1-methylethyl)-phenyl |
| 719. | 3-fluoropropyl | 4-(2-fluoro-1-methylethyl)-phenyl |
| 720. | 3-fluoropropyl | 4-((S)-2-fluoro-1-methylethyl)-phenyl |
| 721. | 3-fluoropropyl | 4-((R)-2-fluoro-1-methylethyl)-phenyl |
| 722. | 3-fluoropropyl | 4-(2,2-difluoro-1-methylethyl)-phenyl |
| 723. | 3-fluoropropyl | 4-((S)-2,2-difluoro-1-methylethyl)-phenyl |
| 724. | 3-fluoropropyl | 4-((R)-2,2-difluoro-1-methylethyl)-phenyl |
| 725. | 3-fluoropropyl | 4-(2,2,2-trifluoro-1-methylethyl)-phenyl |
| 726. | 3-fluoropropyl | 4-((S)-2,2,2-trifluoro-1-methylethyl)-phenyl |
| 727. | 3-fluoropropyl | 4-((R)-2,2,2-trifluoro-1-methylethyl)-phenyl |
| 728. | 3-fluoropropyl | 4-(2-fluoro-1-fluoromethylethyl)-phenyl |
| 729. | 3-fluoropropyl | 4-(1-difluoromethyl-2,2-difluoroethyl)-phenyl |
| 730. | 3-fluoropropyl | 4-(1,1-dimethyl-2-fluoroethyl)-phenyl |
| 731. | 3-fluoropropyl | 4-ethoxyphenyl |
| 732. | 3-fluoropropyl | 4-propoxyphenyl |
| 733. | 3-fluoropropyl | 4-isopropoxyphenyl |
| 734. | 3-fluoropropyl | 4-butoxyphenyl |
| 735. | 3-fluoropropyl | 4-(fluoromethoxy)-phenyl |
| 736. | 3-fluoropropyl | 4-(difluoromethoxy)-phenyl |
| 737. | 3-fluoropropyl | 4-(2-fluoroethoxy)-phenyl |
| 738. | 3-fluoropropyl | 4-(2,2-difluoroethoxy)-phenyl |
| 739. | 3-fluoropropyl | 4-(2,2,2-trifluoroethoxy)-phenyl |
| 740. | 3-fluoropropyl | 4-(1,1,2,2-tetrafluoroethoxy)-phenyl |

TABLE A-continued

| No. | R¹ | Ar |
|---|---|---|
| 741. | 3-fluoropropyl | 4-cyclopropylphenyl |
| 742. | 3-fluoropropyl | 4-cyclobutylphenyl |
| 743. | 3-fluoropropyl | 4-cyclopentylphenyl |
| 744. | 3-fluoropropyl | 4-(2,2-difluorocyclopropyl)-phenyl |
| 745. | 3-fluoropropyl | 2-fluoro-4-isopropylphenyl |
| 746. | 3-fluoropropyl | 3-fluoro-4-isopropylphenyl |
| 747. | 3-fluoropropyl | 4-(1-hydroxy-1-methylethyl)-phenyl |
| 748. | 3-fluoropropyl | 4-(2-hydroxy-2-methylpropyl)-phenyl |
| 749. | 3-fluoropropyl | 4-acetylphenyl |
| 750. | 3-fluoropropyl | 4-carboxyphenyl |
| 751. | 3-fluoropropyl | 4-(O-benzyl)-phenyl |
| 752. | 3-fluoropropyl | 4-(2-methoxyethoxy)-phenyl |
| 753. | 3-fluoropropyl | 4-($CH_2$—$N(CH_3)_2$)-phenyl |
| 754. | 3-fluoropropyl | 4-(NH—CO—$NH_2$)-phenyl |
| 755. | 3-fluoropropyl | 4-(methylsulfanyl)-phenyl |
| 756. | 3-fluoropropyl | 4-(fluoromethylsulfanyl)-phenyl |
| 757. | 3-fluoropropyl | 4-(difluoromethylsulfanyl)-phenyl |
| 758. | 3-fluoropropyl | 4-(trifluoromethylsulfanyl)-phenyl |
| 759. | 3-fluoropropyl | 4-(methylsulfonyl)-phenyl |
| 760. | 3-fluoropropyl | 4-(N-methoxy-N-methyl-amino)-phenyl |
| 761. | 3-fluoropropyl | 4-(methoxyamino)-phenyl |
| 762. | 3-fluoropropyl | 4-(ethoxyamino)-phenyl |
| 763. | 3-fluoropropyl | 4-(N-methylaminooxy)-phenyl |
| 764. | 3-fluoropropyl | 4-(N,N-dimethylaminooxy)-phenyl |
| 765. | 3-fluoropropyl | 4-(azetidin-1-yl)-phenyl |
| 766. | 3-fluoropropyl | 4-(2-methylazetidin-1-yl)-phenyl |
| 767. | 3-fluoropropyl | 4-((S)-2-methylazetidin-1-yl)-phenyl |
| 768. | 3-fluoropropyl | 4-((R)-2-methylazetidin-1-yl)-phenyl |
| 769. | 3-fluoropropyl | 4-(3-fluoroazetidin-1-yl)-phenyl |
| 770. | 3-fluoropropyl | 4-(3-methoxyazetidin-1-yl)-phenyl |
| 771. | 3-fluoropropyl | 4-(3-hydroxyazetidin-1-yl)-phenyl |
| 772. | 3-fluoropropyl | 4-(pyrrolidin-1-yl)-phenyl |
| 773. | 3-fluoropropyl | 4-(pyrrolidin-2-yl)-phenyl |
| 774. | 3-fluoropropyl | 4-((S)-pyrrolidin-2-yl)-phenyl |
| 775. | 3-fluoropropyl | 4-((R)-pyrrolidin-2-yl)-phenyl |
| 776. | 3-fluoropropyl | 4-(pyrrolidin-3-yl)-phenyl |
| 777. | 3-fluoropropyl | 4-((S)-pyrrolidin-3-yl)-phenyl |
| 778. | 3-fluoropropyl | 4-((R)-pyrrolidin-3-yl)-phenyl |
| 779. | 3-fluoropropyl | 4-(2-fluoropyrrolidin-1-yl)-phenyl |
| 780. | 3-fluoropropyl | 4-((S)-2-fluoropyrrolidin-1-yl)-phenyl |
| 781. | 3-fluoropropyl | 4-((R)-2-fluoropyrrolidin-1-yl)-phenyl |
| 782. | 3-fluoropropyl | 4-(3-fluoropyrrolidin-1-yl)-phenyl |
| 783. | 3-fluoropropyl | 4-((S)-3-fluoropyrrolidin-1-yl)-phenyl |
| 784. | 3-fluoropropyl | 4-((R)-3-fluoropyrrolidin-1-yl)-phenyl |
| 785. | 3-fluoropropyl | 4-(2,2-difluoropyrrolidin-1-yl)-phenyl |
| 786. | 3-fluoropropyl | 4-(3,3-difluoropyrrolidin-1-yl)-phenyl |
| 787. | 3-fluoropropyl | 4-(2-methylpyrrolidin-1-yl)-phenyl |
| 788. | 3-fluoropropyl | 4-((S)-2-methylpyrrolidin-1-yl)-phenyl |
| 789. | 3-fluoropropyl | 4-((R)-2-methylpyrrolidin-1-yl)-phenyl |
| 790. | 3-fluoropropyl | 4-(3-methylpyrrolidin-1-yl)-phenyl |
| 791. | 3-fluoropropyl | 4-((S)-3-methylpyrrolidin-1-yl)-phenyl |
| 792. | 3-fluoropropyl | 4-((R)-3-methylpyrrolidin-1-yl)-phenyl |
| 793. | 3-fluoropropyl | 4-(1-methylpyrrolidin-2-yl)-phenyl |
| 794. | 3-fluoropropyl | 4-((S)-1-methylpyrrolidin-2-yl)-phenyl |
| 795. | 3-fluoropropyl | 4-((R)-1-methylpyrrolidin-2-yl)-phenyl |
| 796. | 3-fluoropropyl | 4-(1-methylpyrrolidin-3-yl)-phenyl |
| 797. | 3-fluoropropyl | 4-((S)-1-methylpyrrolidin-3-yl)-phenyl |
| 798. | 3-fluoropropyl | 4-((R)-1-methylpyrrolidin-3-yl)-phenyl |
| 799. | 3-fluoropropyl | 4-(2,2-dimethylpyrrolidin-1-yl)-phenyl |
| 800. | 3-fluoropropyl | 4-(3,3-dimethylpyrrolidin-1-yl)-phenyl |
| 801. | 3-fluoropropyl | 4-(2-trifluoromethylpyrrolidin-1-yl)-phenyl |
| 802. | 3-fluoropropyl | 4-((S)-2-trifluoromethylpyrrolidin-1-yl)-phenyl |
| 803. | 3-fluoropropyl | 4-((R)-2-trifluoromethylpyrrolidin-1-yl)-phenyl |
| 804. | 3-fluoropropyl | 4-(3-trifluoromethylpyrrolidin-1-yl)-phenyl |
| 805. | 3-fluoropropyl | 4-((S)-3-trifluoromethylpyrrolidin-1-yl)-phenyl |
| 806. | 3-fluoropropyl | 4-((R)-3-trifluoromethylpyrrolidin-1-yl)-phenyl |
| 807. | 3-fluoropropyl | 4-(2-oxopyrrolidin-1-yl)-phenyl |
| 808. | 3-fluoropropyl | 4-(2-oxo-oxazolidin-3-yl)-phenyl |
| 809. | 3-fluoropropyl | 4-(piperidin-1-yl)-phenyl |
| 810. | 3-fluoropropyl | 4-(2-methylpiperidin-1-yl)-phenyl |
| 811. | 3-fluoropropyl | 4-((S)-2-methylpiperidin-1-yl)-phenyl |
| 812. | 3-fluoropropyl | 4-((R)-2-methylpiperidin-1-yl)-phenyl |
| 813. | 3-fluoropropyl | 4-(piperazin-1-yl)-phenyl |
| 814. | 3-fluoropropyl | 4-(4-methylpiperazin-1-yl)-phenyl |
| 815. | 3-fluoropropyl | 4-(morpholin-4-yl)-phenyl |
| 816. | 3-fluoropropyl | 4-(thiomorpholin-4-yl)-phenyl |
| 817. | 3-fluoropropyl | 4-(1-oxo-thiomorpholin-4-yl)-phenyl |

TABLE A-continued

| No. | R¹ | Ar |
|---|---|---|
| 818. | 3-fluoropropyl | 4-(1,1-dioxo-thiomorpholin-4-yl)-phenyl |
| 819. | 3-fluoropropyl | 4-(pyrrol-1-yl)-phenyl |
| 820. | 3-fluoropropyl | 4-(pyrrol-2-yl)-phenyl |
| 821. | 3-fluoropropyl | 4-(pyrrol-3-yl)-phenyl |
| 822. | 3-fluoropropyl | 4-(1-methylpyrrol-2-yl)-phenyl |
| 823. | 3-fluoropropyl | 4-(1-methylpyrrol-3-yl)-phenyl |
| 824. | 3-fluoropropyl | 4-(furan-2-yl)-phenyl |
| 825. | 3-fluoropropyl | 4-(furan-3-yl)-phenyl |
| 826. | 3-fluoropropyl | 4-(thiophen-2-yl)-phenyl |
| 827. | 3-fluoropropyl | 4-(thiophen-3-yl)-phenyl |
| 828. | 3-fluoropropyl | 4-(5-propylthien-2-yl)-phenyl |
| 829. | 3-fluoropropyl | 4-(pyrazol-1-yl)-phenyl |
| 830. | 3-fluoropropyl | 4-(pyrazol-3-yl)-phenyl |
| 831. | 3-fluoropropyl | 4-(pyrazol-4-yl)-phenyl |
| 832. | 3-fluoropropyl | 4-(1-methyl-1H-pyrazol-4-yl)-phenyl |
| 833. | 3-fluoropropyl | 4-(1-ethyl-1H-pyrazol-4-yl)-phenyl |
| 834. | 3-fluoropropyl | 4-(1-methyl-1H-pyrazol-5-yl)-phenyl |
| 835. | 3-fluoropropyl | 4-(1H-imidazol-2-yl)-phenyl |
| 836. | 3-fluoropropyl | 4-(imidazol-1-yl)-phenyl |
| 837. | 3-fluoropropyl | 4-(1-methylimidazol-2-yl)-phenyl |
| 838. | 3-fluoropropyl | 4-(oxazol-2-yl)-phenyl |
| 839. | 3-fluoropropyl | 4-(oxazol-4-yl)-phenyl |
| 840. | 3-fluoropropyl | 4-(oxazol-5-yl)-phenyl |
| 841. | 3-fluoropropyl | 4-(isoxazol-3-yl)-phenyl |
| 842. | 3-fluoropropyl | 4-(isoxazol-4-yl)-phenyl |
| 843. | 3-fluoropropyl | 4-(isoxazol-5-yl)-phenyl |
| 844. | 3-fluoropropyl | 4-([1,2,3]-triazol-1-yl)-phenyl |
| 845. | 3-fluoropropyl | 4-([1,2,4]-triazol-1-yl)-phenyl |
| 846. | 3-fluoropropyl | 4-([1,2,3]-triazol-2-yl)-phenyl |
| 847. | 3-fluoropropyl | 4-(4H-[1,2,4]-triazol-3-yl)-phenyl |
| 848. | 3-fluoropropyl | 4-([1,2,4]-triazol-4-yl)-phenyl |
| 849. | 3-fluoropropyl | 4-(2H-[1,2,3]-triazol-4-yl)-phenyl |
| 850. | 3-fluoropropyl | 4-(4-methyl-4H-[1,2,4]-triazol-3-yl)-phenyl |
| 851. | 3-fluoropropyl | 4-(2-methyl-2H-[1,2,3]-triazol-4-yl)-phenyl |
| 852. | 3-fluoropropyl | 4-([1,3,4]-oxadiazol-2-yl)-phenyl |
| 853. | 3-fluoropropyl | 4-([1,2,4]-oxadiazol-3-yl)-phenyl |
| 854. | 3-fluoropropyl | 4-([1,2,4]-oxadiazol-5-yl)-phenyl |
| 855. | 3-fluoropropyl | 4-([1,2,3]-oxadiazol-4-yl)-phenyl |
| 856. | 3-fluoropropyl | 4-([1,2,3]-oxadiazol-5-yl)-phenyl |
| 857. | 3-fluoropropyl | 4-([1,2,3]-thiadiazol-4-yl)-phenyl |
| 858. | 3-fluoropropyl | 4-(1H-tetrazol-5-yl)-phenyl |
| 859. | 3-fluoropropyl | 4-(tetrazol-1-yl)-phenyl |
| 860. | 3-fluoropropyl | 4-(2-methyl-2H-tetrazol-5-yl)-phenyl |
| 861. | 3-fluoropropyl | 4-(1-methyl-1H-tetrazol-5-yl)-phenyl |
| 862. | 3-fluoropropyl | 4-furazan-3-yl-phenyl |
| 863. | 3-fluoropropyl | 4-(pyrid-2-yl)-phenyl |
| 864. | 3-fluoropropyl | 4-(pyrid-3-yl)-phenyl |
| 865. | 3-fluoropropyl | 4-(pyrid-4-yl)-phenyl |
| 866. | 3-fluoropropyl | 4-(pyrimidin-2-yl)-phenyl |
| 867. | 3-fluoropropyl | 4-(pyrimidin-4-yl)-phenyl |
| 868. | 3-fluoropropyl | 4-(pyrimidin-5-yl)-phenyl |
| 869. | 3-fluoropropyl | 5-isopropylthiophen-2-yl |
| 870. | 3-fluoropropyl | 2-chlorothiophen-5-yl |
| 871. | 3-fluoropropyl | 2,5-dichlorothiophen-4-yl |
| 872. | 3-fluoropropyl | 2,3-dichlorothiophen-5-yl |
| 873. | 3-fluoropropyl | 2-chloro-3-nitrothiophen-5-yl |
| 874. | 3-fluoropropyl | 2-(phenylsulfonyl)-thiophen-5-yl |
| 875. | 3-fluoropropyl | 2-(pyridin-2-yl)thiophen-5-yl |
| 876. | 3-fluoropropyl | 2-(5-(trifluoromethyl)isoxazol-3-yl)-thiophen-5-yl |
| 877. | 3-fluoropropyl | 2-(2-methylthiazol-4-yl)-thiophen-5-yl |
| 878. | 3-fluoropropyl | 1-methyl-1H-imidazol-4-yl |
| 879. | 3-fluoropropyl | 1,2-dimethyl-1H-imidazol-4-yl |
| 880. | 3-fluoropropyl | 3,5-dimethylisoxazol-4-yl |
| 881. | 3-fluoropropyl | thiazol-2-yl |
| 882. | 3-fluoropropyl | 4-methylthiazol-2-yl |
| 883. | 3-fluoropropyl | 4-isopropylthiazol-2-yl |
| 884. | 3-fluoropropyl | 4-trifluoromethylthiazol-2-yl |
| 885. | 3-fluoropropyl | 5-methylthiazol-2-yl |
| 886. | 3-fluoropropyl | 5-isopropylthiazol-2-yl |
| 887. | 3-fluoropropyl | s-trifluoromethylthiazol-2-yl |
| 888. | 3-fluoropropyl | 2,4-dimethylthiazol-5-yl |
| 889. | 3-fluoropropyl | 2-acetamido-4-methylthiazol-5-yl |
| 890. | 3-fluoropropyl | 4H-[1,2,4]triazol-3-yl |
| 891. | 3-fluoropropyl | 5-methyl-4H-[1,2,4]triazol-3-yl |
| 892. | 3-fluoropropyl | 4-methyl-4H-[1,2,4]triazol-3-yl |
| 893. | 3-fluoropropyl | 5-isopropyl-4H-[1,2,4]triazol-3-yl |
| 894. | 3-fluoropropyl | 5-trifluoromethyl-4H-[1,2,4]triazol-3-yl |

TABLE A-continued

| No. | R¹ | Ar |
|---|---|---|
| 895. | 3-fluoropropyl | 4,5-dimethyl-4H-[1,2,4]triazol-3-yl |
| 896. | 3-fluoropropyl | 5-isopropyl-4-methyl-4H-[1,2,4]triazol-3-yl |
| 897. | 3-fluoropropyl | 5-trifluoromethyl-4-methyl-4H-[1,2,4]triazol-3-yl |
| 898. | 3-fluoropropyl | [1,3,4]thiadiazol-2-yl |
| 899. | 3-fluoropropyl | 5-methyl-[1,3,4]thiadiazol-2-yl |
| 900. | 3-fluoropropyl | 5-isopropyl-[1,3,4]thiadiazol-2-yl |
| 901. | 3-fluoropropyl | 5-trifluoromethyl-[1,3,4]thiadiazol-2-yl |
| 902. | 3-fluoropropyl | 3-bromo-2-chloropyrid-5-yl |
| 903. | 3-fluoropropyl | 2-(4-morpholino)-pyrid-5-yl |
| 904. | 3-fluoropropyl | 2-phenoxypyrid-5-yl |
| 905. | 3-fluoropropyl | (2-isopropyl)-pyrimidin-5-yl |
| 906. | 3-fluoropropyl | (5-isopropyl)-pyrimidin-2-yl |
| 907. | 3-fluoropropyl | 8-quinolyl |
| 908. | 3-fluoropropyl | 5-isoquinolyl |
| 909. | 3-fluoropropyl | 2-(2,2,2-trifluoroacetyl)-1,2,3,4-tetrahydroisoquinolin-7-yl |
| 910. | 3-fluoropropyl | 5-chloro-3-methylbenzothiophen-2-yl |
| 911. | 3-fluoropropyl | 3,4-dihydro-4-methyl-2H-benzo[b][1,4]oxazinyl |
| 912. | 3-fluoropropyl | benzothiazol-6-yl |
| 913. | 3-fluoropropyl | benzo[2,1,3]oxadiazol-4-yl |
| 914. | 3-fluoropropyl | 5-chlorobenzo[1,2,5]oxadiazolyl |
| 915. | 3-fluoropropyl | 7-chlorobenzo[2,1,3]oxadiazol-4-yl |
| 916. | 3-fluoropropyl | benzo[2,1,3]thiadiazol-4-yl |
| 917. | 2-fluoroethyl | 4-ethylphenyl |
| 918. | 2-fluoroethyl | 4-propylphenyl |
| 919. | 2-fluoroethyl | 4-isopropylphenyl |
| 920. | 2-fluoroethyl | 4-sec-butylphenyl |
| 921. | 2-fluoroethyl | 4-isobutylphenyl |
| 922. | 2-fluoroethyl | 4-(1,1-dimethylpropyl)-phenyl |
| 923. | 2-fluoroethyl | 4-vinylphenyl |
| 924. | 2-fluoroethyl | 4-isopropenylphenyl |
| 925. | 2-fluoroethyl | 4-(fluoromethyl)phenyl |
| 926. | 2-fluoroethyl | 3-(fluoromethyl)phenyl |
| 927. | 2-fluoroethyl | 2-(fluoromethyl)phenyl |
| 928. | 2-fluoroethyl | 4-(difluoromethyl)phenyl |
| 929. | 2-fluoroethyl | 3-(difluoromethyl)phenyl |
| 930. | 2-fluoroethyl | 2-(difluoromethyl)phenyl |
| 931. | 2-fluoroethyl | 4-(trifluoromethyl)phenyl |
| 932. | 2-fluoroethyl | 3-(trifluoromethyl)phenyl |
| 933. | 2-fluoroethyl | 2-(trifluoromethyl)phenyl |
| 934. | 2-fluoroethyl | 4-(1-fluoroethyl)-phenyl |
| 935. | 2-fluoroethyl | 4-((S)-1-fluoroethyl)-phenyl |
| 936. | 2-fluoroethyl | 4-((R)-1-fluoroethyl)-phenyl |
| 937. | 2-fluoroethyl | 4-(2-fluoroethyl)-phenyl |
| 938. | 2-fluoroethyl | 4-(1,1-difluoroethyl)-phenyl |
| 939. | 2-fluoroethyl | 4-(2,2-difluoroethyl)-phenyl |
| 940. | 2-fluoroethyl | 4-(2,2,2-trifluoroethyl)-phenyl |
| 941. | 2-fluoroethyl | 4-(3-fluoropropyl)-phenyl |
| 942. | 2-fluoroethyl | 4-(2-fluoropropyl)-phenyl |
| 943. | 2-fluoroethyl | 4-((S)-2-fluoropropyl)-phenyl |
| 944. | 2-fluoroethyl | 4-((R)-2-fluoropropyl)-phenyl |
| 945. | 2-fluoroethyl | 4-(3,3-difluoropropyl)-phenyl |
| 946. | 2-fluoroethyl | 4-(3,3,3-trifluoropropyl)-phenyl |
| 947. | 2-fluoroethyl | 4-(1-fluoro-1-methylethyl)-phenyl |
| 948. | 2-fluoroethyl | 4-(2-fluoro-1-methylethyl)-phenyl |
| 949. | 2-fluoroethyl | 4-((S)-2-fluoro-1-methylethyl)-phenyl |
| 950. | 2-fluoroethyl | 4-((R)-2-fluoro-1-methylethyl)-phenyl |
| 951. | 2-fluoroethyl | 4-(2,2-difluoro-1-methylethyl)-phenyl |
| 952. | 2-fluoroethyl | 4-((S)-2,2-difluoro-1-methylethyl)-phenyl |
| 953. | 2-fluoroethyl | 4-((R)-2,2-difluoro-1-methylethyl)-phenyl |
| 954. | 2-fluoroethyl | 4-(2,2,2-trifluoro-1-methylethyl)-phenyl |
| 955. | 2-fluoroethyl | 4-((S)-2,2,2-trifluoro-1-methylethyl)-phenyl |
| 956. | 2-fluoroethyl | 4-((R)-2,2,2-trifluoro-1-methylethyl)-phenyl |
| 957. | 2-fluoroethyl | 4-(2-fluoro-1-fluoromethylethyl)-phenyl |
| 958. | 2-fluoroethyl | 4-(1-difluoromethyl-2,2-difluoroethyl)-phenyl |
| 959. | 2-fluoroethyl | 4-(1,1-dimethyl-2-fluoroethyl)-phenyl |
| 960. | 2-fluoroethyl | 4-ethoxyphenyl |
| 961. | 2-fluoroethyl | 4-propoxyphenyl |
| 962. | 2-fluoroethyl | 4-isopropoxyphenyl |
| 963. | 2-fluoroethyl | 4-butoxyphenyl |
| 964. | 2-fluoroethyl | 4-(fluoromethoxy)-phenyl |
| 965. | 2-fluoroethyl | 4-(difluoromethoxy)-phenyl |
| 966. | 2-fluoroethyl | 4-(2-fluoroethoxy)-phenyl |
| 967. | 2-fluoroethyl | 4-(2,2-difluoroethoxy)-phenyl |
| 968. | 2-fluoroethyl | 4-(2,2,2-trifluoroethoxy)-phenyl |
| 969. | 2-fluoroethyl | 4-(1,1,2,2-tetrafluoroethoxy)-phenyl |
| 970. | 2-fluoroethyl | 4-cyclopropylphenyl |

TABLE A-continued

| No. | R¹ | Ar |
|---|---|---|
| 971. | 2-fluoroethyl | 4-cyclobutylphenyl |
| 972. | 2-fluoroethyl | 4-cyclopentylphenyl |
| 973. | 2-fluoroethyl | 4-(2,2-difluorocyclopropyl)-phenyl |
| 974. | 2-fluoroethyl | 2-fluoro-4-isopropylphenyl |
| 975. | 2-fluoroethyl | 3-fluoro-4-isopropylphenyl |
| 976. | 2-fluoroethyl | 4-(1-hydroxy-1-methylethyl)-phenyl |
| 977. | 2-fluoroethyl | 4-(2-hydroxy-2-methylpropyl)-phenyl |
| 978. | 2-fluoroethyl | 4-acetylphenyl |
| 979. | 2-fluoroethyl | 4-carboxyphenyl |
| 980. | 2-fluoroethyl | 4-(O-benzyl)-phenyl |
| 981. | 2-fluoroethyl | 4-(2-methoxyethoxy)-phenyl |
| 982. | 2-fluoroethyl | 4-($CH_2$—$N(CH_3)_2$)-phenyl |
| 983. | 2-fluoroethyl | 4-(NH—CO—$NH_2$)-phenyl |
| 984. | 2-fluoroethyl | 4-(methylsulfanyl)-phenyl |
| 985. | 2-fluoroethyl | 4-(fluoromethylsulfanyl)-phenyl |
| 986. | 2-fluoroethyl | 4-(difluoromethylsulfanyl)-phenyl |
| 987. | 2-fluoroethyl | 4-(trifluoromethylsulfanyl)-phenyl |
| 988. | 2-fluoroethyl | 4-(methylsulfonyl)-phenyl |
| 989. | 2-fluoroethyl | 4-(N-methoxy-N-methyl-amino)-phenyl |
| 990. | 2-fluoroethyl | 4-(methoxyamino)-phenyl |
| 991. | 2-fluoroethyl | 4-(ethoxyamino)-phenyl |
| 992. | 2-fluoroethyl | 4-(N-methylaminooxy)-phenyl |
| 993. | 2-fluoroethyl | 4-(N,N-dimethylaminooxy)-phenyl |
| 994. | 2-fluoroethyl | 4-(azetidin-1-yl)-phenyl |
| 995. | 2-fluoroethyl | 4-(2-methylazetidin-1-yl)-phenyl |
| 996. | 2-fluoroethyl | 4-((S)-2-methylazetidin-1-yl)-phenyl |
| 997. | 2-fluoroethyl | 4-((R)-2-methylazetidin-1-yl)-phenyl |
| 998. | 2-fluoroethyl | 4-(3-fluoroazetidin-1-yl)-phenyl |
| 999. | 2-fluoroethyl | 4-(3-methoxyazetidin-1-yl)-phenyl |
| 1000. | 2-fluoroethyl | 4-(3-hydroxyazetidin-1-yl)-phenyl |
| 1001. | 2-fluoroethyl | 4-(pyrrolidin-1-yl)-phenyl |
| 1002. | 2-fluoroethyl | 4-(pyrrolidin-2-yl)-phenyl |
| 1003. | 2-fluoroethyl | 4-((S)-pyrrolidin-2-yl)-phenyl |
| 1004. | 2-fluoroethyl | 4-((R)-pyrrolidin-2-yl)-phenyl |
| 1005. | 2-fluoroethyl | 4-(pyrrolidin-3-yl)-phenyl |
| 1006. | 2-fluoroethyl | 4-((S)-pyrrolidin-3-yl)-phenyl |
| 1007. | 2-fluoroethyl | 4-((R)-pyrrolidin-3-yl)-phenyl |
| 1008. | 2-fluoroethyl | 4-(2-fluoropyrrolidin-1-yl)-phenyl |
| 1009. | 2-fluoroethyl | 4-((S)-2-fluoropyrrolidin-1-yl)-phenyl |
| 1010. | 2-fluoroethyl | 4-((R)-2-fluoropyrrolidin-1-yl)-phenyl |
| 1011. | 2-fluoroethyl | 4-(3-fluoropyrrolidin-1-yl)-phenyl |
| 1012. | 2-fluoroethyl | 4-((S)-3-fluoropyrrolidin-1-yl)-phenyl |
| 1013. | 2-fluoroethyl | 4-((R)-3-fluoropyrrolidin-1-yl)-phenyl |
| 1014. | 2-fluoroethyl | 4-(2,2-difluoropyrrolidin-1-yl)-phenyl |
| 1015. | 2-fluoroethyl | 4-(3,3-difluoropyrrolidin-1-yl)-phenyl |
| 1016. | 2-fluoroethyl | 4-(2-methylpyrrolidin-1-yl)-phenyl |
| 1017. | 2-fluoroethyl | 4-((S)-2-methylpyrrolidin-1-yl)-phenyl |
| 1018. | 2-fluoroethyl | 4-((R)-2-methylpyrrolidin-1-yl)-phenyl |
| 1019. | 2-fluoroethyl | 4-(3-methylpyrrolidin-1-yl)-phenyl |
| 1020. | 2-fluoroethyl | 4-((S)-3-methylpyrrolidin-1-yl)-phenyl |
| 1021. | 2-fluoroethyl | 4-((R)-3-methylpyrrolidin-1-yl)-phenyl |
| 1022. | 2-fluoroethyl | 4-(1-methylpyrrolidin-2-yl)-phenyl |
| 1023. | 2-fluoroethyl | 4-((S)-1-methylpyrrolidin-2-yl)-phenyl |
| 1024. | 2-fluoroethyl | 4-((R)-1-methylpyrrolidin-2-yl)-phenyl |
| 1025. | 2-fluoroethyl | 4-(1-methylpyrrolidin-3-yl)-phenyl |
| 1026. | 2-fluoroethyl | 4-((S)-1-methylpyrrolidin-3-yl)-phenyl |
| 1027. | 2-fluoroethyl | 4-((R)-1-methylpyrrolidin-3-yl)-phenyl |
| 1028. | 2-fluoroethyl | 4-(2,2-dimethylpyrrolidin-1-yl)-phenyl |
| 1029. | 2-fluoroethyl | 4-(3,3-dimethylpyrrolidin-1-yl)-phenyl |
| 1030. | 2-fluoroethyl | 4-(2-trifluoromethylpyrrolidin-1-yl)-phenyl |
| 1031. | 2-fluoroethyl | 4-((S)-2-trifluoromethylpyrrolidin-1-yl)-phenyl |
| 1032. | 2-fluoroethyl | 4-((R)-2-trifluoromethylpyrrolidin-1-yl)-phenyl |
| 1033. | 2-fluoroethyl | 4-(3-trifluoromethylpyrrolidin-1-yl)-phenyl |
| 1034. | 2-fluoroethyl | 4-((S)-3-trifluoromethylpyrrolidin-1-yl)-phenyl |
| 1035. | 2-fluoroethyl | 4-((R)-3-trifluoromethylpyrrolidin-1-yl)-phenyl |
| 1036. | 2-fluoroethyl | 4-(2-oxopyrrolidin-1-yl)-phenyl |
| 1037. | 2-fluoroethyl | 4-(2-oxo-oxazolidin-3-yl)-phenyl |
| 1038. | 2-fluoroethyl | 4-(piperidin-1-yl)-phenyl |
| 1039. | 2-fluoroethyl | 4-(2-methylpiperidin-1-yl)-phenyl |
| 1040. | 2-fluoroethyl | 4-((S)-2-methylpiperidin-1-yl)-phenyl |
| 1041. | 2-fluoroethyl | 4-((R)-2-methylpiperidin-1-yl)-phenyl |
| 1042. | 2-fluoroethyl | 4-(piperazin-1-yl)-phenyl |
| 1043. | 2-fluoroethyl | 4-(4-methylpiperazin-1-yl)-phenyl |
| 1044. | 2-fluoroethyl | 4-(morpholin-4-yl)-phenyl |
| 1045. | 2-fluoroethyl | 4-(thiomorpholin-4-yl)-phenyl |
| 1046. | 2-fluoroethyl | 4-(1-oxo-thiomorpholin-4-yl)-phenyl |
| 1047. | 2-fluoroethyl | 4-(1,1-dioxo-thiomorpholin-4-yl)-phenyl |

TABLE A-continued

| No. | R¹ | Ar |
|---|---|---|
| 1048. | 2-fluoroethyl | 4-(pyrrol-1-yl)-phenyl |
| 1049. | 2-fluoroethyl | 4-(pyrrol-2-yl)-phenyl |
| 1050. | 2-fluoroethyl | 4-(pyrrol-3-yl)-phenyl |
| 1051. | 2-fluoroethyl | 4-(1-methylpyrrol-2-yl)-phenyl |
| 1052. | 2-fluoroethyl | 4-(1-methylpyrrol-3-yl)-phenyl |
| 1053. | 2-fluoroethyl | 4-(furan-2-yl)-phenyl |
| 1054. | 2-fluoroethyl | 4-(furan-3-yl)-phenyl |
| 1055. | 2-fluoroethyl | 4-(thiophen-2-yl)-phenyl |
| 1056. | 2-fluoroethyl | 4-(thiophen-3-yl)-phenyl |
| 1057. | 2-fluoroethyl | 4-(5-propylthien-2-yl)-phenyl |
| 1058. | 2-fluoroethyl | 4-(pyrazol-1-yl)-phenyl |
| 1059. | 2-fluoroethyl | 4-(pyrazol-3-yl)-phenyl |
| 1060. | 2-fluoroethyl | 4-(pyrazol-4-yl)-phenyl |
| 1061. | 2-fluoroethyl | 4-(1-methyl-1H-pyrazol-4-yl)-phenyl |
| 1062. | 2-fluoroethyl | 4-(1-ethyl-1H-pyrazol-4-yl)-phenyl |
| 1063. | 2-fluoroethyl | 4-(1-methyl-1H-pyrazol-5-yl)-phenyl |
| 1064. | 2-fluoroethyl | 4-(1H-imidazol-2-yl)-phenyl |
| 1065. | 2-fluoroethyl | 4-(imidazol-1-yl)-phenyl |
| 1066. | 2-fluoroethyl | 4-(1-methylimidazol-2-yl)-phenyl |
| 1067. | 2-fluoroethyl | 4-(oxazol-2-yl)-phenyl |
| 1068. | 2-fluoroethyl | 4-(oxazol-4-yl)-phenyl |
| 1069. | 2-fluoroethyl | 4-(oxazol-5-yl)-phenyl |
| 1070. | 2-fluoroethyl | 4-(isoxazol-3-yl)-phenyl |
| 1071. | 2-fluoroethyl | 4-(isoxazol-4-yl)-phenyl |
| 1072. | 2-fluoroethyl | 4-(isoxazol-5-yl)-phenyl |
| 1073. | 2-fluoroethyl | 4-([1,2,3]-triazol-1-yl)-phenyl |
| 1074. | 2-fluoroethyl | 4-([1,2,4]-triazol-1-yl)-phenyl |
| 1075. | 2-fluoroethyl | 4-([1,2,3]-triazol-2-yl)-phenyl |
| 1076. | 2-fluoroethyl | 4-(4H-[1,2,4]-triazol-3-yl)-phenyl |
| 1077. | 2-fluoroethyl | 4-([1,2,4]-triazol-4-yl)-phenyl |
| 1078. | 2-fluoroethyl | 4-(2H-[1,2,3]-triazol-4-yl)-phenyl |
| 1079. | 2-fluoroethyl | 4-(4-methyl-4H-[1,2,4]-triazol-3-yl)-phenyl |
| 1080. | 2-fluoroethyl | 4-(2-methyl-2H-[1,2,3]-triazol-4-yl)-phenyl |
| 1081. | 2-fluoroethyl | 4-([1,3,4]-oxadiazol-2-yl)-phenyl |
| 1082. | 2-fluoroethyl | 4-([1,2,4]-oxadiazol-3-yl)-phenyl |
| 1083. | 2-fluoroethyl | 4-([1,2,4]-oxadiazol-5-yl)-phenyl |
| 1084. | 2-fluoroethyl | 4-([1,2,3]-oxadiazol-4-yl)-phenyl |
| 1085. | 2-fluoroethyl | 4-([1,2,3]-oxadiazol-5-yl)-phenyl |
| 1086. | 2-fluoroethyl | 4-([1,2,3]-thiadiazol-4-yl)-phenyl |
| 1087. | 2-fluoroethyl | 4-(1H-tetrazol-5-yl)-phenyl |
| 1088. | 2-fluoroethyl | 4-(tetrazol-1-yl)-phenyl |
| 1089. | 2-fluoroethyl | 4-(2-methyl-2H-tetrazol-5-yl)-phenyl |
| 1090. | 2-fluoroethyl | 4-(1-methyl-1H-tetrazol-5-yl)-phenyl |
| 1091. | 2-fluoroethyl | 4-furazan-3-yl-phenyl |
| 1092. | 2-fluoroethyl | 4-(pyrid-2-yl)-phenyl |
| 1093. | 2-fluoroethyl | 4-(pyrid-3-yl)-phenyl |
| 1094. | 2-fluoroethyl | 4-(pyrid-4-yl)-phenyl |
| 1095. | 2-fluoroethyl | 4-(pyrimidin-2-yl)-phenyl |
| 1096. | 2-fluoroethyl | 4-(pyrimidin-4-yl)-phenyl |
| 1097. | 2-fluoroethyl | 4-(pyrimidin-5-yl)-phenyl |
| 1098. | 2-fluoroethyl | 5-isopropylthiophen-2-yl |
| 1099. | 2-fluoroethyl | 2-chlorothiophen-5-yl |
| 1100. | 2-fluoroethyl | 2,5-dichlorothiophen-4-yl |
| 1101. | 2-fluoroethyl | 2,3-dichlorothiophen-5-yl |
| 1102. | 2-fluoroethyl | 2-chloro-3-nitrothiophen-5-yl |
| 1103. | 2-fluoroethyl | 2-(phenylsulfonyl)-thiophen-5-yl |
| 1104. | 2-fluoroethyl | 2-(pyridin-2-yl)thiophen-5-yl |
| 1105. | 2-fluoroethyl | 2-(5-(trifluoromethyl)isoxazol-3-yl)-thiophen-5-yl |
| 1106. | 2-fluoroethyl | 2-(2-methylthiazol-4-yl)-thiophen-5-yl |
| 1107. | 2-fluoroethyl | 1-methyl-1H-imidazol-4-yl |
| 1108. | 2-fluoroethyl | 1,2-dimethyl-1H-imidazol-4-yl |
| 1109. | 2-fluoroethyl | 3,5-dimethylisoxazol-4-yl |
| 1110. | 2-fluoroethyl | thiazol-2-yl |
| 1111. | 2-fluoroethyl | 4-methylthiazol-2-yl |
| 1112. | 2-fluoroethyl | 4-isopropylthiazol-2-yl |
| 1113. | 2-fluoroethyl | 4-trifluoromethylthiazol-2-yl |
| 1114. | 2-fluoroethyl | 5-methylthiazol-2-yl |
| 1115. | 2-fluoroethyl | 5-isopropylthiazol-2-yl |
| 1116. | 2-fluoroethyl | 5-trifluoromethylthiazol-2-yl |
| 1117. | 2-fluoroethyl | 2,4-dimethylthiazol-5-yl |
| 1118. | 2-fluoroethyl | 2-acetamido-4-methylthiazol-5-yl |
| 1119. | 2-fluoroethyl | 4H-[1,2,4]triazol-3-yl |
| 1120. | 2-fluoroethyl | 5-methyl-4H-[1,2,4]triazol-3-yl |
| 1121. | 2-fluoroethyl | 4-methyl-4H-[1,2,4]triazol-3-yl |
| 1122. | 2-fluoroethyl | 5-isopropyl-4H-[1,2,4]triazol-3-yl |
| 1123. | 2-fluoroethyl | 5-trifluoromethyl-4H-[1,2,4]triazol-3-yl |
| 1124. | 2-fluoroethyl | 4,5-dimethyl-4H-[1,2,4]triazol-3-yl |

TABLE A-continued

| No. | R¹ | Ar |
|---|---|---|
| 1125. | 2-fluoroethyl | 5-isopropyl-4-methyl-4H-[1,2,4]triazol-3-yl |
| 1126. | 2-fluoroethyl | 5-trifluoromethyl-4-methyl-4H-[1,2,4]triazol-3-yl |
| 1127. | 2-fluoroethyl | [1,3,4]thiadiazol-2-yl |
| 1128. | 2-fluoroethyl | 5-methyl-[1,3,4]thiadiazol-2-yl |
| 1129. | 2-fluoroethyl | 5-isopropyl-[1,3,4]thiadiazol-2-yl |
| 1130. | 2-fluoroethyl | 5-trifluoromethyl-[1,3,4]thiadiazol-2-yl |
| 1131. | 2-fluoroethyl | 3-bromo-2-chloropyrid-5-yl |
| 1132. | 2-fluoroethyl | 2-(4-morpholino)-pyrid-5-yl |
| 1133. | 2-fluoroethyl | 2-phenoxypyrid-5-yl |
| 1134. | 2-fluoroethyl | (2-isopropyl)-pyrimidin-5-yl |
| 1135. | 2-fluoroethyl | (5-isopropyl)-pyrimidin-2-yl |
| 1136. | 2-fluoroethyl | 8-quinolyl |
| 1137. | 2-fluoroethyl | 5-isoquinolyl |
| 1138. | 2-fluoroethyl | 2-(2,2,2-trifluoroacetyl)-1,2,3,4-tetrahydroisoquinolin-7-yl |
| 1139. | 2-fluoroethyl | 5-chloro-3-methylbenzothiophen-2-yl |
| 1140. | 2-fluoroethyl | 3,4-dihydro-4-methyl-2H-benzo[b][1,4]oxazinyl |
| 1141. | 2-fluoroethyl | benzothiazol-6-yl |
| 1142. | 2-fluoroethyl | benzo[2,1,3]oxadiazol-4-yl |
| 1143. | 2-fluoroethyl | 5-chlorobenzo[1,2,5]oxadiazolyl |
| 1144. | 2-fluoroethyl | 7-chlorobenzo[2,1,3]oxadiazol-4-yl |
| 1145. | 2-fluoroethyl | benzo[2,1,3]thiadiazol-4-yl |
| 1146. | cyclopropylmethyl | 4-ethylphenyl |
| 1147. | cyclopropylmethyl | 4-propylphenyl |
| 1148. | cyclopropylmethyl | 4-isopropylphenyl |
| 1149. | cyclopropylmethyl | 4-sec-butylphenyl |
| 1150. | cyclopropylmethyl | 4-isobutylphenyl |
| 1151. | cyclopropylmethyl | 4-(1,1-dimethylpropyl)-phenyl |
| 1152. | cyclopropylmethyl | 4-vinylphenyl |
| 1153. | cyclopropylmethyl | 4-isopropenylphenyl |
| 1154. | cyclopropylmethyl | 4-(fluoromethyl)phenyl |
| 1155. | cyclopropylmethyl | 3-(fluoromethyl)phenyl |
| 1156. | cyclopropylmethyl | 2-(fluoromethyl)phenyl |
| 1157. | cyclopropylmethyl | 4-(difluoromethyl)phenyl |
| 1158. | cyclopropylmethyl | 3-(difluoromethyl)phenyl |
| 1159. | cyclopropylmethyl | 2-(difluoromethyl)phenyl |
| 1160. | cyclopropylmethyl | 4-(trifluoromethyl)phenyl |
| 1161. | cyclopropylmethyl | 3-(trifluoromethyl)phenyl |
| 1162. | cyclopropylmethyl | 2-(trifluoromethyl)phenyl |
| 1163. | cyclopropylmethyl | 4-(1-fluoroethyl)-phenyl |
| 1164. | cyclopropylmethyl | 4-((S)-1-fluoroethyl)-phenyl |
| 1165. | cyclopropylmethyl | 4-((R)-1-fluoroethyl)-phenyl |
| 1166. | cyclopropylmethyl | 4-(2-fluoroethyl)-phenyl |
| 1167. | cyclopropylmethyl | 4-(1,1-difluoroethyl)-phenyl |
| 1168. | cyclopropylmethyl | 4-(2,2-difluoroethyl)-phenyl |
| 1169. | cyclopropylmethyl | 4-(2,2,2-trifluoroethyl)-phenyl |
| 1170. | cyclopropylmethyl | 4-(3-fluoropropyl)-phenyl |
| 1171. | cyclopropylmethyl | 4-(2-fluoropropyl)-phenyl |
| 1172. | cyclopropylmethyl | 4-((S)-2-fluoropropyl)-phenyl |
| 1173. | cyclopropylmethyl | 4-((R)-2-fluoropropyl)-phenyl |
| 1174. | cyclopropylmethyl | 4-(3,3-difluoropropyl)-phenyl |
| 1175. | cyclopropylmethyl | 4-(3,3,3-trifluoropropyl)-phenyl |
| 1176. | cyclopropylmethyl | 4-(1-fluoro-1-methylethyl)-phenyl |
| 1177. | cyclopropylmethyl | 4-(2-fluoro-1-methylethyl)-phenyl |
| 1178. | cyclopropylmethyl | 4-((S)-2-fluoro-1-methylethyl)-phenyl |
| 1179. | cyclopropylmethyl | 4-((R)-2-fluoro-1-methylethyl)-phenyl |
| 1180. | cyclopropylmethyl | 4-(2,2-difluoro-1-methylethyl)-phenyl |
| 1181. | cyclopropylmethyl | 4-((S)-2,2-difluoro-1-methylethyl)-phenyl |
| 1182. | cyclopropylmethyl | 4-((R)-2,2-difluoro-1-methylethyl)-phenyl |
| 1183. | cyclopropylmethyl | 4-(2,2,2-trifluoro-1-methylethyl)-phenyl |
| 1184. | cyclopropylmethyl | 4-((S)-2,2,2-trifluoro-1-methylethyl)-phenyl |
| 1185. | cyclopropylmethyl | 4-((R)-2,2,2-trifluoro-1-methylethyl)-phenyl |
| 1186. | cyclopropylmethyl | 4-(2-fluoro-1-fluoromethylethyl)-phenyl |
| 1187. | cyclopropylmethyl | 4-(1-difluoromethyl-2,2-difluoroethyl)-phenyl |
| 1188. | cyclopropylmethyl | 4-(1,1-dimethyl-2-fluoroethyl)-phenyl |
| 1189. | cyclopropylmethyl | 4-ethoxyphenyl |
| 1190. | cyclopropylmethyl | 4-propoxyphenyl |
| 1191. | cyclopropylmethyl | 4-isopropoxyphenyl |
| 1192. | cyclopropylmethyl | 4-butoxyphenyl |
| 1193. | cyclopropylmethyl | 4-(fluoromethoxy)-phenyl |
| 1194. | cyclopropylmethyl | 4-(difluoromethoxy)-phenyl |
| 1195. | cyclopropylmethyl | 4-(2-fluoroethoxy)-phenyl |
| 1196. | cyclopropylmethyl | 4-(2,2-difluoroethoxy)-phenyl |
| 1197. | cyclopropylmethyl | 4-(2,2,2-trifluoroethoxy)-phenyl |
| 1198. | cyclopropylmethyl | 4-(1,1,2,2-tetrafluoroethoxy)-phenyl |
| 1199. | cyclopropylmethyl | 4-cyclopropylphenyl |
| 1200. | cyclopropylmethyl | 4-cyclobutylphenyl |

TABLE A-continued

| No. | R¹ | Ar |
|---|---|---|
| 1201. | cyclopropylmethyl | 4-cyclopentylphenyl |
| 1202. | cyclopropylmethyl | 4-(2,2-difluorocyclopropyl)-phenyl |
| 1203. | cyclopropylmethyl | 2-fluoro-4-isopropylphenyl |
| 1204. | cyclopropylmethyl | 3-fluoro-4-isopropylphenyl |
| 1205. | cyclopropylmethyl | 4-(1-hydroxy-1-methylethyl)-phenyl |
| 1206. | cyclopropylmethyl | 4-(2-hydroxy-2-methylpropyl)-phenyl |
| 1207. | cyclopropylmethyl | 4-acetylphenyl |
| 1208. | cyclopropylmethyl | 4-carboxyphenyl |
| 1209. | cyclopropylmethyl | 4-(O-benzyl)-phenyl |
| 1210. | cyclopropylmethyl | 4-(2-methoxyethoxy)-phenyl |
| 1211. | cyclopropylmethyl | 4-(CH$_2$—N(CH$_3$)$_2$)-phenyl |
| 1212. | cyclopropylmethyl | 4-(NH—CO—NH$_2$)-phenyl |
| 1213. | cyclopropylmethyl | 4-(methylsulfanyl)-phenyl |
| 1214. | cyclopropylmethyl | 4-(fluoromethylsulfanyl)-phenyl |
| 1215. | cyclopropylmethyl | 4-(difluoromethylsulfanyl)-phenyl |
| 1216. | cyclopropylmethyl | 4-(trifluoromethylsulfanyl)-phenyl |
| 1217. | cyclopropylmethyl | 4-(methylsulfonyl)-phenyl |
| 1218. | cyclopropylmethyl | 4-(N-methoxy-N-methyl-amino)-phenyl |
| 1219. | cyclopropylmethyl | 4-(methoxyamino)-phenyl |
| 1220. | cyclopropylmethyl | 4-(ethoxyamino)-phenyl |
| 1221. | cyclopropylmethyl | 4-(N-methylaminooxy)-phenyl |
| 1222. | cyclopropylmethyl | 4-(N,N-dimethylaminooxy)-phenyl |
| 1223. | cyclopropylmethyl | 4-(azetidin-1-yl)-phenyl |
| 1224. | cyclopropylmethyl | 4-(2-methylazetidin-1-yl)-phenyl |
| 1225. | cyclopropylmethyl | 4-((S)-2-methylazetidin-1-yl)-phenyl |
| 1226. | cyclopropylmethyl | 4-((R)-2-methylazetidin-1-yl)-phenyl |
| 1227. | cyclopropylmethyl | 4-(3-fluoroazetidin-1-yl)-phenyl |
| 1228. | cyclopropylmethyl | 4-(3-methoxyazetidin-1-yl)-phenyl |
| 1229. | cyclopropylmethyl | 4-(3-hydroxyazetidin-1-yl)-phenyl |
| 1230. | cyclopropylmethyl | 4-(pyrrolidin-1-yl)-phenyl |
| 1231. | cyclopropylmethyl | 4-(pyrrolidin-2-yl)-phenyl |
| 1232. | cyclopropylmethyl | 4-((S)-pyrrolidin-2-yl)-phenyl |
| 1233. | cyclopropylmethyl | 4-((R)-pyrrolidin-2-yl)-phenyl |
| 1234. | cyclopropylmethyl | 4-(pyrrolidin-3-yl)-phenyl |
| 1235. | cyclopropylmethyl | 4-((S)-pyrrolidin-3-yl)-phenyl |
| 1236. | cyclopropylmethyl | 4-((R)-pyrrolidin-3-yl)-phenyl |
| 1237. | cyclopropylmethyl | 4-(2-fluoropyrrolidin-1-yl)-phenyl |
| 1238. | cyclopropylmethyl | 4-((S)-2-fluoropyrrolidin-1-yl)-phenyl |
| 1239. | cyclopropylmethyl | 4-((R)-2-fluoropyrrolidin-1-yl)-phenyl |
| 1240. | cyclopropylmethyl | 4-(3-fluoropyrrolidin-1-yl)-phenyl |
| 1241. | cyclopropylmethyl | 4-((S)-3-fluoropyrrolidin-1-yl)-phenyl |
| 1242. | cyclopropylmethyl | 4-((R)-3-fluoropyrrolidin-1-yl)-phenyl |
| 1243. | cyclopropylmethyl | 4-(2,2-difluoropyrrolidin-1-yl)-phenyl |
| 1244. | cyclopropylmethyl | 4-(3,3-difluoropyrrolidin-1-yl)-phenyl |
| 1245. | cyclopropylmethyl | 4-(2-methylpyrrolidin-1-yl)-phenyl |
| 1246. | cyclopropylmethyl | 4-((S)-2-methylpyrrolidin-1-yl)-phenyl |
| 1247. | cyclopropylmethyl | 4-((R)-2-methylpyrrolidin-1-yl)-phenyl |
| 1248. | cyclopropylmethyl | 4-(3-methylpyrrolidin-1-yl)-phenyl |
| 1249. | cyclopropylmethyl | 4-((S)-3-methylpyrrolidin-1-yl)-phenyl |
| 1250. | cyclopropylmethyl | 4-((R)-3-methylpyrrolidin-1-yl)-phenyl |
| 1251. | cyclopropylmethyl | 4-(1-methylpyrrolidin-2-yl)-phenyl |
| 1252. | cyclopropylmethyl | 4-((S)-1-methylpyrrolidin-2-yl)-phenyl |
| 1253. | cyclopropylmethyl | 4-((R)-1-methylpyrrolidin-2-yl)-phenyl |
| 1254. | cyclopropylmethyl | 4-(1-methylpyrrolidin-3-yl)-phenyl |
| 1255. | cyclopropylmethyl | 4-((S)-1-methylpyrrolidin-3-yl)-phenyl |
| 1256. | cyclopropylmethyl | 4-((R)-1-methylpyrrolidin-3-yl)-phenyl |
| 1257. | cyclopropylmethyl | 4-(2,2-dimethylpyrrolidin-1-yl)-phenyl |
| 1258. | cyclopropylmethyl | 4-(3,3-dimethylpyrrolidin-1-yl)-phenyl |
| 1259. | cyclopropylmethyl | 4-(2-trifluoromethylpyrrolidin-1-yl)-phenyl |
| 1260. | cyclopropylmethyl | 4-((S)-2-trifluoromethylpyrrolidin-1-yl)-phenyl |
| 1261. | cyclopropylmethyl | 4-((R)-2-trifluoromethylpyrrolidin-1-yl)-phenyl |
| 1262. | cyclopropylmethyl | 4-(3-trifluoromethylpyrrolidin-1-yl)-phenyl |
| 1263. | cyclopropylmethyl | 4-((S)-3-trifluoromethylpyrrolidin-1-yl)-phenyl |
| 1264. | cyclopropylmethyl | 4-((R)-3-trifluoromethylpyrrolidin-1-yl)-phenyl |
| 1265. | cyclopropylmethyl | 4-(2-oxopyrrolidin-1-yl)-phenyl |
| 1266. | cyclopropylmethyl | 4-(2-oxo-oxazolidin-3-yl)-phenyl |
| 1267. | cyclopropylmethyl | 4-(piperidin-1-yl)-phenyl |
| 1268. | cyclopropylmethyl | 4-(2-methylpiperidin-1-yl)-phenyl |
| 1269. | cyclopropylmethyl | 4-((S)-2-methylpiperidin-1-yl)-phenyl |
| 1270. | cyclopropylmethyl | 4-((R)-2-methylpiperidin-1-yl)-phenyl |
| 1271. | cyclopropylmethyl | 4-(piperazin-1-yl)-phenyl |
| 1272. | cyclopropylmethyl | 4-(4-methylpiperazin-1-yl)-phenyl |
| 1273. | cyclopropylmethyl | 4-(morpholin-4-yl)-phenyl |
| 1274. | cyclopropylmethyl | 4-(thiomorpholin-4-yl)-phenyl |
| 1275. | cyclopropylmethyl | 4-(1-oxo-thiomorpholin-4-yl)-phenyl |
| 1276. | cyclopropylmethyl | 4-(1,1-dioxo-thiomorpholin-4-yl)-phenyl |
| 1277. | cyclopropylmethyl | 4-(pyrrol-1-yl)-phenyl |

TABLE A-continued

| No. | R¹ | Ar |
|---|---|---|
| 1278. | cyclopropylmethyl | 4-(pyrrol-2-yl)-phenyl |
| 1279. | cyclopropylmethyl | 4-(pyrrol-3-yl)-phenyl |
| 1280. | cyclopropylmethyl | 4-(1-methylpyrrol-2-yl)-phenyl |
| 1281. | cyclopropylmethyl | 4-(1-methylpyrrol-3-yl)-phenyl |
| 1282. | cyclopropylmethyl | 4-(furan-2-yl)-phenyl |
| 1283. | cyclopropylmethyl | 4-(furan-3-yl)-phenyl |
| 1284. | cyclopropylmethyl | 4-(thiophen-2-yl)-phenyl |
| 1285. | cyclopropylmethyl | 4-(thiophen-3-yl)-phenyl |
| 1286. | cyclopropylmethyl | 4-(5-propylthien-2-yl)-phenyl |
| 1287. | cyclopropylmethyl | 4-(pyrazol-1-yl)-phenyl |
| 1288. | cyclopropylmethyl | 4-(pyrazol-3-yl)-phenyl |
| 1289. | cyclopropylmethyl | 4-(pyrazol-4-yl)-phenyl |
| 1290. | cyclopropylmethyl | 4-(1-methyl-1H-pyrazol-4-yl)-phenyl |
| 1291. | cyclopropylmethyl | 4-(1-ethyl-1H-pyrazol-4-yl)-phenyl |
| 1292. | cyclopropylmethyl | 4-(1-methyl-1H-pyrazol-5-yl)-phenyl |
| 1293. | cyclopropylmethyl | 4-(1H-imidazol-2-yl)-phenyl |
| 1294. | cyclopropylmethyl | 4-(imidazol-1-yl)-phenyl |
| 1295. | cyclopropylmethyl | 4-(1-methylimidazol-2-yl)-phenyl |
| 1296. | cyclopropylmethyl | 4-(oxazol-2-yl)-phenyl |
| 1297. | cyclopropylmethyl | 4-(oxazol-4-yl)-phenyl |
| 1298. | cyclopropylmethyl | 4-(oxazol-5-yl)-phenyl |
| 1299. | cyclopropylmethyl | 4-(isoxazol-3-yl)-phenyl |
| 1300. | cyclopropylmethyl | 4-(isoxazol-4-yl)-phenyl |
| 1301. | cyclopropylmethyl | 4-(isoxazol-5-yl)-phenyl |
| 1302. | cyclopropylmethyl | 4-([1,2,3]-triazol-1-yl)-phenyl |
| 1303. | cyclopropylmethyl | 4-([1,2,4]-triazol-1-yl)-phenyl |
| 1304. | cyclopropylmethyl | 4-([1,2,3]-triazol-2-yl)-phenyl |
| 1305. | cyclopropylmethyl | 4-(4H-[1,2,4]-triazol-3-yl)-phenyl |
| 1306. | cyclopropylmethyl | 4-([1,2,4]-triazol-4-yl)-phenyl |
| 1307. | cyclopropylmethyl | 4-(2H-[1,2,3]-triazol-4-yl)-phenyl |
| 1308. | cyclopropylmethyl | 4-(4-methyl-4H-[1,2,4]-triazol-3-yl)-phenyl |
| 1309. | cyclopropylmethyl | 4-(2-methyl-2H-[1,2,3]-triazol-4-yl)-phenyl |
| 1310. | cyclopropylmethyl | 4-([1,3,4]-oxadiazol-2-yl)-phenyl |
| 1311. | cyclopropylmethyl | 4-([1,2,4]-oxadiazol-3-yl)-phenyl |
| 1312. | cyclopropylmethyl | 4-([1,2,4]-oxadiazol-5-yl)-phenyl |
| 1313. | cyclopropylmethyl | 4-([1,2,3]-oxadiazol-4-yl)-phenyl |
| 1314. | cyclopropylmethyl | 4-([1,2,3]-oxadiazol-5-yl)-phenyl |
| 1315. | cyclopropylmethyl | 4-([1,2,3]-thiadiazol-4-yl)-phenyl |
| 1316. | cyclopropylmethyl | 4-(1H-tetrazol-5-yl)-phenyl |
| 1317. | cyclopropylmethyl | 4-(tetrazol-1-yl)-phenyl |
| 1318. | cyclopropylmethyl | 4-(2-methyl-2H-tetrazol-5-yl)-phenyl |
| 1319. | cyclopropylmethyl | 4-(1-methyl-1H-tetrazol-5-yl)-phenyl |
| 1320. | cyclopropylmethyl | 4-furazan-3-yl-phenyl |
| 1321. | cyclopropylmethyl | 4-(pyrid-2-yl)-phenyl |
| 1322. | cyclopropylmethyl | 4-(pyrid-3-yl)-phenyl |
| 1323. | cyclopropylmethyl | 4-(pyrid-4-yl)-phenyl |
| 1324. | cyclopropylmethyl | 4-(pyrimidin-2-yl)-phenyl |
| 1325. | cyclopropylmethyl | 4-(pyrimidin-4-yl)-phenyl |
| 1326. | cyclopropylmethyl | 4-(pyrimidin-5-yl)-phenyl |
| 1327. | cyclopropylmethyl | 5-isopropylthiophen-2-yl |
| 1328. | cyclopropylmethyl | 2-chlorothiophen-5-yl |
| 1329. | cyclopropylmethyl | 2,5-dichlorothiophen-4-yl |
| 1330. | cyclopropylmethyl | 2,3-dichlorothiophen-5-yl |
| 1331. | cyclopropylmethyl | 2-chloro-3-nitrothiophen-5-yl |
| 1332. | cyclopropylmethyl | 2-(phenylsulfonyl)-thiophen-5-yl |
| 1333. | cyclopropylmethyl | 2-(pyridin-2-yl)thiophen-5-yl |
| 1334. | cyclopropylmethyl | 2-(5-(trifluoromethyl)isoxazol-3-yl)-thiophen-5-yl |
| 1335. | cyclopropylmethyl | 2-(2-methylthiazol-4-yl)-thiophen-5-yl |
| 1336. | cyclopropylmethyl | 1-methyl-1H-imidazol-4-yl |
| 1337. | cyclopropylmethyl | 1,2-dimethyl-1H-imidazol-4-yl |
| 1338. | cyclopropylmethyl | 3,5-dimethylisoxazol-4-yl |
| 1339. | cyclopropylmethyl | thiazol-2-yl |
| 1340. | cyclopropylmethyl | 4-methylthiazol-2-yl |
| 1341. | cyclopropylmethyl | 4-isopropylthiazol-2-yl |
| 1342. | cyclopropylmethyl | 4-trifluoromethylthiazol-2-yl |
| 1343. | cyclopropylmethyl | 5-methylthiazol-2-yl |
| 1344. | cyclopropylmethyl | 5-isopropylthiazol-2-yl |
| 1345. | cyclopropylmethyl | 5-trifluoromethylthiazol-2-yl |
| 1346. | cyclopropylmethyl | 2,4-dimethylthiazol-5-yl |
| 1347. | cyclopropylmethyl | 2-acetamido-4-methylthiazol-5-yl |
| 1348. | cyclopropylmethyl | 4H-[1,2,4]triazol-3-yl |
| 1349. | cyclopropylmethyl | 5-methyl-4H-[1,2,4]triazol-3-yl |
| 1350. | cyclopropylmethyl | 4-methyl-4H-[1,2,4]triazol-3-yl |
| 1351. | cyclopropylmethyl | 5-isopropyl-4H-[1,2,4]triazol-3-yl |
| 1352. | cyclopropylmethyl | 5-trifluoromethyl-4H-[1,2,4]triazol-3-yl |
| 1353. | cyclopropylmethyl | 4,5-dimethyl-4H-[1,2,4]triazol-3-yl |
| 1354. | cyclopropylmethyl | 5-isopropyl-4-methyl-4H-[1,2,4]triazol-3-yl |

TABLE A-continued

| No. | R¹ | Ar |
|---|---|---|
| 1355. | cyclopropylmethyl | 5-trifluoromethyl-4-methyl-4H-[1,2,4]triazol-3-yl |
| 1356. | cyclopropylmethyl | [1,3,4]thiadiazol-2-yl |
| 1357. | cyclopropylmethyl | 5-methyl-[1,3,4]thiadiazol-2-yl |
| 1358. | cyclopropylmethyl | 5-isopropyl-[1,3,4]thiadiazol-2-yl |
| 1359. | cyclopropylmethyl | 5-trifluoromethyl-[1,3,4]thiadiazol-2-yl |
| 1360. | cyclopropylmethyl | 3-bromo-2-chloropyrid-5-yl |
| 1361. | cyclopropylmethyl | 2-(4-morpholino)-pyrid-5-yl |
| 1362. | cyclopropylmethyl | 2-phenoxypyrid-5-yl |
| 1363. | cyclopropylmethyl | (2-isopropyl)-pyrimidin-5-yl |
| 1364. | cyclopropylmethyl | (5-isopropyl)-pyrimidin-2-yl |
| 1365. | cyclopropylmethyl | 8-quinolyl |
| 1366. | cyclopropylmethyl | 5-isoquinolyl |
| 1367. | cyclopropylmethyl | 2-(2,2,2-trifluoroacetyl)-1,2,3,4-tetrahydroisoquinolin-7-yl |
| 1368. | cyclopropylmethyl | 5-chloro-3-methylbenzothiophen-2-yl |
| 1369. | cyclopropylmethyl | 3,4-dihydro-4-methyl-2H-benzo[b][1,4]oxazinyl |
| 1370. | cyclopropylmethyl | benzothiazol-6-yl |
| 1371. | cyclopropylmethyl | benzo[2,1,3]oxadiazol-4-yl |
| 1372. | cyclopropylmethyl | 5-chlorobenzo[1,2,5]oxadiazolyl |
| 1373. | cyclopropylmethyl | 7-chlorobenzo[2,1,3]oxadiazol-4-yl |
| 1374. | cyclopropylmethyl | benzo[2,1,3]thiadiazol-4-yl |
| 1375. | 1-propen-3-yl | 4-ethylphenyl |
| 1376. | 1-propen-3-yl | 4-propylphenyl |
| 1377. | 1-propen-3-yl | 4-isopropylphenyl |
| 1378. | 1-propen-3-yl | 4-sec-butylphenyl |
| 1379. | 1-propen-3-yl | 4-isobutylphenyl |
| 1380. | 1-propen-3-yl | 4-(1,1-dimethylpropyl)-phenyl |
| 1381. | 1-propen-3-yl | 4-vinylphenyl |
| 1382. | 1-propen-3-yl | 4-isopropenylphenyl |
| 1383. | 1-propen-3-yl | 4-(fluoromethyl)phenyl |
| 1384. | 1-propen-3-yl | 3-(fluoromethyl)phenyl |
| 1385. | 1-propen-3-yl | 2-(fluoromethyl)phenyl |
| 1386. | 1-propen-3-yl | 4-(difluoromethyl)phenyl |
| 1387. | 1-propen-3-yl | 3-(difluoromethyl)phenyl |
| 1388. | 1-propen-3-yl | 2-(difluoromethyl)phenyl |
| 1389. | 1-propen-3-yl | 4-(trifluoromethyl)phenyl |
| 1390. | 1-propen-3-yl | 3-(trifluoromethyl)phenyl |
| 1391. | 1-propen-3-yl | 2-(trifluoromethyl)phenyl |
| 1392. | 1-propen-3-yl | 4-(1-fluoroethyl)-phenyl |
| 1393. | 1-propen-3-yl | 4-((S)-1-fluoroethyl)-phenyl |
| 1394. | 1-propen-3-yl | 4-((R)-1-fluoroethyl)-phenyl |
| 1395. | 1-propen-3-yl | 4-(2-fluoroethyl)-phenyl |
| 1396. | 1-propen-3-yl | 4-(1,1-difluoroethyl)-phenyl |
| 1397. | 1-propen-3-yl | 4-(2,2-difluoroethyl)-phenyl |
| 1398. | 1-propen-3-yl | 4-(2,2,2-trifluoroethyl)-phenyl |
| 1399. | 1-propen-3-yl | 4-(3-fluoropropyl)-phenyl |
| 1400. | 1-propen-3-yl | 4-(2-fluoropropyl)-phenyl |
| 1401. | 1-propen-3-yl | 4-((S)-2-fluoropropyl)-phenyl |
| 1402. | 1-propen-3-yl | 4-((R)-2-fluoropropyl)-phenyl |
| 1403. | 1-propen-3-yl | 4-(3,3-difluoropropyl)-phenyl |
| 1404. | 1-propen-3-yl | 4-(3,3,3-trifluoropropyl)-phenyl |
| 1405. | 1-propen-3-yl | 4-(1-fluoro-1-methylethyl)-phenyl |
| 1406. | 1-propen-3-yl | 4-(2-fluoro-1-methylethyl)-phenyl |
| 1407. | 1-propen-3-yl | 4-((S)-2-fluoro-1-methylethyl)-phenyl |
| 1408. | 1-propen-3-yl | 4-((R)-2-fluoro-1-methylethyl)-phenyl |
| 1409. | 1-propen-3-yl | 4-(2,2-difluoro-1-methylethyl)-phenyl |
| 1410. | 1-propen-3-yl | 4-((S)-2,2-difluoro-1-methylethyl)-phenyl |
| 1411. | 1-propen-3-yl | 4-((R)-2,2-difluoro-1-methylethyl)-phenyl |
| 1412. | 1-propen-3-yl | 4-(2,2,2-trifluoro-1-methylethyl)-phenyl |
| 1413. | 1-propen-3-yl | 4-((S)-2,2,2-trifluoro-1-methylethyl)-phenyl |
| 1414. | 1-propen-3-yl | 4-((R)-2,2,2-trifluoro-1-methylethyl)-phenyl |
| 1415. | 1-propen-3-yl | 4-(2-fluoro-1-fluoromethylethyl)-phenyl |
| 1416. | 1-propen-3-yl | 4-(1-difluoromethyl-2,2-difluoroethyl)-phenyl |
| 1417. | 1-propen-3-yl | 4-(1,1-dimethyl-2-fluoroethyl)-phenyl |
| 1418. | 1-propen-3-yl | 4-ethoxyphenyl |
| 1419. | 1-propen-3-yl | 4-propoxyphenyl |
| 1420. | 1-propen-3-yl | 4-isopropoxyphenyl |
| 1421. | 1-propen-3-yl | 4-butoxyphenyl |
| 1422. | 1-propen-3-yl | 4-(fluoromethoxy)-phenyl |
| 1423. | 1-propen-3-yl | 4-(difluoromethoxy)-phenyl |
| 1424. | 1-propen-3-yl | 4-(2-fluoroethoxy)-phenyl |
| 1425. | 1-propen-3-yl | 4-(2,2-difluoroethoxy)-phenyl |
| 1426. | 1-propen-3-yl | 4-(2,2,2-trifluoroethoxy)-phenyl |
| 1427. | 1-propen-3-yl | 4-(1,1,2,2-tetrafluoroethoxy)-phenyl |
| 1428. | 1-propen-3-yl | 4-cyclopropylphenyl |
| 1429. | 1-propen-3-yl | 4-cyclobutylphenyl |
| 1430. | 1-propen-3-yl | 4-cyclopentylphenyl |

TABLE A-continued

| No. | R¹ | Ar |
|---|---|---|
| 1431. | 1-propen-3-yl | 4-(2,2-difluorocyclopropyl)-phenyl |
| 1432. | 1-propen-3-yl | 2-fluoro-4-isopropylphenyl |
| 1433. | 1-propen-3-yl | 3-fluoro-4-isopropylphenyl |
| 1434. | 1-propen-3-yl | 4-(1-hydroxy-1-methylethyl)-phenyl |
| 1435. | 1-propen-3-yl | 4-(2-hydroxy-2-methylpropyl)-phenyl |
| 1436. | 1-propen-3-yl | 4-acetylphenyl |
| 1437. | 1-propen-3-yl | 4-carboxyphenyl |
| 1438. | 1-propen-3-yl | 4-(O-benzyl)-phenyl |
| 1439. | 1-propen-3-yl | 4-(2-methoxyethoxy)-phenyl |
| 1440. | 1-propen-3-yl | 4-(CH$_2$—N(CH$_3$)$_2$)-phenyl |
| 1441. | 1-propen-3-yl | 4-(NH—CO—NH$_2$)-phenyl |
| 1442. | 1-propen-3-yl | 4-(methylsulfanyl)-phenyl |
| 1443. | 1-propen-3-yl | 4-(fluoromethylsulfanyl)-phenyl |
| 1444. | 1-propen-3-yl | 4-(difluoromethylsulfanyl)-phenyl |
| 1445. | 1-propen-3-yl | 4-(trifluoromethylsulfanyl)-phenyl |
| 1446. | 1-propen-3-yl | 4-(methylsulfonyl)-phenyl |
| 1447. | 1-propen-3-yl | 4-(N-methoxy-N-methyl-amino)-phenyl |
| 1448. | 1-propen-3-yl | 4-(methoxyamino)-phenyl |
| 1449. | 1-propen-3-yl | 4-(ethoxyamino)-phenyl |
| 1450. | 1-propen-3-yl | 4-(N-methylaminooxy)-phenyl |
| 1451. | 1-propen-3-yl | 4-(N,N-dimethylaminooxy)-phenyl |
| 1452. | 1-propen-3-yl | 4-(azetidin-1-yl)-phenyl |
| 1453. | 1-propen-3-yl | 4-(2-methylazetidin-1-yl)-phenyl |
| 1454. | 1-propen-3-yl | 4-((S)-2-methylazetidin-1-yl)-phenyl |
| 1455. | 1-propen-3-yl | 4-((R)-2-methylazetidin-1-yl)-phenyl |
| 1456. | 1-propen-3-yl | 4-(3-fluoroazetidin-1-yl)-phenyl |
| 1457. | 1-propen-3-yl | 4-(3-methoxyazetidin-1-yl)-phenyl |
| 1458. | 1-propen-3-yl | 4-(3-hydroxyazetidin-1-yl)-phenyl |
| 1459. | 1-propen-3-yl | 4-(pyrrolidin-1-yl)-phenyl |
| 1460. | 1-propen-3-yl | 4-(pyrrolidin-2-yl)-phenyl |
| 1461. | 1-propen-3-yl | 4-((S)-pyrrolidin-2-yl)-phenyl |
| 1462. | 1-propen-3-yl | 4-((R)-pyrrolidin-2-yl)-phenyl |
| 1463. | 1-propen-3-yl | 4-(pyrrolidin-3-yl)-phenyl |
| 1464. | 1-propen-3-yl | 4-((S)-pyrrolidin-3-yl)-phenyl |
| 1465. | 1-propen-3-yl | 4-((R)-pyrrolidin-3-yl)-phenyl |
| 1466. | 1-propen-3-yl | 4-(2-fluoropyrrolidin-1-yl)-phenyl |
| 1467. | 1-propen-3-yl | 4-((S)-2-fluoropyrrolidin-1-yl)-phenyl |
| 1468. | 1-propen-3-yl | 4-((R)-2-fluoropyrrolidin-1-yl)-phenyl |
| 1469. | 1-propen-3-yl | 4-(3-fluoropyrrolidin-1-yl)-phenyl |
| 1470. | 1-propen-3-yl | 4-((S)-3-fluoropyrrolidin-1-yl)-phenyl |
| 1471. | 1-propen-3-yl | 4-((R)-3-fluoropyrrolidin-1-yl)-phenyl |
| 1472. | 1-propen-3-yl | 4-(2,2-difluoropyrrolidin-1-yl)-phenyl |
| 1473. | 1-propen-3-yl | 4-(3,3-difluoropyrrolidin-1-yl)-phenyl |
| 1474. | 1-propen-3-yl | 4-(2-methylpyrrolidin-1-yl)-phenyl |
| 1475. | 1-propen-3-yl | 4-((S)-2-methylpyrrolidin-1-yl)-phenyl |
| 1476. | 1-propen-3-yl | 4-((R)-2-methylpyrrolidin-1-yl)-phenyl |
| 1477. | 1-propen-3-yl | 4-(3-methylpyrrolidin-1-yl)-phenyl |
| 1478. | 1-propen-3-yl | 4-((S)-3-methylpyrrolidin-1-yl)-phenyl |
| 1479. | 1-propen-3-yl | 4-((R)-3-methylpyrrolidin-1-yl)-phenyl |
| 1480. | 1-propen-3-yl | 4-(1-methylpyrrolidin-2-yl)-phenyl |
| 1481. | 1-propen-3-yl | 4-((S)-1-methylpyrrolidin-2-yl)-phenyl |
| 1482. | 1-propen-3-yl | 4-((R)-1-methylpyrrolidin-2-yl)-phenyl |
| 1483. | 1-propen-3-yl | 4-(1-methylpyrrolidin-3-yl)-phenyl |
| 1484. | 1-propen-3-yl | 4-((S)-1-methylpyrrolidin-3-yl)-phenyl |
| 1485. | 1-propen-3-yl | 4-((R)-1-methylpyrrolidin-3-yl)-phenyl |
| 1486. | 1-propen-3-yl | 4-(2,2-dimethylpyrrolidin-1-yl)-phenyl |
| 1487. | 1-propen-3-yl | 4-(3,3-dimethylpyrrolidin-1-yl)-phenyl |
| 1488. | 1-propen-3-yl | 4-(2-trifluoromethylpyrrolidin-1-yl)-phenyl |
| 1489. | 1-propen-3-yl | 4-((S)-2-trifluoromethylpyrrolidin-1-yl)-phenyl |
| 1490. | 1-propen-3-yl | 4-((R)-2-trifluoromethylpyrrolidin-1-yl)-phenyl |
| 1491. | 1-propen-3-yl | 4-(3-trifluoromethylpyrrolidin-1-yl)-phenyl |
| 1492. | 1-propen-3-yl | 4-((S)-3-trifluoromethylpyrrolidin-1-yl)-phenyl |
| 1493. | 1-propen-3-yl | 4-((R)-3-trifluoromethylpyrrolidin-1-yl)-phenyl |
| 1494. | 1-propen-3-yl | 4-(2-oxopyrrolidin-1-yl)-phenyl |
| 1495. | 1-propen-3-yl | 4-(2-oxo-oxazolidin-3-yl)-phenyl |
| 1496. | 1-propen-3-yl | 4-(piperidin-1-yl)-phenyl |
| 1497. | 1-propen-3-yl | 4-(2-methylpiperidin-1-yl)-phenyl |
| 1498. | 1-propen-3-yl | 4-((S)-2-methylpiperidin-1-yl)-phenyl |
| 1499. | 1-propen-3-yl | 4-((R)-2-methylpiperidin-1-yl)-phenyl |
| 1500. | 1-propen-3-yl | 4-(piperazin-1-yl)-phenyl |
| 1501. | 1-propen-3-yl | 4-(4-methylpiperazin-1-yl)-phenyl |
| 1502. | 1-propen-3-yl | 4-(morpholin-4-yl)-phenyl |
| 1503. | 1-propen-3-yl | 4-(thiomorpholin-4-yl)-phenyl |
| 1504. | 1-propen-3-yl | 4-(1-oxo-thiomorpholin-4-yl)-phenyl |
| 1505. | 1-propen-3-yl | 4-(1,1-dioxo-thiomorpholin-4-yl)-phenyl |
| 1506. | 1-propen-3-yl | 4-(pyrrol-1-yl)-phenyl |
| 1507. | 1-propen-3-yl | 4-(pyrrol-2-yl)-phenyl |

TABLE A-continued

| No. | R¹ | Ar |
|---|---|---|
| 1508. | 1-propen-3-yl | 4-(pyrrol-3-yl)-phenyl |
| 1509. | 1-propen-3-yl | 4-(1-methylpyrrol-2-yl)-phenyl |
| 1510. | 1-propen-3-yl | 4-(1-methylpyrrol-3-yl)-phenyl |
| 1511. | 1-propen-3-yl | 4-(furan-2-yl)-phenyl |
| 1512. | 1-propen-3-yl | 4-(furan-3-yl)-phenyl |
| 1513. | 1-propen-3-yl | 4-(thiophen-2-yl)-phenyl |
| 1514. | 1-propen-3-yl | 4-(thiophen-3-yl)-phenyl |
| 1515. | 1-propen-3-yl | 4-(5-propylthien-2-yl)-phenyl |
| 1516. | 1-propen-3-yl | 4-(pyrazol-1-yl)-phenyl |
| 1517. | 1-propen-3-yl | 4-(pyrazol-3-yl)-phenyl |
| 1518. | 1-propen-3-yl | 4-(pyrazol-4-yl)-phenyl |
| 1519. | 1-propen-3-yl | 4-(1-methyl-1H-pyrazol-4-yl)-phenyl |
| 1520. | 1-propen-3-yl | 4-(1-ethyl-1H-pyrazol-4-yl)-phenyl |
| 1521. | 1-propen-3-yl | 4-(1-methyl-1H-pyrazol-5-yl)-phenyl |
| 1522. | 1-propen-3-yl | 4-(1H-imidazol-2-yl)-phenyl |
| 1523. | 1-propen-3-yl | 4-(imidazol-1-yl)-phenyl |
| 1524. | 1-propen-3-yl | 4-(1-methylimidazol-2-yl)-phenyl |
| 1525. | 1-propen-3-yl | 4-(oxazol-2-yl)-phenyl |
| 1526. | 1-propen-3-yl | 4-(oxazol-4-yl)-phenyl |
| 1527. | 1-propen-3-yl | 4-(oxazol-5-yl)-phenyl |
| 1528. | 1-propen-3-yl | 4-(isoxazol-3-yl)-phenyl |
| 1529. | 1-propen-3-yl | 4-(isoxazol-4-yl)-phenyl |
| 1530. | 1-propen-3-yl | 4-(isoxazol-5-yl)-phenyl |
| 1531. | 1-propen-3-yl | 4-([1,2,3]-triazol-1-yl)-phenyl |
| 1532. | 1-propen-3-yl | 4-([1,2,4]-triazol-1-yl)-phenyl |
| 1533. | 1-propen-3-yl | 4-([1,2,3]-triazol-2-yl)-phenyl |
| 1534. | 1-propen-3-yl | 4-(4H-[1,2,4]-triazol-3-yl)-phenyl |
| 1535. | 1-propen-3-yl | 4-([1,2,4]-triazol-4-yl)-phenyl |
| 1536. | 1-propen-3-yl | 4-(2H-[1,2,3]-triazol-4-yl)-phenyl |
| 1537. | 1-propen-3-yl | 4-(4-methyl-4H-[1,2,4]-triazol-3-yl)-phenyl |
| 1538. | 1-propen-3-yl | 4-(2-methyl-2H-[1,2,3]-triazol-4-yl)-phenyl |
| 1539. | 1-propen-3-yl | 4-([1,3,4]-oxadiazol-2-yl)-phenyl |
| 1540. | 1-propen-3-yl | 4-([1,2,4]-oxadiazol-3-yl)-phenyl |
| 1541. | 1-propen-3-yl | 4-([1,2,4]-oxadiazol-5-yl)-phenyl |
| 1542. | 1-propen-3-yl | 4-([1,2,3]-oxadiazol-4-yl)-phenyl |
| 1543. | 1-propen-3-yl | 4-([1,2,3]-oxadiazol-5-yl)-phenyl |
| 1544. | 1-propen-3-yl | 4-([1,2,3]-thiadiazol-4-yl)-phenyl |
| 1545. | 1-propen-3-yl | 4-(1H-tetrazol-5-yl)-phenyl |
| 1546. | 1-propen-3-yl | 4-(tetrazol-1-yl)-phenyl |
| 1547. | 1-propen-3-yl | 4-(2-methyl-2H-tetrazol-5-yl)-phenyl |
| 1548. | 1-propen-3-yl | 4-(1-methyl-1H-tetrazol-5-yl)-phenyl |
| 1549. | 1-propen-3-yl | 4-furazan-3-yl-phenyl |
| 1550. | 1-propen-3-yl | 4-(pyrid-2-yl)-phenyl |
| 1551. | 1-propen-3-yl | 4-(pyrid-3-yl)-phenyl |
| 1552. | 1-propen-3-yl | 4-(pyrid-4-yl)-phenyl |
| 1553. | 1-propen-3-yl | 4-(pyrimidin-2-yl)-phenyl |
| 1554. | 1-propen-3-yl | 4-(pyrimidin-4-yl)-phenyl |
| 1555. | 1-propen-3-yl | 4-(pyrimidin-5-yl)-phenyl |
| 1556. | 1-propen-3-yl | 5-isopropylthiophen-2-yl |
| 1557. | 1-propen-3-yl | 2-chlorothiophen-5-yl |
| 1558. | 1-propen-3-yl | 2,5-dichlorothiophen-4-yl |
| 1559. | 1-propen-3-yl | 2,3-dichlorothiophen-5-yl |
| 1560. | 1-propen-3-yl | 2-chloro-3-nitrothiophen-5-yl |
| 1561. | 1-propen-3-yl | 2-(phenylsulfonyl)-thiophen-5-yl |
| 1562. | 1-propen-3-yl | 2-(pyridin-2-yl)thiophen-5-yl |
| 1563. | 1-propen-3-yl | 2-(5-(trifluoromethyl)isoxazol-3-yl)-thiophen-5-yl |
| 1564. | 1-propen-3-yl | 2-(2-methylthiazol-4-yl)-thiophen-5-yl |
| 1565. | 1-propen-3-yl | 1-methyl-1H-imidazol-4-yl |
| 1566. | 1-propen-3-yl | 1,2-dimethyl-1H-imidazol-4-yl |
| 1567. | 1-propen-3-yl | 3,5-dimethylisoxazol-4-yl |
| 1568. | 1-propen-3-yl | thiazol-2-yl |
| 1569. | 1-propen-3-yl | 4-methylthiazol-2-yl |
| 1570. | 1-propen-3-yl | 4-isopropylthiazol-2-yl |
| 1571. | 1-propen-3-yl | 4-trifluoromethylthiazol-2-yl |
| 1572. | 1-propen-3-yl | 5-methylthiazol-2-yl |
| 1573. | 1-propen-3-yl | 5-isopropylthiazol-2-yl |
| 1574. | 1-propen-3-yl | 5-trifluoromethylthiazol-2-yl |
| 1575. | 1-propen-3-yl | 2,4-dimethylthiazol-5-yl |
| 1576. | 1-propen-3-yl | 2-acetamido-4-methylthiazol-5-yl |
| 1577. | 1-propen-3-yl | 4H-[1,2,4]triazol-3-yl |
| 1578. | 1-propen-3-yl | 5-methyl-4H-[1,2,4]triazol-3-yl |
| 1579. | 1-propen-3-yl | 4-methyl-4H-[1,2,4]triazol-3-yl |
| 1580. | 1-propen-3-yl | 5-isopropyl-4H-[1,2,4]triazol-3-yl |
| 1581. | 1-propen-3-yl | 5-trifluoromethyl-4H-[1,2,4]triazol-3-yl |
| 1582. | 1-propen-3-yl | 4,5-dimethyl-4H-[1,2,4]triazol-3-yl |
| 1583. | 1-propen-3-yl | 5-isopropyl-4-methyl-4H-[1,2,4]triazol-3-yl |
| 1584. | 1-propen-3-yl | 5-trifluoromethyl-4-methyl-4H-[1,2,4]triazol-3-yl |

TABLE A-continued

| No. | R¹ | Ar |
|---|---|---|
| 1585. | 1-propen-3-yl | [1,3,4]thiadiazol-2-yl |
| 1586. | 1-propen-3-yl | 5-methyl-[1,3,4]thiadiazol-2-yl |
| 1587. | 1-propen-3-yl | 5-isopropyl-[1,3,4]thiadiazol-2-yl |
| 1588. | 1-propen-3-yl | 5-trifluoromethyl-[1,3,4]thiadiazol-2-yl |
| 1589. | 1-propen-3-yl | 3-bromo-2-chloropyrid-5-yl |
| 1590. | 1-propen-3-yl | 2-(4-morpholino)-pyrid-5-yl |
| 1591. | 1-propen-3-yl | 2-phenoxypyrid-5-yl |
| 1592. | 1-propen-3-yl | (2-isopropyl)-pyrimidin-5-yl |
| 1593. | 1-propen-3-yl | (5-isopropyl)-pyrimidin-2-yl |
| 1594. | 1-propen-3-yl | 8-quinolyl |
| 1595. | 1-propen-3-yl | 5-isoquinolyl |
| 1596. | 1-propen-3-yl | 2-(2,2,2-trifluoroacetyl)-1,2,3,4-tetrahydroisoquinolin-7-yl |
| 1597. | 1-propen-3-yl | 5-chloro-3-methylbenzothiophen-2-yl |
| 1598. | 1-propen-3-yl | 3,4-dihydro-4-methyl-2H-benzo[b][1,4]oxazinyl |
| 1599. | 1-propen-3-yl | benzothiazol-6-yl |
| 1600. | 1-propen-3-yl | benzo[2,1,3]oxadiazol-4-yl |
| 1601. | 1-propen-3-yl | 5-chlorobenzo[1,2,5]oxadiazolyl |
| 1602. | 1-propen-3-yl | 7-chlorobenzo[2,1,3]oxadiazol-4-yl |
| 1603. | 1-propen-3-yl | benzo[2,1,3]thiadiazol-4-yl |

The compounds of the formula I where E is NH and $R^{1a}$ is hydrogen can be prepared by analogy to methods which are well known in the art, e.g. from the international patent applications cited in the introductory part. A preferred method for the preparation of compounds I is outlined in scheme 1:

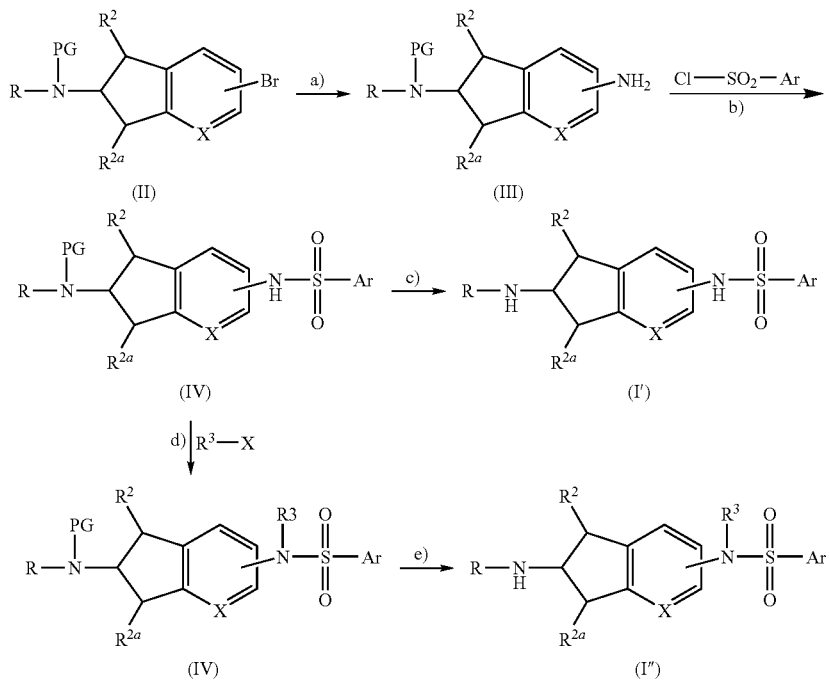

Scheme 1

In scheme 1, $R^2$, $R^{2a}$, X and Ar have the meanings as given above. R has one of the meanings given for $R^1$ or may also be hydrogen. PG is an amino-protecting group such as tert.-butoxycarbonyl. Suitable protecting groups are disclosed, for example, in P. Kocienski, Protecting Groups, Thieme-Verlag, Stuttgart 2000, Chapter 6.

In step a) of scheme 1, compound II is reacted with lithium bis(trimethylsilyl)amide in the presence of a palladium(0) compound such as tris(dibenzylideneacetone)-dipalladium (0) in the presence of a tri(substituted)phosphine, e.g. a triarylphosphine such as triphenylphosphine or tritolylphosphine, tri(cyclo)alkylphosphine such as tris-n-butylphosphine, tris(tert.-butyl)phosphine or tris(cyclohexylphosphine) according to the method described in Organic Letters (2001), 3(17), 2729-2732 and outlined below.

The thus obtained compound III is reacted with an arylchlorosulfonylchloride Cl—SO₂—Ar, preferably in the presence of a base, according to standard procedures in the art to obtain compound IV. The reaction depicted in scheme 1 step b) takes place under the reaction conditions which are customary for preparing arylsulfonamide compounds or arylsulfonic esters, respectively, and which are described, for example, in J. March, Advanced Organic Chemistry, 3$^{rd}$ edition, John Wiley & Sons, New York, 1985 p 444 and the literature cited therein, European Journal of Medicinal Chemistry (1977), 12(1), 81-66, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of III with Cl—SO$_2$—Ar is customarily carried out in the presence of an auxiliary base. Suitable bases are inorganic bases, such as sodium carbonate or potassium carbonate, or sodium hydrogencarbonate or potassium hydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound II.

If R in compound I' or I" is allyl the allyl group can be cleaved to obtain a compound I' or I" wherein R is hydrogen. The cleavage of the allyl group is achieved, for example, by reacting I [R$^1$=allyl] with an allyl trapping agent, such as mercaptobenzoic acid or 1,3-dimethylbarbituric acid, in the presence of catalytic quantities of palladium (0) compounds or palladium compounds which are able to form a palladium (0) compound under reaction conditions, e.g. palladium dichloride, tetrakis(triphenylphosphine)palladium(0) or tris (dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclo-hexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting in the presence of rhodium compounds, such as tris(triphenylphosphine)chlororhodium(I), using methods known from the literature (see J. Chem. Soc., Perkin Transaction I: Organic and Bio-Organic Chemistry 1999 (21) pp. 3089-3104 and Tetrahedron Asymmetry 1997, 8(20), pp. 3387-3391).

The resulting compound I' or I" [R$^1$=H] can then be reacted, in a known manner, in the sense of an alkylation, with a compound R$^1$—X. In this compound, R$^1$ is C$_1$-C$_4$-alkyl, C$_3$-C$_6$-cycloalkyl, C$_1$-C$_4$-haloalkyl, C$_1$-C$_4$-alkoxy-C$_1$-C$_4$-alkyl or C$_3$-C$_6$-cycloalkyl-C$_1$-C$_4$-alkyl and X is a nucleophilically displaceable leaving group, e.g. halogen, trifluoroacetate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

The alkylation of I' and I" [R=H] can also be achieved, in the sense of a reductive amination, by reacting I [R$^1$=H] with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

In case R in formula I' or I" is hydrogen, compound I' can be reacted with an acyl halide to obtain a compound of the formula I wherein R$^1$ is C$_1$-C$_3$-alkylcarbonyl. The carbonyl group in these compounds can be reduced with diborane to obtain compounds of the general formula I, wherein R is C$_2$-C$_4$-alkyl. The carbonyl group can also be reacted with a fluorinating agent to obtain a compound I wherein R$^1$ is 1,1-difluoroalkyl. J. Acylation and reduction can be achieved by standard methods, which are discussed in J. March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

As an alternative, compounds II can also be reacted with an arylsulfonylamide Ar—SO$_2$—NH$_2$ or the lithium salt thereof in the presence of a palladium(0) compound such as tris (dibenzylideneacetone)dipalladium(0) in the presence of a tri(substituted)phosphine, e.g. a triarylphosphine such as triphenylphosphine or tritolylphosphien, tri(cyclo)alkylphosphin such as tris-n-butylphosphine, tris(tert.-butyl)phosphine or tris(cyclohexylphosphine), preferably in the presence of a base such as sodium hydride according to the method described in J. Org. Chem., 68 (2993) pp 8274-8276.

Compounds of the formula I, wherein R$^{1a}$ and R$^2$ together are (CH$_2$)$_n$ with n being 2 or 3 can be prepared in manner similar to the method outlined in scheme 1 starting from a compound of the formula V, by the method outlined in scheme 2:

Scheme 2:

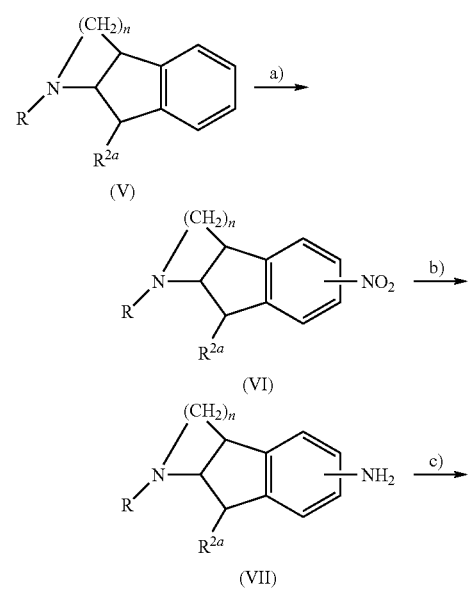

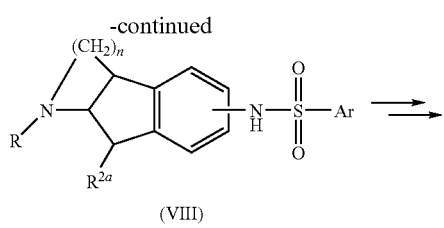

(VIII)

In scheme 2, $R^{2a}$, n and Ar have the meanings given above. R is a radical $R^1$ or an amino protecting group. In particular $R^1$ is $C_1$-$C_3$-alkylcarbonyl.

The reaction depicted in step a) in scheme 2 takes place under the reaction conditions which are customary for a nitration of an aromatic radical and which are described, for example, in J. March, Advanced Organic Chemistry, 3rd ed., John Wiley & Sons, New York 1985, pp 468-470 and the literature cited therein).

In step b), the nitro group in VI is reduced to the $NH_2$ group in VII. Subsequently, in step c), the $NH_2$ group can be converted into a —$NR^3H$ group, in which $R^3$ has the meanings different from hydrogen which are specified for $R^3$. The reaction conditions which are required for step b) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction is achieved, for example, by reacting the nitro compound VI with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of VI to VII can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound VI, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of VII with tin(II) chloride is preferably carried out in an inert organic solvent, preferably an alcohol such as methanol, ethanol, isopropanol or butanol.

Step c) in scheme 2 corresponds to step b in scheme 1, which can be performed in analogous manner. Thereby a compound of the general formula VIII is obtained which for R=$R^1$ corresponds to formula I, wherein $R^{1a}$ and $R^2$ form a $(CH_2)_n$ moiety.

The radical R in the thus obtained compounds VIII can be transformed into other radicals by the methods outlined in connection with scheme 1.

Compounds of the formula V are known in the art. They can also be prepared from (aza)indene according to the method outlined in Synlett. 1993, pp. 595-597, optionally followed by debenzylation step and an introduction of the radical R.

Compounds of the formula I, where X is N and E is NH can be also obtained by the synthetic approach outlined in scheme 3:

Scheme 3:

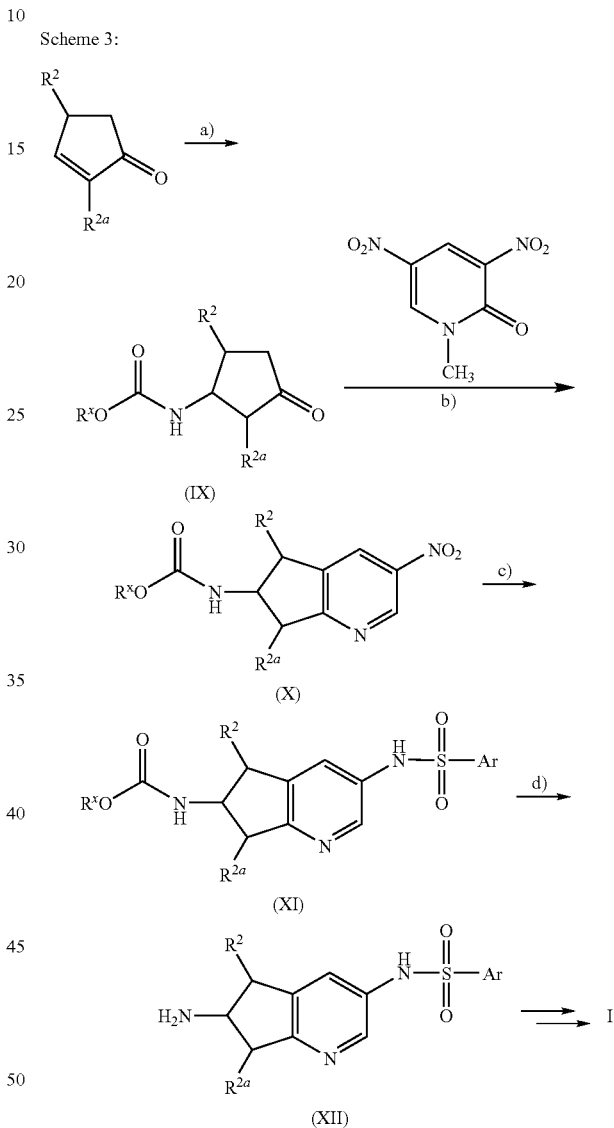

Starting from cyclopent-2-enone, selective Michael addition of a carbamate $R^xO$—C(O)—$NH_2$, in the presence of bismuth nitrate, generates the requisite β-amino ketone IX (step a, see e.g. (J. Org. Chem. 2003, 68, 2109-2114). In step b), compound IX undergoes Tohda reaction with dinitropyridone to give the azabicyclic nitro derivative X (step c), see e.g. Bull. Chem. Soc. Jpn. 1990, 63, 2820-2827; J. Med. Chem. 1996, 39, 2844-2851; Synth. Commun. 2001, 31, 787-797; Bioorg. Med. Chem. Lett. 2003, 13, 529-532). This generates a mixture of the 5- and 7-amino isomers which can be separated as either the amino or sulfonamide product. The mixture can then be reduced to the amine by the methods disclosed for step b in scheme 2, e.g. via tin chloride or catalytic hydrogenation (e.g. Pd—C/$H_2$) and subsequently converted to the desired sulfonamide by reaction with the appropriate sulfonyl chloride as outlined for step b) in scheme 1 to yield a compound of the formula XI. The amine XII may be generated by cleavage of the carbamate in the presence of an acid such as trifluoroacetic acid and converted to the target N-alkyl derivatives by processes of alkylation, acylation/reduction or reductive amination as outlined for scheme 1.

Compounds of the formula II are known in the art. They can also be prepared from 6-amino(aza)indanes of the formula XIII by the synthetic scheme outlined in scheme 4:

Scheme 4:

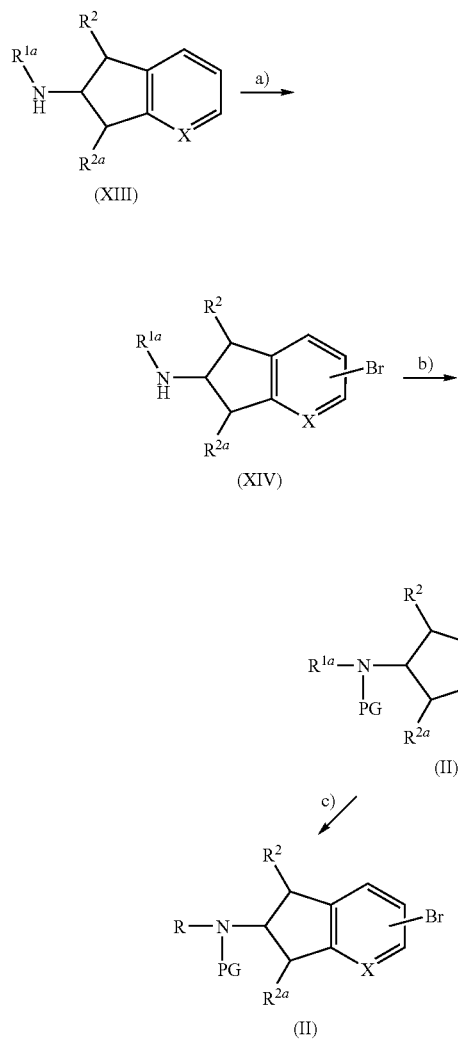

The compounds of the formula I where E is $CH_2$ can be prepared as outlined in schemes 5a and 5b:

Scheme 5a:

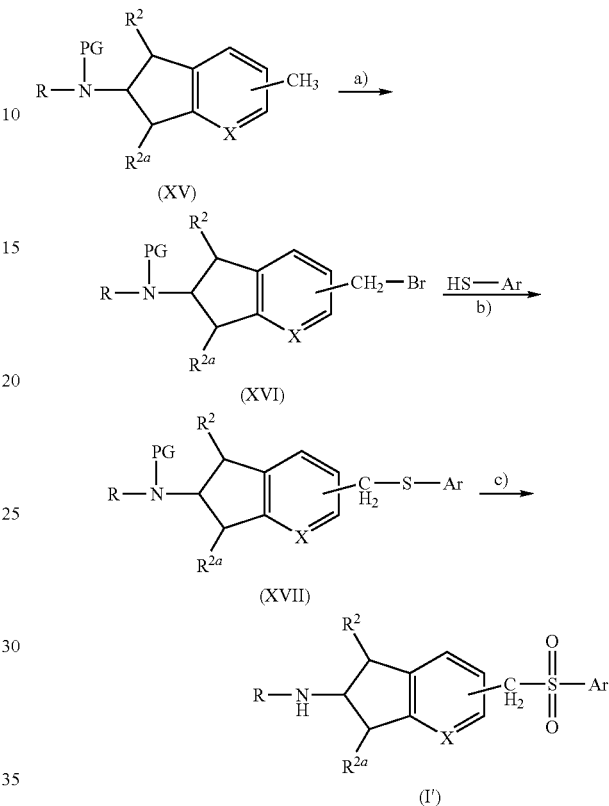

Scheme 5b:

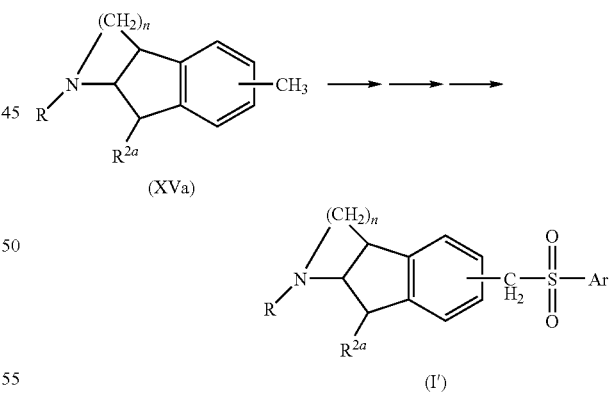

In scheme 4, $R^{1a}$, $R^2$, $R^{2a}$, PG and X have the meanings given above. R is a radical $R^1$, which is different from alkenyl or fluorinated alkenyl. In step a) the compound XIII is reacted with bromine to obtain compound XIV. The enantiomerically pure (S)- or (R)-aminoindanes XIV are e.g. prepared via crystallization of the racemic bromo-indan-2-ylamine XIV with either (S)- or (R)-10-camphersulfonic acid (Adv. Synth. Catal., 2001, 343, 5, 461-472). In step b) a protective group PG is introduced by standard methods. For $R^{1a}$ being hydrogen, the radical R is introduced by standard alkylation or acylation methods (step c).

In schemes 5a and 5b, n, $R^2$, $R^{2a}$, PG, Ar and X have the meanings given above. R is a radical $R^1$ or hydrogen. According to scheme 5a, the methyl group in compound XV is selectively brominated to yield compound XVI, which is reacted in step b) with mercapto compound HS—Ar in the presence of a base, such as sodium hydride or sodium alkoxide or with an alkali metal salt thereof thereby yielding thioether compound XVII. The thioether moiety in compound is oxidized to a sulfone moiety, e.g. by oxone, and the protective group PG is cleaved, thereby obtaining compound I', wherein the group R can be transformed as outlined for scheme 1. A similar reaction sequence can be applied to the compounds of the general formula XVa (scheme 5b).

A skilled person will readily appreciate that compounds of the formula I can also be obtained from structurally similar compounds by functional group interconversion. In particular N-bound radicals $R^a$ can be introduced into compounds of the formula I by reacting the corresponding halogen compound, i.e. a compound of the formula I, which instead of $R^a$ carries a halogen atom, in particular a bromine or iodine atom, with a primary or secondary amine in the presence of a base, preferably also in the presence of a palladium catalyst in terms of a Buchwald-Hartwig reaction.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The sulfonylchlorides Cl—SO$_2$—Ar are either commercially available or can be prepared according to standard synthetic methods. Sulfonylchlorides containing a fluorinated radical $R^a$ may be prepared by different synthetic routes, e.g. by reacting suitable hydroxy or oxo precursor (e.g. a compound Cl—SO$_2$—Ar, carrying a hydroxy or oxo substituted radical) with fluorinating reagents like DAST (diethylaminosulfurtrifluoride), morpholine-DAST, deoxofluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377). More conventionally, the hydroxy group of an aromatic compound which carries a hydroxy substituted radical but not a chlorosulfonyl group, is trans-formed into a leaving group which is then replaced by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorour pentachloride (Eur. J. Med. Chem., 2002, 36, 809-828) and the like, yields the desired sulfonylchloride (Tetrahedron Letters, 1991, 33, 50 7787-7788)) Sulfonylchlorides may also be prepared by diazotation of suitable amine precursor Ar—NH$_2$ with sodium nitrite under acidic conditions and reaction with sulfur dioxide in acetic acid (scheme (iii); J. Org. Chem., 1960, 25, 1824-26); by oxidation of suitable heteroaryl-thiols HS—Ar or heteroaryl-benzyl-thioethers C$_6$H$_5$—CH$_2$—S—Ar with chlorine (Synthesis, 1998, 36-38; J. Am. Chem. Soc., 1950, 74, 4890-92;) directly to the corresponding sulfonyl chlorides. The further are known in the art or may be prepared by standard methods. E.g. mercapto-pyrimidines or pyrimidinyl-benzylthioether precursors can e.g. be prepared according to literature (Chemische Berichte, 1960, 1208-11; Chemische Berichte, 1960, 95, 230-235; Collection Czechoslow. Chem. Comm., 1959, 24, 1667-1671; Austr. J. Chem., 1966, 19, 2321-30; Chemiker-Zeitung, 101, 6, 1977, 305-7; Tetrahedron, 2002, 58, 887-890; Synthesis, 1983, 641-645.

In the following schemes 6 to 8 several routes are shown which are suitable to prepare benzenesulfonyl chlorides carrying a fluorinated propyl radical.

Scheme 6:

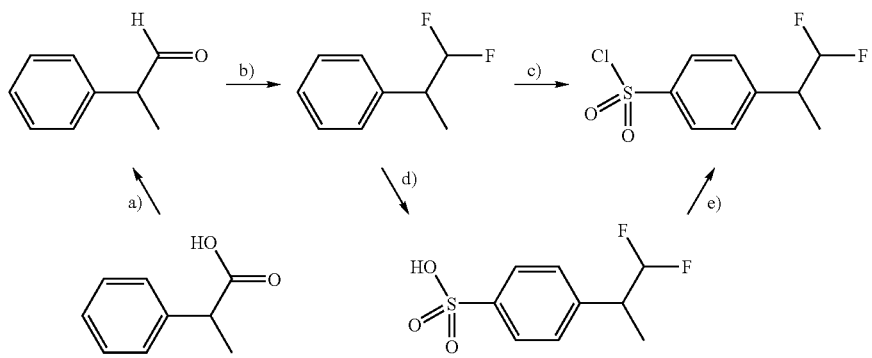

The 4-(1,1-difluoropropan-2-yl)benzene-1-sulfonyl chloride intermediate can be pre-pared from the commercially available 2-phenylpropanoic acid. In the first step a) the 2-phenylpropanic acid is converted to the alkyl ester by esterification with an alcohol (e.g. methanol or ethanol) under acid catalysis (e.g. HCl, SO$_2$Cl$_2$). The ester can be reduced to the corresponding 2-phenyl propanal by a reducing agent such as DIBAL (diisobutylaluminium hydride). The aldehyde is converted to the 1,1-difluoro-2-propyl derivative by reaction with a suitable fluorinating reagent like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 6 can also be performed using (R)-2-phenylpropanic acid and (S)-2-phenylpropanic acid respectively to give the corresponding chiral 4-(1,1-difluoropropan-2-yl)benzene-1-sulfonyl chlorides.

Scheme 7:

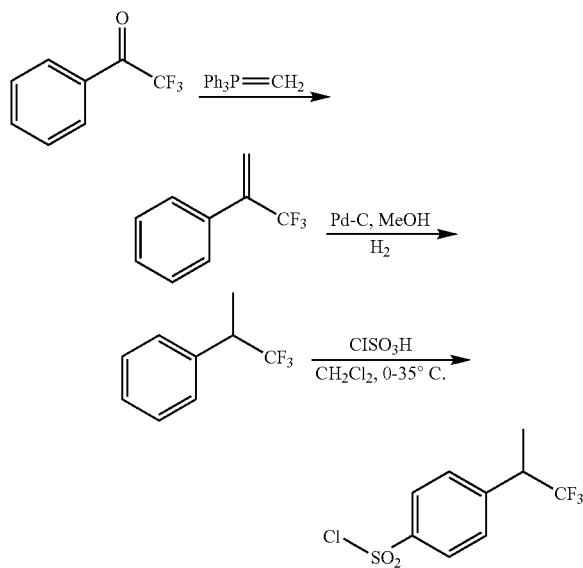

4-(1,1,1-Trifluoropropan-2-yl)benzene-1-sulfonyl chloride intermediate can be prepared from the commercially available 2,2,2-trifluoro-1-phenylethanone by a synthetic route shown in scheme 7. The ketone can be converted to the 3,3,3-trifluoro-2-phenylpropene by a Wittig reaction with a suitable ylide such as methylenetriphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable suitable base such as lithium diisopropylamide or potassium tert-butoxide. The thus obtained 3,3,3-trifluoro-2-phenylpropene can then be reduced to the saturated alkane by catalytic hydrogenation (eg Pd—C) followed by conversion to the sulfonyl chloride by the methods described in scheme 6.

The synthesis of scheme 7 can also be performed using a chiral catalyst for the alkene hydrogenation to allow the preparation of the corresponding chiral 4-(1,1,1-triifluoropropan-2-yl)benzene-1-sulfonyl chlorides.

Scheme 8:

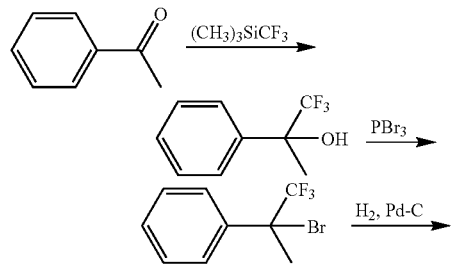

-continued

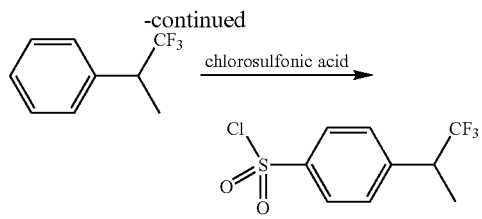

The 4-(1,1,1-trifluoropropan-2-yl)benzene-1-sulfonyl chloride can be also prepared from the commercially available 1-phenyl-ethanone by a four step procedure as shown in scheme 8. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (eg Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_1$ receptors, $D_4$ receptors, $\alpha$1-adrenergic and/or $\alpha$2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in-vitro receptor binding constants ($K_i(D_3)$) values) of as a rule less than 50 nM (nmol/l), preferably of less than 10 nM and, in particular of less than 5 nM. The displacement of [$^{125}$I]-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of [$^3$H]SCH23390, [$^{125}$I] iodosulpride or [$^{125}$I] spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gillesde-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847) and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Intermediates a. Synthesis of Sulfonyl Chlorides a.1 4-((S)-2-Fluoro-1-methyl-ethyl)-benzenesulfonyl chloride a.1.1 Toluene-4-sulfonic acid (S)-2-phenyl-propyl ester To a solution of 20 g of (S)-(−)-2-phenyl-1-propanol in 240 ml of dichloromethane was added in portions 28 g of p-toluenesulfonyl chloride (146.8 mmol). After stirring for 18 h at room temperature, the organic phase was washed with 100 ml of water, dried over magnesium sulfate, filtered, and the solvent evaporated under reduced pressure to yield 43 g of the title compound.

¹H-NMR (CDCl₃, 400 Hz): δ [ppm] 7.65 (d, 2H), 7.15-7.3 (m, 5H), 7.1 (d, 2H), 4.0-4.1 (m, 2H), 3.1 (m, 1H), 2.4 (s, 3H), 1.3 (d, 3H).

a.1.2 ((S)-2-Fluoro-1-methyl-ethyl)-benzene 9.62 g of toluene-4-sulfonic acid (S)-2-phenyl-propyl ester (33.13 mmol) were dissolved in 80 ml of polyethylenglycol 400. 9.62 g of potassium fluoride (165.6 mmol) were added and the reaction mixture was stirred at 50° C. for 3 days and another 2 days at 55-70° C. The reaction was treated with 150 ml of saturated aqueous sodium chloride solution, extracted three times with diethyl ether, and the combined organic layers were dried over magnesium sulfate, filtered, and the solvent was evaporated under reduced pressure. The crude product was purified via silica gel chromatography using cyclohexyane/ethyl acetate 15% as eluent. 2.85 g of the desired product were isolated, containing ~25% of the elimination side product.

¹H-NMR (CDCl₃, 400 Hz): δ [ppm] 7.2-7.4 (m, 5H), 4.3-4.6 (several m, 2H), 3.15 (m, 1H).1.3 (m, 3H).

a.1.3 4-((S)-2-Fluoro-1-methyl-ethyl)-benzenesulfonyl chloride 3.5 g of ((S)-2-fluoro-1-methyl-ethyl)-benzene (25.32 mmol) were dissolved in 80 ml of dichloromethane. At 0-5° C., 11.81 g of chlorosulfonic acid (101.31 mmol), dissolved in 20 ml of dichloromethane, were added dropwise. The reaction mixture was stirred for 30 min at room temperature and 2 h at 30° C. The solvent was evaporated. 150 ml of diethyl ether were added to the residue, washed once with 150 ml water, and the organic layer was dried over magnesium sulfate, filtered, and the solvent evaporated under reduced pressure. The crude product was purified via silica gel chromatography with n-heptane-dichloromethane (6:4) as eluent to give 1.5 g of the title compound.

¹H-NMR (CDCl₃, 400 Hz): δ [ppm] 8.0 (d, 2H), 7.5 (d, 2H), 4.5 (dd, 2H), 3.25 (m, 1H), 1.4 (d, 3H).

a.2 4-((R)-2-Fluoro-1-methyl-ethyl)-benzenesulfonyl chloride a.2.1 Toluene-4-sulfonic acid (R)-2-phenyl-propyl ester

Following the procedure analogous to that used for the synthesis of toluene-4-sulfonic acid (S)-2-phenyl-propyl ester, but using (R)-2-phenyl-1-propanol, the title compound was prepared a.2.2 ((R)-2-Fluoro-1-methyl-ethyl)-benzene

The title compound was prepared as described above for the synthesis of ((S)-2-fluoro-1-methyl-ethyl)-benzene, but using toluene-4-sulfonic acid (R)-2-phenylpropyl ester instead of toluene-4-sulfonic acid (S)-2-phenyl-propyl ester.

¹H-NMR (CDCl₃, 400 Hz): δ [ppm] 7.2-7.4 (m, 5H), 4.3-4.6 (several m, 2H), 3.15 (m, 1H) 1.3 (m, 3H).

a.2.3 4-((R)-2-Fluoro-1-methyl-ethyl)-benzenesulfonyl chloride 1.3 g of ((R)-2-fluoro-1-methyl-ethyl)-benzene (9.4 mmol) were dissolved in 50 ml of dichloromethane. At 0-5° C., 1.1 g of chlorosulfonic acid (9.4 mmol), dissolved in 10 ml of dichloromethane, were added dropwise. The reaction mixture was stirred for 20 min at 0-5° C. and then added to a solution of 2.15 g of phosphorous pentachloride dissolved in 40 ml of dichloromethane. The reaction mixture was stirred for 30 min at 0-5° C. and 1 h at room temperature. The solvent was evaporated, 100 ml of diethyl ether were added, the mixture was washed once with 150 ml of water, and the organic layer dried over magnesium sulfate, filtered, and the solvent evaporated under reduced pressure. The crude product was purified via silica gel chromatography with n-heptane-dichloromethane (1:1) as eluent to give 0.261 g of the title compound.

¹H-NMR (CDCl₃, 400 Hz): δ [ppm] 8.0 (d, 2H), 7.5 (d, 2H), 4.5 (dd, 2H), 3.25 (m, 1H), 1.4 (d, 3H).

a.3 4-(2-Fluoro-1-methyl-ethyl)-benzenesulfonyl chloride

Following the procedures analogous to that used for the preparation of 4-((S)-2-fluoro-1-methyl-ethyl)-benzenesulfonyl chloride, but starting with 2-phenyl-1-propanol in step a.3.1, the title compound was prepared.

¹H-NMR (CDCl₃, 400 Hz): δ [ppm] 8.0 (d, 2H), 7.5 (d, 2H), 4.5 (dd, 2H), 3.25 (m, 1H), 1.4 (d, 3H).

a.4 4-(2-Fluoro-1-fluoromethyl-ethyl)-benzenesulfonyl chloride a.4.1 (2-Fluoro-1-fluoromethyl-ethyl)-benzene 4 g of 3-phenylglutaric acid (19.21 mmol) were suspended in 350 ml of dichloromethane. At room temperature, 6.5 g of xenon difluoride (38.42 mmol) were added and the reaction mixture was stirred at room temperature for 18 h. The organic phase was washed once with 975 ml of 6% aqueous sodium hydrogencarbonate, dried over magnesium sulfate, filtered, and the solvent evaporated. The remaining residue was distilled at a bath temperature of 123° C. at 21 mm to yield 0.78 g of the title compound that contained ~50% of 4-(2-Fluoro-1-methyl-ethyl)benzene.

¹H-NMR (CDCl₃, 400 Hz): δ [ppm] 7.2-7.4 (m, 5H), 4.6-4.8 (dd, 4H), 3.3 (m, 1H).

a.4.2 4-(2-Fluoro-1-fluoromethyl-ethyl)-benzenesulfonyl chloride

Following the procedures analogous to that used for the preparation of 4-((S)-2-fluoro-1-methyl-ethyl)-benzenesulfonyl chloride, but using 5 equivalents of chlorosulfonic acid, 0.12 g of the title compound were obtained.

¹H-NMR (CDCl₃, 400 Hz): δ [ppm] 8.05 (d, 2H), 7.55 (d, 2H), 4.75 (dd, 4H), 3.4 (m, 1H).

a.5 4-(3,3,3-Trifluoropropyl)-benzenesulfonyl chloride 2.9 g were obtained from commercially available (3,3,3-trifluoropropyl)-benzene following the procedure used for the synthesis of 4-((S)-2-fluoro-1-methyl-ethyl)benzenesulfonyl chloride described above.

¹H-NMR (CDCl₃, 400 Hz): δ [ppm] 8.0 (d, 2H), 7.45 (d, 2H), 3.0 (t, 2H), 2.45 (m, 2H).

a.9 3-Bromo-4-trifluoromethoxy-benzenesulfonyl chloride 2.0 g of 1-bromo-2-(trifluoro-methoxy)benzene (8.3 mmol) were dissolved in 30 ml of dichloromethane. At 0-5°

C., 1.06 g of chlorosulfonic acid (9.13 mmol), dissolved in 3 ml of dichloromethane, were added dropwise. The reaction mixture was stirred for 30 min at room temperature. Additional 5.5 equivalents of chlorosulfonic in dichloromethane were added to drive the reaction to completion. Standard work-up was followed and silica gel chromatography with n-heptane-dichloromethane (6:4) as eluent gave 2.19 g of the title compound.

$^1$H-NMR (CDCl$_3$, 400 Hz): δ [ppm] 8.3 (d, 1H), 8.05 (dd, 1H), 7.5 (dd, 1H).

a.10 4-(2-Fluoroethyl)-benzenesulfonylchloride a.10.1 (2-Fluoroethyl)-benzene 6.8 g of were obtained from commercially available 2-phenyl-ethanol following the procedure used for the synthesis of (3-fluoropropyl)-benzene.

$^1$H-NMR (CDCl$_3$, 400 Hz): δ [ppm] 7.1-7.3 (m, 5H), 4.6 (m, 1H), 4.45 (m, 1H), 2.95 (m, 1H), 2.9 (m, 1H).

a.10.2 4-(2-Fluoroethyl)-benzenesulfonyl chloride 3.55 g were obtained following the procedure used for the synthesis of 4-((R)-2-fluoro-1-methyl-ethyl)-benzenesulfonyl chloride.

$^1$H-NMR (CDCl$_3$, 400 Hz): δ [ppm] 8.0 (d, 2H), 7.5 (d, 2H), 4.7 (dt, 2H), 3.05-3.2 (dt, 2H).

a.11 5-Propylthiophene-2-sulfonyl chloride

Following the procedures analogous to that used for the preparation of (3-fluoropropyl)-benzenesulfonyl chloride, but using only 1 equivalent of phosphorous pentachloride, the title compound was prepared.

$^1$H-NMR (CDCl$_3$, 400 Hz): δ [ppm] 7.7 (d, 1H), 6.85 (d, 1H), 2.9 (t, 2H), 1.75 (m, 2H), 1.0 (t, 3H).

a.12 4-(1-Methyl-1H-pyrazol-4-yl)-benzenesulfonyl chloride a.12.1 1-Methyl-4-phenyl-1H-pyrazole 1 g of 2-phenylmalonaldehyde (6.75 mmol) were dissolved in 25 ml of ethanol. 0.36 ml of N-methyl-hydrazine (6.75 mmol) were added, the reaction mixture was stirred under reflux for 4 h, the solvent evaporated under reduced pressure to yield 1.09 g of the product.

ESI-MS: 159.1 [M+H]+
$^1$H-NMR (CDCl$_3$, 400 Hz): δ [ppm] 7.75 (s, 1H), 7.6 (s, 1H), 7.45 (d, 2H), 7.35 (t, 2H), 7.2 (t, 1H), 3.9 (s, 3H)

a.12.2 4-(1-Methyl-1H-pyrazol-4-yl)-benzenesulfonyl chloride 0.5 g of 1-methyl-4-phenyl-1H-pyrazole (3.16 mmol) was dissolved in 20 ml of dichloromethane. At 0° C., 0.232 ml of chlorosulfonic acid were added and the reaction mixture was stirred for 1 h under ice cooling. Additional 0.7 ml of chlorosulfonic acid were added, the mixture was stirred at 0° C. for 30 minutes and then 90 minutes at 50° C. The two phases were separated and the lower layer put on ice, extracted twice with diethyl ether, dried over magnesium sulfate, filtered, and the solvent evaporated under reduced pressure to yield 0.496 g of the product.

$^1$H-NMR (CDCl$_3$, 400 Hz): δ [ppm] 8.0 (d, 2H), 7.85 (s, 1H), 7.75 (s, 1H), 7.65 (d, 2H), 4.0 (s, 3H).

a.13 4-(1,1,1-Trifluoropropan-2-yl)benzenesulfonyl chloride and 2-(1,1,1-trifluoropropan-2-yl)benzenesulfonyl chloride Prepared on a 14 g scale following the procedure outlined in Scheme 7. 2-(1,1,1-Trifluoropropan-2-yl)benzenesulfonyl chloride is a by-product of the reaction.

4-(1,1,1-Trifluoropropan-2-yl)benzenesulfonyl chloride:
MS (ESI) m/z: 273.1 [M+H]+
$^1$H-NMR (DMSO): δ [ppm] 7.62 (d, 2H), 7.33 (d, 2H), 3.81 (m, 1H), 1.42 (d, 3H).
2-(1,1,1-Trifluoropropan-2-yl)benzenesulfonyl chloride:
MS (ESI) m/z: 273.1 [M+H]+ a.14 4-(1,1-Difluoropropan-2-yl)benzenesulfonyl chloride and 2-(1,1-Difluoropropan-2-yl)benzene-1-sulfonyl chloride Prepared on an 11 g scale following the procedure outlined in Scheme 6. 2-(1,1-Difluoropropan-2-yl)benzene-1-sulfonyl chloride is a by-product of the reaction.

4-(1,1-Difluoropropan-2-yl)benzenesulfonyl chloride:
MS (ESI) m/z: 255.0 [M+H]+
$^1$H-NMR (DMSO): δ [ppm] 8.03 (d, 2H), 7.55 (d, 2H), 5.88 (dt, 1H), 3.34 (m, 1H), 1.47 (d, 3H).
$^{13}$C-NMR (DMSO): δ [ppm] 146.43, 143.54, 129.77, 127.28, 117.06 (t), 43.76, 13.78.
2-(1,1-difluoropropan-2-yl)benzene-1-sulfonyl chloride:
Isolated by chromatography on 110 mg scale.
MS (ESI) m/z: 255.0 [M+H]+
$^1$H-NMR (DMSO-d$_6$): δ [ppm] 8.15 (d, 1H), 7.77 (t, 1H), 7.70 (d, 1H), 7.54 (t, 1H), 5.99 (dt, 1H), 4.43 (m, 1H), 1.51 (d, 3H).
$^{13}$C-NMR (DMSO-d$_6$): δ [ppm] 143.45, 138.63, 135.53, 130.93, 129.04, 128.17, 116.61 (t), 38.38, 13.68.

II. Preparation of the Compounds I

Example 1

4-Isopropyl-N—((R)-2-propylamino-indan-5-yl)-benzenesulfonamide 1.1 5-Bromo-indan-2-ylamine hydrobromide 52.5 g of indan-2-ylamine (310 mmol) were dissolved in 260 ml of water and warmed to 60° C. 52.9 g of bromine (331.5 mmol) were added within 1 h. After stirring at 60-63° C. for 1 h, 47.5 ml of 50% hydrogen bromide solution were added within 5 minutes, followed by 10 minutes stirring. The reaction mixture was stirred for 1 h at room temperature, the suspension filtered and the precipitate washed 3 times with 6 ml isopropanol each. The filter cake was dried in vacuo to yield 69.6 of the crude bromo compound. This material was suspended in 150 ml of water, warmed to 100° C. and an additional 30 ml water added to get a clear solution. Stirring continued for 3 h at room temperature. The precipitate was filtered off, washed three times with 10 ml cold water and then dried in vacuo at 50° C. for 15 h to yield 58.9 g of the crystalline product.

ESI-MS: 211.9/213.9 [M+H]$^+$ $^1$H-NMR (DMSO-d$_6$): δ [ppm] 7.9-8.2 (broad, 3H), 7.5 (s, 1H), 7.4 (m, 1H), 7.25 (m, 1H), 4.0 (m, 1H), 3.2-3.35 (m, 2H), 2.85-3.0 (m, 2H).

1.2 (R)-5-Bromo-indan-2-ylamine 25 g of 5-bromo-indan-2-ylamine hydrobromide (85.32 mmol) and 9.85 ml of 4-methylmorpholin (89.59 mmol) were dissolved in 53 ml of methanol. The mixture was heated to 60° C. and a solution of 25.77 g of (1S)-(+)-campher-10-sulfonic acid (110.92 mmol) in 42 ml of methanol added within 25 minutes. The reaction mixture was stirred for 10 minutes at 60° C. and then allowed to cool down to room temperature over a 2 h time period, with stirring continuing for another 2 h. The precipitate was filtered, washed twice with 20 ml of ethyl acetate/methanol (2:1) and 20 ml of water, and finally dried at 50° C. under vacuo for 15 h to give 13.3 g of the salt.

This material was dissolved in 100 ml of 1 N aqueous sodium hydroxide and extracted three times with 250 ml of diethyl ether each. The combined organic layers were dried over magnesium sulfate, filtered, and the solvent evaporated under reduced pressure to yield 5.95 g of the indane as free base. The enanti-omeric purity was checked via chiral HPLC on a DAICEL Chiralcel OJ column (4.6×250 mm) using n-hexane:isopropanol:triethylamine (90:10:0.1) as eluent: 98% (R)-2% (S).

1.3 ((R)-5-Bromo-indan-2-yl)-carbamic acid tert-butyl ester 5.95 g of (R)-5-bromo-indan-2-ylamine (28.05 mmol) were dissolved in 100 ml of dichloromethane. 12 ml of triethylamine (86.2 mmol) and 7.65 g of di-tert.butyldicarbonate (35.07 mmol) were added, the reaction mixture stirred for 1 h at room temperature and extracted twice with 50 ml of water each. The organic phase was dried over magnesium sulfate, filtered, and the solvent evaporated under reduced pressure to yield 10.6 of product. This material was redissolved in diethyl ether, washed with water, the aqueous phase reextracted with diethyl ether, and the combined organic layers dried over magnesium sulfate, filtered, and the solvent evaporated under reduced pressure to yield 9.4 g of product.

$^1$H-NMR (CDCl$_3$): δ [ppm] 7.35 (s, 1H), 7.25 (m, 1H), 7.05 (m, 1H), 4.7 (s, broad, 1H), 4.4 (s, broad, 1H), 3.1-3.3 (m, 2H), 2.65-2.8 (m, 2H), 1.35-1.55 (9H).

1.4 ((R)-5-Bromo-indan-2-yl)-propyl-carbamic acid tert-butyl ester 3 g of ((R)-5-Bromo-indan-2-yl)-carbamic acid tert-butyl ester (9.61 mmol) were dissolved in 20 ml of dimethylformamide and 0.442 g of sodium hydride (60% in mineral oil) (11.05 mmol) added. Stirring continued for 14 minutes before 1.3 g of propylbromide (10.57 mmol) were added. The reaction mixture was stirred at room temperature for 15 h and at 40° C. for 3 h. An additional equivalent of sodium hydride and 0.7 ml propylbromide were added followed by stirring for 2 h at 40° C. and 15 h at room temperature. The solvent was evaporated under reduced pressure, the residue treated with water and extracted three times with diethyl ether. The combined organic layers were washed once with water, dried over magnesium sulfate, filtered, and the solvent evaporated under reduced pressure to yield 3.77 g of crude product which was used in the subsequent reaction without further purification.

ESI-MS: 378.0 [M+Na]$^+$ $^1$H-NMR (CDCl$_3$): δ [ppm] 7.2-7.35 (m, 2H), 7.05 (m, 1H), 4.65 (s, broad, 1H), 2.9-3.3 (several m, 6H), 1.2-1.65 (several m, 11H), 0.85 (m, 3H).

1.5 ((R)-5-amino-indan-2-yl)-propyl-carbamic acid tert-butyl ester 3.77 g of ((R)-5-Bromo-indan-2-yl)-propyl-carbamic acid tert-butyl ester (3.84 mmol) were dissolved in 70 ml toluene under argon. 0.1 g of tris(dibenzylideneacetone)dipalladium (0) (0.11 mmol) and 0.116 g of tritert.butylphosphin (0.58 mmol) were added and stirring continued for 15 minutes at room temperature. 8.5 ml of 1 molar bis-(trimethylsilyl)lithiumamide in tetrahydrofuran (8.45 mmol) were added within 10 minutes and the reaction mixture stirred at 100° C. for 3 h. After cooling to room temperature, 25 ml of 1 N hydrochloric acid and 25 ml of water were added, the phases separated, the organic phase washed again with 10 ml of 1 N hydrochloric acid. The combined aqueous phases were adjustes to alkaline pH with 50% aqueous sodium hydroxide, extracted three times with diethyl ether, the combined organic phases dried over magnesium sulfate, filtered, and the solvent evaporated under reduced pressure to yield 0.58 g of crude product which was used in the subsequent reaction without further purification.

ESI-MS: 291.1 [M+H]$^+$, 235.1 [M-tBu+H]$^+$, 191.1 [M-Boc+H]$^+$

1.6 (R)-5-(4-Isopropyl-benzenesulfonylamino)-indan-2-yl]-propyl-carbamic acid tert-butyl ester 0.58 g of ((R)-5-amino-indan-2-yl)-propyl-carbamic acid tert-butyl ester (2.0 mmol) were dissolved in 20 ml of tetrahydrofuran and 0.393 mg of 4-isopropylbenzenesulfonylchloride (1.8 mmol) and 0.83 ml of triethylamine (6 mmol) added. After stirring for 18 h at room temperature, the solvent was evaporated under reduced pressure, the remaining material partitioned between diethyl ether and water, the aqueous layer reextracted with diethylether, and the combined organic layers dried over magnesium sulfate, filtered, and the solvent evaporated. The crude material was purified via silica gel chromatography with cyclohexane-ethyl acetate (12.5%) as eluent. Fractions combining the product were combined and the solvent removed under reduced pressure to yield 0.584 g of product.

ESI-MS: 495.2 [M+Na]$^+$, 417.1 [M-tBu+H]$^+$, 373.1 [M-Boc+H]$^+$

1.7 4-Isopropyl-N—((R)-2-propylamino-indan-5-yl)-benzenesulfonamide 0.58 g of (R)-5-(4-Isopropyl-benzenesulfonylamino)-indan-2-yl]-propyl-carbamic acid tert-butyl ester (1.24 mmol) were dissolved in 10 ml of dichloromethane and 0.5 ml of trifluoroacetic acid (6.53 mmol) added. The reaction was stirred for 15 at room temperature and the solvents evaporated under reduced pressure. The residue was taken up in water, adjusted to alkaline pH with 1 N aqueous sodium hydroxide and extracted three times with diethyl ether. The combined organic layers were dried over magnesium sulfate, filtered, and the solvent evaporated to yield 0.365 g of product.

ESI-MS: 373.1 [M+H]$^+$ $^1$H-NMR (CDCl$_3$): δ [ppm] 7.65 (d, 2H), 7.25 (d, 2H), 7.0 (m, 1H), 6.9 (s, 1H), 6.8 (m, 1H), 3.65 (m, 1H), 3.05 (m, 2H), 2.9 (m, 1H), 2.6-2.7 (m, 4H), 1.5 (m, 2H), 1.2 (m, 6H), 0.9 (m, 3H).

Example 2

4-Isopropyl-N—((S)-2-propylamino-indan-5-yl)-benzenesulfonamide hydrochloride

2.1 (S)-5-Bromo-indan-2-ylamine 2.93 g of (S)-5-bromo-indan-2-ylamine were prepared as described for the (R)enantiomer starting from 12.5 of racemic 5-bromo-indan-2-ylamine and the corresponding (1R)-(−)-campher-sulfonic acid. The enantiomeric purity was checked via chiral HPLC on a DAICEL Chiralcel OJ column (4.6×250 mm) using n-hexane:isopropanol:triethylamine (90:10:0.1) as eluent: 99% (S)-1% (R).

2.2 ((S)-5-Bromo-indan-2-yl)-carbamic acid tert-butyl ester 4.81 g of ((S)-5-Bromo-indan-2-yl)-carbamic acid tert-butyl ester were prepared as described for the (R)-enantiomer.

ESI-MS: 336.0 [M+Na]$^+$, 255.9 [M-tBu+H]$^+$, 211.9 [M-Boc+H]$^+$

2.3 ((S)-5-Bromo-indan-2-yl)-propyl-carbamic acid tert-butyl ester 4.55 g of ((S)-5-Bromo-indan-2-yl)-propyl-carbamic acid tert-butyl ester were pre-pared as described for the (R)-enantiomer.

ESI-MS: 378.0 [M+Na]$^+$ $^1$H-NMR (CDCl$_3$): δ [ppm] 7.2-7.35 (m, 2H), 7.05 (m, 1H), 4.65 (s, broad, 1H), 2.9-3.3 (several m, 6H), 1.2-1.65 (several m, 11H), 0.85 (m, 3H).

2.4 ((S)-5-amino-indan-2-yl)-propyl-carbamic acid tert-butyl ester 0.59 g of ((S)-5-amino-indan-2-yl)-propyl-carbamic acid tert-butyl ester were pre-pared as described for the (R)-enantiomer.

2.5 (S)-5-(4-Isopropyl-benzenesulfonylamino)-indan-2-yl]-propyl-carbamic acid tert-butyl ester 0.381 g of (S)-5-(4-Isopropyl-benzenesulfonylamino)-indan-2-yl]-propyl-carbamic acid tert-butyl ester were pre-pared as described for the (R)-enantiomer.

ESI-MS: 495.2 [M+Na]$^+$, 417.1 [M-tBu+H]$^+$, 371.1 [M-Boc+H]$^+$

2.6 4-Isopropyl-N—((S)-2-propylamino-indan-5-yl)-benzenesulfonamide hydrochloride 0.28 g of 4-Isopropyl-N—((S)-2-propylamino-indan-5-yl)-benzenesulfonamide were prepared as described for the (R)-enantiomer.

ESI-MS: 373.1 [M+H]$^+$ $^1$H-NMR (DMSO-d$_6$): δ [ppm] 10.25 (s, 1H), 9.3 (s, broad, 2H), 7.7 (d, 2H), 7.4 (d, 2H), 7.1 (m, 1H), 7.0 (m, 1H), 6.9 (m, 1H), 3.9 (m, 1H), 2.75-3.5 (several m, 7H), 1.65 (m, 2H), 1.2 (m, 6H), 0.9 (m, 3H).

Example 3

4-isopropyl-N-methyl-N—((S)-2-propylamino-indan-5-yl)-benzenesulfonamide

3.1 {(S)-5-[(4-isopropyl-benzenesulfonyl)-methyl-amino]-indan-2-yl}-propyl-carbamic acid tert-butyl ester 0.68 mmol of ((S)-5-Bromo-indan-2-yl)-propyl-carbamic acid tert-butyl ester were dissolved in 2.5 ml of trifluoromethylbenzene. 0.077 mg of tris(dibenzylidenaceton)-dipalladium(0) (0.08 mmol) and 0.068 mg of tritert.butylphosphine (0.34 mmol) were added. 0.362 mg of 4-isopropyl-benzene-N-methyl-sulfonamide (1.7 mmol) dissolved in 2.5 ml of trifluoromethylbenzene were treated with 0.068 mg of sodium hydride (60% in mineral oil), and the resulting suspension added to the indane solution. The reaction mixture was stirred at 150° C. for 1 h in the microwave (CEM), the solvent evaporated under reduced pressure, water added and the aqueous phase extracted twice with diethyl ether. The combined organic layers were dried over magnesium sulfate, filtered, and the solvent evaporated to yield 1 g of a brownish oil that was further purified via silica gel chromatography using cyclohexane/ethyl acetate 7.5% as eluent. Fractions containing the product were combined and the solvent evaporated to yield 0.197 g of the product.

ESI-MS: 509.2 [M+Na]$^+$, 431.1 [M-tBu+H]$^+$, 387.1 [M-Boc+H]$^+$

3.2 4-Isopropyl-N-methyl-N—((S)-2-propylamino-indan-5-yl)-benzenesulfonamide 0.117 g of 4-Isopropyl-N-methyl-N—((S)-2-propylamino-indan-5-yl)benzenesulfonamide were prepared as described for the N-desmethyl compound by treatment with trifluoro acetic acid in dichloromethane.

ESI-MS: 387.1 [M+H]$^+$ $^1$H-NMR (DMSO): δ [ppm] 9.4 (s, broad, 2H), 7.45 (m, 4H), 7.2 (m, 1H), 7.0 (m, 1H), 6.85 (m, 1H), 3.95 (m, 1H), 2.8-3.45 (several m, 10H), 1.8 (m, 2H), 1.2 (m, 6H), 0.9 (m, 3H).

Example 4 trans-4-Isopropyl-N-(1-propyl-2,3,4,4a,9,9a-hexahydro-1H-indeno[2,1-b]pyridin-6-yl)benzenesulfonamide

4.1 trans-2,3,4,4a,9,9a-hexahydro-1-propyl-1H-indeno[2,1-b]pyridine

A solution of trans-2,3,4,4a,9,9a-hexahydro-1H-indeno[2,1-b]pyridinium hydrochloride (3.00 g, 14.3 mmol) and triethylamine (4.36 g, 43.1 mmol) in 95 ml of N,N-dimethylformamide was stirred at room temperature and bromopropane (1.85 g, 15.04 mmol) added dropwise. After the mixture was stirred for 18 h at room temperature, the solvent was removed and ethyl acetate/water were added. The organic layer was washed with water and dried over $MgSO_4$. The filtrate was concentrated to give a yellow oil (11.66 g, 82%).

MS (ESI+) m/z=216.1 $[M+H]^+$

4.2 trans-2,3,4,4a,9,9a-hexahydro-7-nitro-1-propyl-1H-indeno[2,1-b]pyridine and 6-nitro isomer Trans-2,3,4,4a,9,9a-hexahydro-1-propyl-1H-indeno[2,1-b]pyridine (2.50 g, 11.6 mmol) was dissolved in nitromethane (30 ml) and cooled to 5° C. A solution of concentrated $H_2SO_4$ (11.3 ml), nitric acid (1.0 ml, 65%) and water (1.80 ml) was added dropwise over 30 mins. After stirring for a further 2 hours, the solution was poured into water and extracted with ethyl acetate. The organic phase was dried over $MgSO_4$, filtered, and the filtrate was evaporated in vacuo to give the product as an orange oil (3.00 g, 99%).

MS (ESI) m/z: 261.1 $[M+H]^+$

4.3 trans-2,3,4,4a,9,9a-Hexahydro-1-propyl-1H-indeno[2,1-b]pyridin-7-amine and 6-amino isomer The mixture of nitro compounds (3.00 g, 11.5 mmol) was dissolved in methanol (100 ml) and tin chloride (10.7 g, 47.6 mmol) added. The solution was heated to reflux for 3 h and then evaporated. The residue was partitioned between ethyl acetate and NaOH (2M), and the organic phase separated and dried over $MgSO_4$. The filtered solution was concentrated and the residue separated by preparative HPLC (20-90% methanol) to give a mixture of the 6-amino and 7-amino isomers (1.59 g, 58%). A small quantity of the desired 7-amino isomer was obtained pure as a yellow oil and characterized.

MS (ESI) m/z: 231.1 $[M+H]^+$ $^1$H-NMR (DMSO): δ [ppm] 6.84 (d, 1H), 6.35 (s, 1H), 6.32 (d, 1H), 3.02 (m, 1H) 2.79 (m, 1H), 2.60 (m, 1H), 2.45 (m, 2H), 2.10 (m, 3H), 1.73 (m, 1H), 1.61 (m, 2H), 1.47 (m, 2H), 1.14 (m, 2H), 0.87 (t, 3H).

$^{13}$C-NMR (DMSO): δ [ppm] 172.1, 147.3, 145.4, 141.2, 132.1, 127.4, 124.5, 121.7, 111.7, 110.8, 108.0, 73.7, 57.2, 53.3, 48.5, 47.7, 36.1, 35.1, 27.0, 26.6, 25.6, 21.2, 19.1, 12.0.

4.4 4-Isopropyl-N-((4aS,9aS)-1-propyl-2,3,4,4a,9,9a-hexahydro-1H-indeno[2,1-b]pyridin-6-yl)-benzenesulfonamide and 4-Isopropyl-N-((4aR,9aR)-1-propyl-2,3,4,4a,9,9a-hexahydro-1H-indeno[2,1-b]pyridin-6-yl)-benzenesulfonamide The mixture of amines (200 mg, 0.87 mmol) was dissolved in pyridinedichloromethane (1:2, 15 ml) and cooled to 5° C. 4-Isopropylbenzenesulfonyl chloride (200 mg, 0.91 mmol) was added and the solution stirred at 5° C. for 18 h. Solution was evaporated, partitioned between ethyl acetate and water, and the organic phase separated and dried over $MgSO_4$. The filtered solution was concentrated and separated by preparative chiral HPLC (20-95% methanol) to give the pure (RR) and (SS) products and a mixed fraction (92 mg, 22%). The 1$^{st}$ product was obtained as a colorless oil (21 mg, 5%) and is 4-isopropyl-N((4aS,9aS)-1-propyl-2,3,4,4a,9,9a-hexahydro-1H-indeno[2,1-b]pyridin-6-yl)benzenesulfonamide; the 2$^{nd}$ product, 4-isopropyl-N-((4aR,9aR)-1-propyl-2,3,4,4a,9,9a-hexahydro-1H-indeno[2,1-b]pyridin-6-yl)-benzenesulfonamide, was obtained as a colorless oil (8.5 mg, 2%).

4-Isopropyl-N-((4aS,9aS)-1-propyl-2,3,4,4a,9,9a-hexahydro-1H-indeno[2,1-b]pyridin-6-yl)-benzenesulfonamide:

MS (ESI) m/z: 413.1 $[M+H]^+$ $^1$H-NMR (DMSO): δ [ppm] 7.69 (d, 2H), 7.42 (d, 2H), 7.14 (d, 1H), 6.94 (m, 2H), 3.60 (d, 1H), 3.30 (m, 1H), 3.15 (m, 2H), 2.90 (m, 4H), 2.65 (m, 4H), 2.22 (m, 1H), 1.91 (m, 1H), 1.70 (m, 2H), 1.22 (d, 6H), 0.88 (t, 3H);

4-Isopropyl-N-((4aR,9aR)-1-propyl-2,3,4,4a,9,9a-hexahydro-1H-indeno[2,1-b]pyridin-6-yl)-benzenesulfonamide:

MS (ESI) m/z: 413.1 $[M+H]^+$ $^1$H-NMR (DMSO): δ [ppm] 7.68 (d, 2H), 7.41 (d, 2H), 7.14 (m, 2H), 6.94 (m, 1H), 3.61 (d, 1H), 3.22 (m, 2H), 3.13 (m, 1H), 2.92 (m, 5H), 2.31 (m, 2H), 1.95 (m, 2H), 1.74 (m, 2H), 1.40 (m, 2H), 1.19 (d, 6H), 0.93 (t, 3H).

Example 5

Reference Example

N—((R)-2-Amino-indan-5-yl)-4-(2,2-difluoro-cyclopropyl)-benzenesulfonamide

Following the standard sulphonamide coupling procedure analogous to that described above and TFA deprotection of the BOC-group as described above the title compound was prepared. Yield for the two steps: 65%.

MS (ESI) m/z: 365.1 $[M+H]^+$ $^1$H-NMR (DMSO): δ [ppm] 10.24 (s, 1H), 8.00 (br s, 2H), 7.71 (d, 2H), 7.48 (d, 2H), 7.12 (d, 1H), 7.02 (s, 1H), 6.96 (d, 1H), 3.96 (m, 1H), 3.14 (m, 3H), 2.83 (m, 2H), 2.01 (m, 2H).

Example 6

N—((R)-2-Allylamino-indan-5-yl)-4-(2,2-difluoro-cyclopropyl)-benzenesulfonamide Following the standard sulphonamide coupling procedure analogous to that described above and TFA deprotection of the BOC-group as described above the title compound was prepared. Yield for the two steps: 33%.

MS (ESI) m/z: 405.1 $[M+H]^+$ $^1$H-NMR (MeOD): δ [ppm] 7.66 (d, 1H), 7.60 (d, 1H), 7.22 (m, 2H), 6.98 (d, 1H), 6.94 (s, 1H), 6.79 (d, 1H), 5.82 (m, 1H), 5.30 (m, 2H), 3.81 (m, 1H), 3.42 (m, 4H), 3.06 (m, 2H), 2.80 (m, 2H), 1.81 (m, 1H), 1.67 (m, 1H).

Example 7

N—((R)-2-Dipropylamino-indan-5-yl)-4-isopropyl-benzenesulfonamide hydrochloride Following the standard sulphonamide coupling procedure analogous to that described above and TFA deprotection of the BOC-group as described above the title compound was prepared.

ESI-MS: 415.3 $[M+H]^+$ $^1$H-NMR (DMSO-$d_6$, 400 Hz): δ [ppm] 11.0 (bs, 1H), 10.2 (s, 1H), 7.7 (d, 2H), 7.4 (d, 2H), 7.05 (d, 1H), 7.0 (s, 1H), 6.9 (d, 1H), 4.1 (m, 1H), 3.1-3.3 (m, 4H), 2.85-3.05 (m, 5H), 1.7 (m, 4H), 1.15 (d, 6H), 0.9 (t, 6H).

The compounds of the general formula I.1 And 1.2 ((R)- and (S)-isomers of compounds I with $R^{1a}$=H; $R^2$=H, $R^{2a}$=H, X=CH; E=NH) and the compounds of the general formula I.3 (compounds I with $R^{1a}$ and $R^2$ together are —CH₂—CH₂—CH₂—, X=CH; E=NH) listed in Table 1, 2 and 3 below can be prepared in an analogous manner.

TABLE 1

(I.1)

| Ex # | R¹ | Ar | spectroscopic data/ melting point [° C.] |
|---|---|---|---|
| 8 | propyl | 4-(1-fluoro-1-methyl-ethyl)phenyl | |
| 9 | propyl | 4-(2-fluoro-ethyl)phenyl | |
| 10 | propyl | 4-(2,2,2-trifluoroethyl)phenyl | |
| 11 | propyl | 4-(1,1-difluoroethyl)phenyl | |
| 12 | propyl | 4-(2,2-difluorocyclopropyl)phenyl | |
| 13 | propyl | 4-((R)-1-fluoro-ethyl)phenyl | |
| 14 | propyl | 4-((S)-1-fluoro-ethyl)phenyl | |
| 15 | propyl | 4-(1-difluoromethyl-2,2-difluoro-ethyl)phenyl | |
| 16 | propyl | 4-((S)-2,2,2-trifluoro-1-methyl-ethyl)phenyl | |
| 17 | propyl | 4-((R)-2,2,2-Trifluoro-1-methyl-ethyl)phenyl | |
| 18 | propyl | 4-((S)-2,2-difluoro-1-methyl-ethyl)phenyl | |
| 19 | propyl | 4-((R)-2,2-difluoro-1-methyl-ethyl)phenyl | |
| 20 | propyl | (5-isopropyl)pyrimidyl-2-yl | |
| 21 | propyl | (2-isopropyl)pyrimidyl-5-yl | |
| 22 | propyl | (5-isopropyl)thiophen-2-yl | |
| 23 | ethyl | 4-isopropyl-phenyl | |
| 24 | methyl | 4-isopropyl-phenyl | |
| 25 | 2-fluoro-ethyl | 4-isopropyl-phenyl | |
| 26 | allyl | 4-isopropyl-phenyl | |
| 27 | 3-fluoro-propyl | 4-isopropyl-phenyl | |
| 28 | propyl | 4-cyclopropyl-phenyl | |
| 29 | propyl | 4-cyclobutyl-phenyl | |
| 30 | propyl | 4-((R)-2-fluoro-1-methyl-ethyl)phenyl | |
| 31 | propyl | 4-((S)-2-Fluoro-1-methyl-ethyl)phenyl | |
| 32 | propyl | 4-(2-fluoro-1-fluoromethyl-ethyl)phenyl | |

TABLE 2

(I.2)

| Ex # | R¹ | Ar | spectroscopic data/ melting point [° C.] |
|---|---|---|---|
| 33 | propyl | 4-((R)-2-fluoro-1-methyl-ethyl)phenyl | |
| 34 | propyl | 4-((S)-2-fluoro-1-methyl-ethyl)phenyl | |
| 35 | propyl | 4-(2-fluoro-1-fluoromethyl-ethyl)phenyl | |
| 36 | propyl | 4-(1-fluoro-1-methyl-ethyl)phenyl | |
| 37 | propyl | 4-(2-fluoro-ethyl)phenyl | |
| 38 | propyl | 4-(2,2,2-trifluoroethyl)phenyl | |
| 39 | propyl | 4-(1,1-difluoroethyl)phenyl | |
| 40 | propyl | 4-(2,2-difluorocyclopropyl)phenyl | |
| 41 | propyl | 4-((R)-1-fluoro-ethyl)phenyl | |
| 42 | propyl | 4-((S)-1-fluoro-ethyl)phenyl | |
| 43 | propyl | 4-(1-difluoromethyl-2,2-difluoro-ethyl)phenyl | |
| 44 | propyl | 4-((S)-2,2,2-trifluoro-1-methyl-ethyl)phenyl | |
| 45 | propyl | 4-((R)-2,2,2-trifluoro-1-methyl-ethyl)phenyl | |
| 46 | propyl | 4-((S)-2,2-difluoro-1-methyl-ethyl)phenyl | |
| 47 | propyl | 4-((R)-2,2-difluoro-1-methyl-ethyl)phenyl | |
| 48 | propyl | (5-isopropyl)pyrimidyl-2-yl | |
| 49 | propyl | (2-isopropyl)pyrimidyl-5-yl | |
| 50 | propyl | (5-isopropyl)thiophen-2-yl | |
| 51 | ethyl | 4-isopropyl-phenyl | |
| 52 | methyl | 4-isopropyl-phenyl | |
| 53 | 2-fluoro-ethyl | 4-isopropyl-phenyl | |
| 54 | allyl | 4-isopropyl-phenyl | |
| 55 | 3-fluoro-propyl | 4-isopropyl-phenyl | |
| 56 | propyl | 4-cyclopropyl-phenyl | |
| 57 | propyl | 4-cyclobutyl-phenyl | |

TABLE 3

(I.3)

| Ex # | R¹ | Ar | spectroscopic data/ melting point [° C.] |
|---|---|---|---|
| 58 | propyl | 4-((R)-2-fluoro-1-methyl-ethyl)phenyl | |
| 59 | propyl | 4-((S)-2-fluoro-1-methyl-ethyl)phenyl | |
| 60 | propyl | 4-(2-fluoro-1-fluoromethyl-ethyl)phenyl | |
| 61 | propyl | 4-(1-fluoro-1-methyl-ethyl)phenyl | |
| 62 | propyl | 4-(2-fluoro-ethyl)phenyl | |
| 63 | propyl | 4-(2,2,2-trifluoroethyl)phenyl | |
| 64 | propyl | 4-(1,1-difluoroethyl)phenyl | |
| 65 | propyl | 4-(2,2-difluorocyclopropyl)phenyl | |
| 66 | propyl | 4-((R)-1-fluoro-ethyl)phenyl | |
| 67 | propyl | 4-((S)-1-fluoro-ethyl)phenyl | |
| 68 | propyl | 4-(1-difluoromethyl-2,2-difluoro-ethyl)phenyl | |
| 69 | propyl | 4-((S)-2,2,2-trifluoro-1-methyl-ethyl)phenyl | |
| 70 | propyl | 4-((R)-2,2,2-trifluoro-1-methyl-ethyl)phenyl | |
| 71 | propyl | 4-((S)-2,2-difluoro-1-methyl-ethyl)phenyl | |
| 72 | propyl | 4-((R)-2,2-difluoro-1-methyl-ethyl)phenyl | |
| 73 | propyl | (5-isopropyl)pyrimidyl-2-yl | |
| 74 | propyl | (2-isopropyl)pyrimidiyl-5-yl | |
| 75 | propyl | (5-isopropyl)thiophen-2-yl | |
| 76 | ethyl | 4-isopropyl-phenyl | |
| 77 | methyl | 4-isopropyl-phenyl | |
| 78 | 2-fluoro- | 4-isopropyl-phenyl | |

TABLE 3-continued (I.3)

[structure showing a tetrahydroisoquinoline-indane-sulfonamide compound with R¹ and Ar substituents]

| Ex # | R¹ | Ar | spectroscopic data/ melting point [° C.] |
|---|---|---|---|
|  | ethyl |  |  |
| 79 | allyl | 4-isopropyl-phenyl |  |
| 80 | 3-fluoro-propyl | 4-isopropyl-phenyl |  |
| 81 | propyl | 4-cyclopropyl-phenyl |  |
| 82 | propyl | 4-cyclobutyl-phenyl |  |

Examples of Galenic Administration Forms

A) Tablets

Tablets of the following composition are pressed on a tablet press in the customary manner:

40 mg of substance from Example 8
120 mg of corn starch
13.5 mg of gelatin
45 mg of lactose
2.25 mg of Aerosil ® (chemically pure silicic acid in submicroscopically fine dispersion)
6.75 mg of potato starch (as a 6% paste)

B) Sugar-coated tablets

| 20 mg | of substance from Example 8 |
| 60 mg | of core composition |
| 70 mg | of saccharification composition |

The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

Biological Investigations

Receptor Binding Studies:

The substance to be tested was either dissolved in methanol/Chremophor® (BASF-AG) or in dimethyl sulfoxide and then diluted with water to the desired concentration.

Dopamine $D_3$ Receptor:

The assay mixture (0.250 ml) was composed of membranes derived from ~$10^6$ HEK-293 cells possessing stably expressed human dopamine $D_3$ receptors, 0.1 nM [$^{125}$I]-iodosulpride and incubation buffer (total binding) or, in addition, test sub-stance (inhibition curve) or 1 μM spiperone (nonspecific binding). Each assay mixture was run in triplicate.

The incubation buffer contained 50 mM tris, 120 mM NaCl, 5 mM KCl, 2 mM CaCl₂, 2 mM MgCl₂ and 0.1% bovine serum albumin, 10 μM quinolone and 0.1% ascorbic acid (prepared fresh daily). The buffer was adjusted to pH 7.4 with HCl. Dopamine $D_{2L}$ receptor:

The assay mixture (1 ml) was composed of membranes from ~$10^6$ HEK-293 cells possessing stably expressed human dopamine $D_{2L}$ receptors (long isoform) and 0.01 nM [$^{125}$I] iodospiperone and incubation buffer (total binding) or, in addition, test substance (inhibition curve) or 1 μM haloperidol (nonspecific binding). Each assay mixture was run in triplicate.

The incubation buffer contained 50 mM tris, 120 mM NaCl, 5 mM KCl, 2 mM CaCl₂, 2 mM MgCl₂ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptro binding studies are expressed as receptor binding constants $K_i(D_2)$ and $K_i(D_3)$, respectively, as herein before described, and given in table 4.

In these tests, the compounds according to the invention exhibit very good affinities for the $D_3$ receptor (<10 nM, frequently <5 nM) and bind selectively to the $D_3$ receptor.

The results of the binding tests are given in table 4.

TABLE 4

| Example | $K_i(D3)$* [nM] | $K_i(D2)$* [nM] | $K_i(D2)$*/$K_i(D3)$* |
|---|---|---|---|
| 1 | 4.0 | 257 | 64 |
| 2 | 6.7 | 132 | 20 |
| 3 | 7.0 | 157 | 22 |
| 4 (SS)-isomer | 1.6 |  | 17 |
| 4 (RR)-isomer | 9.4 |  | 134 |
| 7 | 0.26 | 51 | 195 |

*Receptor binding constants obtained according to the assays described herein before

We claim:

1. A 6-amino(aza)indane compound of the formula I

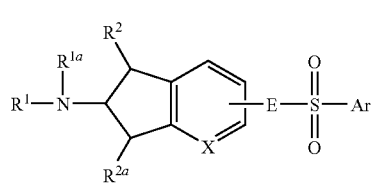

(I)

wherein

Ar is phenyl or an aromatic 5- or 6-membered C-bound heteroaromatic radical, wherein Ar carries 1 radical $R^a$ and wherein Ar may also carry 1 or 2 radicals $R^b$;

$R^a$ being selected from the group consisting of $C_1$-$C_6$-alkyl, $C_2$-$C_6$-alkenyl, fluorinated $C_2$-$C_6$-alkenyl, $C_3$-$C_6$-cycloalkyl, $C_1$-$C_6$-alkoxy, fluorinated $C_2$-$C_6$-alkyl fluorinated $C_3$-$C_6$-cycloalkyl, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2,NR^4R^5$, $ONR^4R^5$, NHC(O)$NR^4R^5$, $C_1$-$C_6$ alkylcarbonyl, fluorinated $C_1$-$C_6$-alkylcarbonyl, $C_1$-$C_6$ alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$ alkylsulfinyl, phenylsulfonyl, phenyl, phenoxy, benzyloxy and a 3- to 7-membered heterocyclic radical, wherein the five last mentioned radicals may carry 1, 2, 3 or 4 radicals selected from halogen, cyano, OH, oxo, CN, and the radicals $R^a$, $R^b$ being, independently from each other, selected from halogen, cyano, nitro, OH, methyl, methoxy, fluoromethyl, difluoromethyl, trifluoromethyl, fluormethoxy, difluoromethoxy and trifluoromethoxy, the radical $R^a$ and one radical $R^b$, if present and bound to two adjacent carbon atoms of phenyl, may form a 5- or 6-membered heterocyclic or carbocylic ring which is fused to the phenyl ring and which is unsubstituted or which may carry 1, 2 or 3 radicals selected from halogen, $NO_2$, NH OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$alkoxy-$C_2$-$C_4$-alkyl, $C_1$-$C_6$-hydroxyalkoxy, $C_1$-$C_4$alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl, provided that if Ar is phenyl, $R^2$ is hydrogen and $R^{2a}$ is hydrogen, Ar carries 1 radical $R^a$ which is different from methyl, methoxy, and trifluoromethoxy, and optionally 1 or 2 radicals $R^b$;

X is CH;

E is $CR^6R^7$ or $NR^3$;

$R^1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H or $R^{1a}$ and $R^2$ or $R^{1a}$ and $R^{2a}$ together are $(CH_2)$ with n being 1, 2, 3 or 4;

$R^2$ and $R^{2a}$ each independently are H, CH $CH_2F$, $CHF_2$ or $CF_3$;

$R^3$ is H or $C_1$-$C_4$-alkyl;

$R^4$, $R^5$ independently of each other are selected from H, $C_1$-$C_2$-alkyl, $C_1$-$C_2$-alkoxy and fluorinated $C_1$-$C_2$-alkyl;

$R^6$, $R^7$ independently of each other are selected from H, $C_1$-$C_2$-alkyl and fluorinated $C_1$-$C_2$-alkyl;

and the physiologically tolerated acid addition salts of these compounds.

2. A 6-amino(aza)indane compound of the formula I as defined in claim 1, wherein, Ar is phenyl or an aromatic 5- or 6-membered C-bound heteroaromatic radical, having 1 nitrogen atom as ring member and 0, 1, 2 or 3 further heteroatoms, independently of each other, selected from O, S and N, as ring members, wherein Ar carries 1 radical $R^a$ which is selected from the group consisting of $C_1$-$C_6$-alkyl, $C_3$-$C_6$-cycloalkyl, $C_1$-$C_6$-alkoxy, fluorinated $C_2$-$C_6$-alkyl, fluorinated $C_3$-$C_6$-cycloalkyl, fluorinated $C_1$-$C_6$-alkoxy, $NR^4R^5$, 1-aziridinyl, azetidin-1-yl, pyrrolidin-1-yl or piperidin-1-yl, wherein the last four mentioned radicals may be fluorinated, a phenyl group and an aromatic 5- or 6-membered C-bound heteroaromatic radical, having 1 nitrogen atom as ring member and 0, 1, 2 or 3 further heteroatoms, independently of each other, selected from O, S and N, wherein the last two mentioned radicals may carry 1, 2, 3 or 4 radicals selected from Halogen and the radicals $R^a$, and wherein Ar may carry 1 or 2 further radicals $R^b$, which are independently from each other selected from halogen, cyano, methyl, fluoromethyl, difluoromethyl, trifluoromethyl, difluoromethoxy and trifluoromethoxy; and wherein E is CH, or $NR^3$, $R^3$ being H or $C_1$-$C_4$-alkyl, $R^1$ is $C_2$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^4$, $R^5$ are, independently of each other, selected from H, $C_1$-$C_2$-alkyl and fluorinated $C_1$-$C_2$-alkyl; and X, $R^{1a}$, $R^2$, and $R^{2a}$ are as defined in claim 1.

3. The compounds as claimed in claim 1, wherein Ar carries one radical $R^a$ of the formula $R^{a'}$

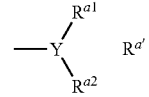

wherein

Y is N, CH or CF, $R^{a1}$ and $R^{a2}$ are independently of each other selected from $C_1$-$C_2$-alkyl, $C_1$-$C_2$-alkoxy, fluorinated $C_1$-$C_2$-alkyl, provided for Y being CH or CF one of the radicals $R^{a1}$ or $R^{a2}$ may also be hydrogen or fluorine, or $R^{a1}$ and $R^{a2}$ together form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6.

4. The compounds as claimed in claim 3, wherein the radical $R^{a'}$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyhethyl, 1-(difluoromethyl)-2,2-difluoroethyl, 1-fluoro-1-methylethyl, cyclopropyl, cyclobutyl, 1-fluorocyclopropyl, 2,2-difluorocyclopropyl and 2-fluorocyclopropyl.

5. The compounds as claimed in claim 3, wherein the radical $R^{a'}$ is selected from 4-morpholinyl, 4-thiomorpholinyl, 4-(1,1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, 2-oxo-oxazolidin-3-yl, piperidin-1-yl, 2-methylpiperidin-1-yl, (S)-2-methylpiperidin-1-yl and (R)-2-methylpiperidin-1-yl.

6. The compounds as claimed in claim 3, wherein the radical $R^{a'}$ carries 1, 2, 3 or 4 fluorine atoms.

7. The compounds as claimed in claim 1, wherein Ar carries one radical $R^a$, which is $OCH_2F$.

8. The compounds as claimed in claim 1, wherein Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, NH OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_1$-$C_4$-alkyl, $C_1$-$C_6$-hydroxyalkoxy, $C_1$-$C_4$-alkoxy-$C_1$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

9. The compounds as claimed in claim 8, wherein Ar carries one heteroaromatic radical $R^a$, which is selected from furanyl, thienyl, pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents selected from halogen, $C_1$-$C_4$-alkyl, $C_1$-$C_4$-alkoxy, fluorinated $C_1$-$C_4$-alkyl and fluorinated $C_1$-$C_4$-alkoxy.

10. The compounds as claimed in claim 1, wherein Ar is phenyl.

11. The compounds as claimed in claim 1, wherein Ar is phenyl that carries a radical $R^a$ in the 4-position of the phenyl ring.

12. The compounds as claimed in claim 1, wherein E is $NR^3$.

13. The compounds as claimed in claim 1, wherein E is $CH_2$.

14. The compounds as claimed in claim 1, wherein $R^{1a}$, $R^2$ and $R^{2a}$ are hydrogen.

15. The compounds as claimed in claim 1, wherein $R^1$ is n-propyl or 1-propen-3-yl.

16. A pharmaceutical composition comprising at least one compound of the formula I or a pharmaceutically acceptable salt thereof as claimed in claim 1, optionally together with at least one physiologically acceptable carrier or auxiliary substance.

17. A method for treating a medical disorder selected from the group consisting of Parkinson's disease, schizophrenia, cognitive disturbances, depression, anxiety, addiction, kidney function disturbances, and eating disturbances, said method comprising administering an effective amount of at least one compound of the formula I or a pharmaceutically acceptable salt thereof as claimed in claim 1 to a subject in need thereof.

18. A compound selected from the group consisting of:
- 4-(Difluoromethoxy)-N-(2-propylaminoindan-5-yl)-benzenesulfonamide;
- 4-(1,1,2,2-Tetrafluoroethoxy)-N-(2-propylaminoindan-5-yl)-benzenesulfonamide;
- 4-(2,2,2-Trifluoroethoxy)-N-(2-propylaminoindan-5-yl)-benzenesulfonamide;
- 4-(2,2-Difluoroethoxy)-N-(2-propylaminoindan-5-yl)-benzenesulfonamide;
- 4-(2-Fluoroethoxy)-N-(2-propylaminoindan-5-yl)-benzenesulfonamide;
- 4-(2,2,2-Trifluoroethyl)-N-(2-propylaminoindan-5-yl)-benzenesulfonamide; and
- 4-(2-Fluoro-1-methylethyl)-N-(2-propylaminoindan-5-yl)-benzenesulfonamide.

* * * * *